United States Patent [19]
Leitner et al.

[11] Patent Number: 5,827,706
[45] Date of Patent: Oct. 27, 1998

[54] CYCLOSPORIN SYNTHETASE

[75] Inventors: Ernst Leitner, Kundl; Elisabeth Schneider, Rum; Kurt Schoergendorfer; Gerhard Weber, both of Unterlangkampfen, all of Austria

[73] Assignee: Novartis AG, Basel, Switzerland

[21] Appl. No.: 471,119

[22] Filed: Jun. 6, 1995

Related U.S. Application Data

[63] Continuation of Ser. No. 263,960, Jun. 20, 1994, abandoned, which is a continuation of Ser. No. 90,522, Jul. 9, 1993, abandoned.

[30]  Foreign Application Priority Data

| Jul. 9, 1992 | [AT] | Austria | 1403/92 |
| Mar. 8, 1993 | [AT] | Austria | 437/93 |
| Apr. 29, 1993 | [CH] | Switzerland | 01310/93 |
| May 4, 1993 | [CH] | Switzerland | 01375/93 |

[51] Int. Cl.$^6$ .............. C12N 9/00; C12N 5/00; C12N 15/00; C07H 17/00
[52] U.S. Cl. ............. 435/183; 435/325; 435/320.1; 536/23.2
[58] Field of Search .............. 536/23.2, 23.7, 536/24.32; 435/68.1, 69.1, 183, 250.3, 320.1, 325

[56] References Cited

FOREIGN PATENT DOCUMENTS 445686  9/1991  European Pat. Off. .

OTHER PUBLICATIONS

MacCabe et al 1991 J Biol Chem 266:12646–12654.
Bergsma et al., J. Biol. Chem. 266, 23204–23214 (1991).
Caroni et al., J. Biol. Chem. 266, 10739–10742 (1991).
Gasser et al., Proc. Natl. Acad. Sci. USA 87, 9519–9523 (1990).
Stamnes et al., Cell 65, 219–227 (1991).
Tropschug, Nucleic Acids Research 18, 190 (1990).
Billich et al., J. Biol. Chem. 262, 17258–17259 (1987).
Dittmann et al., Biol. Chem. Hoppe–Seyler 371, 829–834 (1990).
George et al., Macromolecular Sequencing nad Synthesis, Selected Methods and Applications, Allan R. Liss, Inc., New York (1988), pp. 127–149.
Haese et al., Mol. Microbiol. 7, 905–914 (1993).
Honore et al., Nucl. Acids Res. 18, 6692 (1990).
Huynh et al., Constructing and Screening cDNA Libraries in λgt10 and λgt11, *DNA Cloning*, vol. 1, IRL Press (1985), pp. 49–78.
Kleinkauf et al., Eur. J. Biochem. 192, 1–15 (1990).
Kleinkauf et al., Biomed. Biochim. Acta 50, 219–224 (1991).
Lawen et al., J. Antibiot. (Tokyo) 42, 1283–1289 (1989).
Lawen et al., J. Biol. Chem. 265, 11355–11360 (1990).
Lawen et al., J. Biol. Chem. 266, 15567–15570 (1991).
Lawen et al., Biochimie 74, 511–516 (1992).
Marahiel et al., Mol. Gen. Genet. 201, 231–236 (1985).
Pierce et al., Proc. Natl. Acad. Sci. USA 89, 2056–2060 (1992).
Schmidt et al., FEBS 307, 355–360 (1992).
Tropschug et al., J. Biol. Chem. 263, 14433–14440 (1988).
Zocher et al., Biochemistry 25, 550–553 (1986).
Reek et al. 1987 Cell 50:667.

*Primary Examiner*—Karen Cochrane Carlson
*Attorney, Agent, or Firm*—Melvyn M. Kassenoff

[57]  ABSTRACT

The nucleotide sequence which codes for cyclosporin synthetase and similar enzymes and recombinant vectors containing the sequence. The vectors are used in methods for the production of cyclosporin and cyclosporin derivatives.

9 Claims, 5 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 46899 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Tolypocladium niveum
        ( B ) STRAIN: ATCC 34921

( x i ) SEQUENCE DESCRIPTION: SEQ ID NO:1:

```
GAATTCAGTA  TCGGGCAAAT  CTTCATGGTG  ATGTGAATCT  AGCGAGATGA  ATGCAGGAGA      60

ATCGGCTGGG  ATGGCCTCCA  GATATACACC  CTTCTAGCAT  CACAAATCCC  GCCGATGTAC     120

AAGCCCCACG  ACGAACGTTC  TTATTGGCTT  AACCGCTACT  AGTATTTTA   TATAGTAGTT    180

TATATGCGTA  GGTACTCTCT  TCTGTTAATG  TCAGAGGATC  TATTGCGATG  GGCAGGCTGC    240

AGCAATGCCT  CGATCTTGAT  GGAGGGATAG  TTGTTTGCTG  ATGAGTATAG  GTACTTATTC    300

TATTAGTAAC  TCTATGCTTG  TTTTAAGGTA  CCGATACTCG  TACGTCGATC  GTGGGGGGTG    360

TAAGCCACGT  GGTCCACAGT  CTGACGAAGT  TTCGAACCCT  TCAGGGATTA  TTAACAAGGT    420
```

| | | | | | | |
|---|---|---|---|---|---|---|
| AATACGGAGT | AAAGGAGTAG | TATCATAGCT | TGGAATATGT | GGAAACCCCG | AGGAGGCAAT | 480 |
| CCCCTTGGCT | GTCAGATTAC | CTTACAAGTC | TCCATCTACT | GACCACGAAC | TGAACTCAGT | 540 |
| TCCTTCAGTC | GCTTACTATT | TACTGGAACA | TCTCCTCGAA | TTTGGAAAAA | GAAAAAAGCA | 600 |
| CCAACAAAAA | CTCAGGAGAT | CCACTCTTTA | TCGGACACAA | ATAGCTACTT | GCTTTCTGTG | 660 |
| CCGTGCAACG | ATACTGTCGG | AAAGCTCGAC | CTACGAGCCA | CTTACACCTG | TGGTAGCAGC | 720 |
| ACAAAGCCGG | ACTCGCCACA | ACTCAGCAAC | TAGCCATTCG | AAATCGCAAA | CTACAGCAGC | 780 |
| TACACGAACT | TCATGAGATG | GATTGTACAT | ACTGACTACA | CTAGGTTTAC | TAACAGATAG | 840 |
| ACAACCATTG | CCAGATTATA | GAGCCTTTTG | CTTTCTTGGT | CAACATGGGC | GCCATCGGGC | 900 |
| AAGACATGGC | ATATGATCGC | CTTGCCAACC | CGTCTCGGGC | GAGTTCCATC | TCTTCGAACC | 960 |
| GATACTCCGA | ACCTGTCGAG | CAATCCTTTG | CCCAGGGCAG | ACTGTGGTTC | CTGCACCAGC | 1020 |
| TGAAGCTCGG | TGCGAGCTGG | GACATTACGC | CGGCCGCGAT | CCGACTTCGG | GGCCATCTCG | 1080 |
| ACATCGATGC | GCTGAACGCT | GCCTCGCGCG | CTCTGACGCA | GCGCCACGAG | ACGCTCCGAA | 1140 |
| CGACGTTCAA | GGAGCAGGAT | GGCGTGGGCG | TACAGGTTGT | GCACGCCTCG | GGCCTCGAAA | 1200 |
| GAGGGTTGAG | GATTGTTGAT | GCCTCGAGCC | GCGATTTGGC | CCAGCTCCTG | GCAGAGGAAC | 1260 |
| AAACCATGAA | GTTCGACCTA | GAGTCTGAGC | CAGCTTGGAG | AGTTGCATTG | TTGAAGGTGG | 1320 |
| CCGAGGATCA | CCATATTCTT | TCCATTGTTG | TACACCATAT | CATCTCAGAC | AGCCGGTCTC | 1380 |
| TCGACATTAT | TCAGCAGGAG | CTTGGAGAAC | TCTACACGGC | CGCCTCGCAG | GGGAAATCGA | 1440 |
| TTTCGGCTTG | TCCCTTGGGT | CCAATTCCCA | TTCAATACCG | TGACTTGACG | ACTTGGCAGA | 1500 |
| ACCAGGACGA | GCAGGTCGCT | GAGCAGGAAA | GGCAGCTCGG | ATACTGGATC | GAGCAGCTCG | 1560 |
| ATAACAACAC | ACCGGCCGAG | CTCCTCACAG | AGCTTCCCCG | GCCAGCTATC | CCATCTGGCG | 1620 |
| AAACTGGCAA | GATCTCCTTC | CAGATCGATG | GATCGGTACA | CAAAGAACTC | CTGGCCTTCT | 1680 |
| GCCGCTCCCA | GCAAGTAACC | GCCTACGCCG | TGCTGCTGGC | AGCGTTTCGC | GTGGCGCACT | 1740 |
| TTCGCCTCAC | TGGAGCCGAG | GATGCAACCA | TCGGAGCGCC | CGTTGCCAAC | CGCGACCGGC | 1800 |
| CGGAGCTGGA | GAACATGGTG | GCTCCCTTGG | CCACTCTGCA | GTGCATGCGA | GTCGTGCTCG | 1860 |
| ACGAGGACGA | CACCTTCGAG | TCGGTGCTGC | GGCAGATCAT | GTCCGTCATG | ACAGAGGCAC | 1920 |
| ATGCCAACCG | CGACGTCCCC | TTTGAGCGCA | TCGTGTCTGC | GTTGCTGCCC | GGGTCGACAG | 1980 |
| ACACATCACG | ACACCCGCTT | GTGCAGCTCA | TGTTTGCTTT | GCATCCCGCG | CAGGATACGG | 2040 |
| GCCGAGCCCG | GTGGGGGTTC | CTCGAGGCTG | AGACTCTGCA | GAGTGCGGCC | CCGACACGAT | 2100 |
| TCGACATGGA | GATGCACCTG | TTTGAGGGAG | ACGACCGGTT | CGATGCAAAC | GTGCTGTTCT | 2160 |
| CCACGGGCCT | TTTCGACGCA | GAGGCCATCC | GCAGCGTGGT | TTCTATCTTT | CGGGAAGTCC | 2220 |
| TGCGCCGTGG | CATCTCGGAG | CCTGCGGTGC | ATGTGAAGAC | GATGCCGCTC | ACCGATGGGC | 2280 |
| TCGCCGCGAT | CCGGGACATG | GGCTTGCTGG | ATATCGGGAC | CACCGACTAC | CCCCGCGAGG | 2340 |
| CGAGCGTGGT | TGATATGTTC | CAAGAGCAGG | TGGCCTTGAA | TCCAAGCGCC | ACCGCCGTGG | 2400 |
| CCGATGCTTC | GTCCAGATTG | AGCTACTCTG | AGTTGGATCA | CAAGTCAGAT | CAGCTGGCCG | 2460 |
| CGTGGCTGCG | CAGACGGCAG | CTCAAGCCCG | AGACCTTGAT | TGGCGTGTTG | TCTCCTCCGT | 2520 |
| CTTGCGAGAC | CATGGTTTCC | TTCCTCGGTA | TCCTCAAGGC | TCATCTGGCT | TATCTGCCTC | 2580 |
| TCGATATCAA | CGTTCCCTTG | GCACGCATCG | AATCAATCCT | TTCGGCCGTG | GACGGGCACA | 2640 |
| AGCTCGTCCT | GCTTGGGAGC | AACGTGCCCC | AACCCAAGGT | GGATGTACCC | GATGTTGAGT | 2700 |
| TGCTGCGGAT | CAGCGATGCC | CTGAACGGGT | CTCAGGTGAA | TGGGCTTGCA | GGGAAACAGG | 2760 |
| CGACTGCAAA | GCCCTCGGCG | ACGGACCTGG | CCTACGTCAT | CTTCACCTCG | GGATCGACTG | 2820 |

```
GCAAGCCGAA GGGTGTCATG ATCGAGCATC GGGGCATCGT ACGCCTCGTG AAAGGAACAA    2880
ACATTATTTC GCCCGCCCAG GCAGCAGTGC CGACAGCTCA CCTGGCCAAC ATCGCTTTCG    2940
ACCTCTCAAC ATGGAGATC  TATACCCCTA TCCTTAATGG CGGCACTCTT GTCTGTATCG    3000
AACACTCTGT CACGCTAGAT AGCAAGGCAC TAGAAGCTGT ATTCACCAAG GAGGGCATTC    3060
GTGTGGCCTT CCTTGCTCCT GCTCTGATCA AGCAGTGTCT CGCCGACAGA CCGGCGATCT    3120
TTGCGGGCCT GGATAGCCTG TACGCTATTG GCGATCGCTT CGACCGACGT GACGCCCTCC    3180
ATGCAAAGTC CTTGGTGAAG CATGGCGTTT ATAATGCCTA TGGTCCAACC GAGAATTCCG    3240
TCGTCAGTAC CATCTACAGC GTCTCCGAGG CTTCACCGTT TGTCACGGGG GTGCCCGTTG    3300
GCCGGGCCAT CAGCAACTCG GGCGCCTATG TAATGGATCA GGATCAGCAA TTGGTCTCTC    3360
CCGGGGTGAT GGGGGAGCTT GTGGTTTCTG GAGATGGCCT AGCTCGAGGA TATACCGATT    3420
CGGCTCTGGA TAAGAACCGA TTTGTCGTGG TGCAGATTGA CGGCGAGTCA ATCCGGGGCT    3480
ATCGTACGGG AGACCGGGCC CGATACAGCC TCAAGGGTGG CCAGATTGAG TTCTTTGGCC    3540
GCATGGATCA GCAGGTCAAG ATCCGTGGCC ATCGTATCGA GCCAGCCGAG GTAGAGCACG    3600
CTTTACTCAA CAGCGACCAA GTACGCGATG CAGCAGTGGT TATCCGGAGA CAGGAGGAGG    3660
AAGAGCCTGC GATGATTGCC TTCGTTACGA CGCAGGGTAC GCTCCCTGAT CACCTCGTCA    3720
ACATCAACGG CAACGGCCAC GTTCCCGACG GCAACGGCAG CAAGAACGAC CAATTCGCCG    3780
TTCACGTCGA GAGCGAACTG CGCCGGCGCT TGCAGATGTT GCTGCCCTCC TACATGATGC    3840
CGGCCCGCAT CGTGGTGCTT GACCATCTCC CTCTCAACCC CAACGGCAAA GTCGACCGGA    3900
AGGCGCTGGG TCAGTCGGCC AAGACTGTGC AGAAGAGCAA GCTGGTCTCA CAGCGCGTCG    3960
CCCCACGCAA TGAGATCGAG GCCGTGCTTT GCGAGGAGTA CAGGAGTGTG CTTGGTGTCG    4020
AGGTTGGCAT CACCGATAAC TTCTTCGACC TGGGTGGTCA TTCCTTGACG GCCATGAAGC    4080
TCGCGGCACG GATCAGCCAG AGGCTCGACA TTCAAGCATC CGTAGCAACT GTCTTTGAGC    4140
AGCCGATGCT CGCTGACCTC GCCGCCACGA TCCAGCGCGG CTCGACTCTG TATAGCGTCA    4200
TCCCTACGAC AGAATACACG GGACCGGTGG AGCAATCATT TGCCCAAGGC CGTCTGTGGT    4260
TCCTTGAGCA GCTGAATACC GGCGCCTCAT GGTATAATGT GATGCTCACC GTACGACTAC    4320
GAGGCCACCT CGACGTGGAT GCGCTGGGAA CGGCCCTGCT CGCCCTGGAG AAACGGCACG    4380
AGACTCTTCG GACAACCTTT GAGGAACGGG ACGGGGTTGG CATGCAGGTA GTCCACAGCA    4440
GCCTCATGGG GGAGCTGCGG CTGATTGATA TATCAGAGAA ATCTGGCACT GCCGCGCATG    4500
AGGCACTGAT GAAGGAGCAG TCAACCCGCT TCGACCTGAC TCGCGAGCCA GGTTGGAGAG    4560
TGGCGCTGCT GAAGTTGGCA GACCACCACA TCTTCTCGAT CGTCATGCAC CACATTGTAT    4620
CGGATGGATG GTCTCTCGAC CTCCTACGAC ACGAGCTGGG CCAACTCTAC TCGGCAGCTC    4680
TGCGCGGCCA GGACCCATTG TCGCGCCTTG AGCCACTCCC GATCCAATAC CGCGACTTTG    4740
CGGTCTGGCA GAAGCAAGAC AGCCAGCAGA AAGCAGCGCA CCAGAGGCAA TTGGAGTACT    4800
GGACCAAGCA GCTTGCAGAC AGCACGCCTG CAGAGCTCTT GACAGACTTC CCGCGGCCCT    4860
CGATTCTATC CGGAAAGGCT GGAAAGGTCC CCGTTGCCAT CGAGGGTCT  CTATACGACA    4920
CGCTTCAAGT CTTCAGCCGC ACCCATCAAG TCACGTCGTT TGCTGTCCTA CTCGCAGCCT    4980
TCCGTGCAGC ACATTTCCGG CTTACGGGAT CTGATAATGC GACTATTGGT GTCCCCAGCG    5040
CGAACCGGAA TCGACCTGAG CTTGAGAACG TGATCGGCTT CTTCGTGAAC ACACAATGTA    5100
TACGTATCAC GATCGATGAA AACGATAACT TTGAATCGTT GGTCCGGCAG GTCCGGTCGA    5160
CGACTACAGC CGCACAGGAC AATCAGGATG TCCCGTTCGA ACAGGTCGTT TCCAGCCTCA    5220
```

```
TGCCGAGCAG CTCGAGAGAT GCATCCCGGA ACCCTCTGGT GCAGCTCATG TTTGCACTGC   5280
ACGGCCAGCA GGATCTGTTC AAGATCCAAC TGGAAGGGAC CGAAGAGGAG GTGATCCCAA   5340
CAGAAGAAGT GACGAGGTTC GACATCGAGT TCCATCTCTA CCAAGGCGCC AGCAAGCTGA   5400
GCGGTGATAT CATATTCGCT GCCGACTTAT TCGAAGCCGA AACTATTCGT GGCGTCGTCA   5460
GCGTCTTTCA GGAGGTTCTG AGGCGCGGAT GCAACAGCC  GCAGACCCCG ATCATGACAA   5520
TGCCACTCAC CGACGGCATT CCAGAGTTGG AGAGGATGGG CTTGTTGCAC ATGGTCAAGA   5580
CCGACTACCC CCGCAACATG TCTGTGGTAG ACGTATTCCA ACAACAAGTT CGTCTCAGCG   5640
CCGAGGCTAC AGCTGTTATC GACTCATCTT CGCGGATGAG TTACGCCGAA CTGGACCAGA   5700
GGTCCGATCA GGTGGCAGCG TGGCTTCGCC AGCGACAACT GCCAGCCGAA ACCTTTGTGG   5760
CAGTGCTCGC ACCACGCTCG TGCGAGGCCG TCATTGCTCT CTTCGGCATC TTGAAGGCTG   5820
GTCATGCCTA CCTACCGCTC GACGTCAATG TGCCAGCAGC GCGTCTTCGC GCCATCTTGG   5880
CCGAGGTGAA GGGCGAGAAG CTGGTTCTCC TAGGAGCAGG TGAGCCATCA CCGGAAGGCC   5940
AGTCGCCAGA GGTCTCGATC GTGAGGATTG CCGATGCCAC GAGCCCTGCT GGCCATGCCA   6000
GCTTGCGTGA TGGCAAGTCC AAGCCAACCG CAGGCAGCCT CGCCTATGTC ATCTTCACTT   6060
CCGGATCCAC TGGTAAACCC AAGGGTGTGA TGATCGAGCA CCGCGGAGTC TTGCGCCTTG   6120
TGAAGCAGAC CAACATTCTA TCCAGTCTAC CGCCGGCGCA GACCTTCCGA ATGGCTCACA   6180
TGTCCAACCT TGCGTTCGAT GCATCGATAT GGGAGGTCTT CACGGCCCTT CTCAACGGAG   6240
GCTCTCTTGT ATGCATTGAC AGGTTTACCA TCTTGGATGC TCAAGCGTTG GAGGCACTAT   6300
TCCTCAGGGA GCACATCAAT ATTGCACTGT TCCCACCCGC CCTGTTAAG  CAATGCCTCA   6360
CGGATGCAGC TGCTACCATC AAGTCTCTTG ACCTCCTATA CGTAGGAGGA GACCGGTTAG   6420
ACACAGCGGA CGCAGCTCTG GCCAAAGCTC TGGTCAAGTC AGAGGTCTAC AATGCCTACG   6480
GCCCAACGGA AAATACGGTC ATGAGCACTT TATACTCGAT TGCTGACACA GAACGATTTG   6540
TTAATGGTGT GCCAATTGGA AGAGCCGTTA GCAACTCTGG GGTCTACGTG ATGGACCAGA   6600
ATCAGCAGCT TGTGCCGTTG GGCGTGATGG GAGAGCTGGT AGTCACTGGA GATGGTTTGG   6660
CTCGTGGCTA CACCAACCCG GCTCTTGATT CCGACCGGTT CGTGGATGTC ATTGCTCGAG   6720
GCCAACTTCT CAGGGCCTAT CGCACAGGCG ACCGAGCTCG TTACCGGCCC AAGGATGGCC   6780
AGGTTGAGTT CTTTGGTCGG ATGGATCACC AGGTCAAGGT CCGAGGGCAC CGCATCGAGC   6840
TCGCCGAAGT AGAACACGCT TTGTTAAGCA GTGCCGGTGT GCACGATGCC GTTGTCGTTT   6900
CAAACTCGCA GGAAGACAAT CAGGGAGTCG AGATGGTGGC CTTCATCACC GCCCAAGACA   6960
ACGAGACTCT CCAGGAAGCA CAGTCGAGCA ACCAAGTCCA GGAATGGGAG AGCCATTTCG   7020
AGACCACGGC CTACGCGGAC ATCACGGCCA TTGATCAAAA CACGCTCGGC CGAGACTTTA   7080
CATCCTGGAC CTCTATGTAC GATGGAACGC TTATTGACAA GAGGGAGATG CAGGAATGGC   7140
TCGACGATAC TATGCGCACT TTCCTTGACG GTCAAGCAGC TGGCCACGTG CTTGAAATCG   7200
GTACCGGCAC CGGTATGGTT CTATTCAATC TCGGTCAAGC TGGGCTGAAG AGCTACATTG   7260
GACTGGAACC TTCCCAATCC GCGGTTCAAT TCGTCAACAA GGCAGCCCAA ACGTTCCCAG   7320
GGCTTGAGGG AAAGGCCCAA GTACATGTCG GCACGGCGAT GGATACGGGC CGGCTCAGCG   7380
CTTTGAGCCC GGATCTGATC GTCATCAACT CCGTGGCCCA GTATTTCCCG AGCCGAGAAT   7440
ACCTCGCCGA GGTGGTTGAG GCCCTGGTCC GGATTCCAGG CGTTCGCCGT ATCTTCTTCG   7500
GAGACATGAG AACCTATGCC ACCCACAAAG ACTTCCTTGT TGCACGGGCG GTCCACACAA   7560
ACGGGAGCAA GGTGACGAGA TCTAAAGTGC AACAGGAGGT GGCCCGGTTA GAGGAACTGG   7620
```

```
AGGAGGAATT  GCTTGTCGAC  CCTGCCTTCT  TCACAAGTCT  CAAGGAATCT  CTATCGGAAG   7680
AAATAGAGCA  TGTTGAGATC  CTGCCGAAGA  ACATGAAGGT  GAACAACGAG  CTCAGCTCAT   7740
ACCGGTACGG  CGCGGTTCTG  CACATCCGTA  ACCACAACCA  GAATCAAAGC  AGGTCGATTC   7800
ACAAGATCAA  TGCAGAGTCC  TGGATCGACT  TCGCCTCAAG  CCAGATGGAT  AGACAGGGTC   7860
TTGCTAGGCT  GTTGAAAGAG  AACAAAGATG  CCGAAAGTAT  CGCTGTGTTC  AACATCCCTT   7920
ACAGCAAGAC  TATCGTGGAA  CGGCACATCG  CCAAGTCTTT  GGCCGATGAC  CACGACGGCG   7980
ATGATACACA  TAGCTCAATC  GATGGAGTCG  CCTGGATCTC  AGCCGCGCGC  GAGAAGGCGA   8040
GCCAGTGTCC  ATCTCTTGAT  GTGCATGACC  TCGTGCAGTT  GGCCGAGGAC  GCTGGGTTCC   8100
GCGTCGAGGT  CAGCTGGGCC  CGCCAAAGGT  CCCAGAACGG  CGCTCTCGAT  GTTTCTTCC   8160
ATCACTTCCA  GCCTACCGAG  AACGAAAGCC  GCGCGCTCGT  CGATTTCCCC  ACCGACTACA   8220
AGGGCCAACA  AGCCAGAAGC  CTGACGAACC  GGCCCCTGCA  GCGGGTTGAG  AGCCGTCGAA   8280
TCGAAGCACA  GGTCCGAGAG  CAGCTCCAAG  TATTGCTCCC  GGCATACATG  ATCCCAGCCC   8340
GGATTGTGGT  TCTCCAGAAC  ATGCCGCTGA  ACACGAGCGG  CAAGGTAGAT  CGCAAGGAGC   8400
TCACCCTTCG  AGCCAAGGTC  ACCGCCGCAC  GTACGCCGAG  CTCCGAACTC  GTGGCTCCTC   8460
GTGATTCTAT  TGAAGCCATC  ATCTGCAAGG  AATTCAAGGA  TGTTCTCGGC  GTCGAAGTGG   8520
GTATTACAGA  CAACTTCTTT  AATGTCGGAG  GACACTCTCT  TTTGGCCACG  AAGCTCGCAG   8580
CACGCCTGAG  CCGACAACTC  AATGCCCAGA  TCGCAGTCAA  AGACATCTTC  GACCGGCCAG   8640
TTATCGCCGA  TCTGGCAGCC  ACAATCCAGC  AGGATACCAC  GGAGCACAAC  CCTATCCTAC   8700
CGACTTCTTA  TACGGGTCCA  GTCGAACAAT  CGTTCGCCCA  AGGCCGACTC  TGGTTCCTCG   8760
ATCAACTGAA  TGTCGGCGCC  ACATGGTATC  TCATGCCCTT  CGCAGTCCGG  CTGCGAGGGC   8820
CTTTGGTTGT  TTCTGCTCTC  GCTGCCGCTC  TTCTGGCCCT  AGAGGAGCGC  CACGAGACAC   8880
TGCGAACAAC  CTTTATCGAA  CAGGAAGGCA  TCGGCATGCA  GGTCATCCAT  CCGTTTGCCC   8940
CTAAGGAACT  GAGGGTGATC  GATGTCTCGG  GCGAGGAAGA  GAGCACTATC  CAGAAGATAC   9000
TGGAAAAGGA  ACAGACAACA  CCCTTCAATC  TCGCTTCCGA  GCCCGGTTTC  AGACTAGCAT   9060
TACTGAAGAC  AGGAGAGGAC  GAACACATTC  TCTCGACAGT  AATGCACCAT  GCAATCTCTG   9120
ATGGCTGGTC  TGTCGATATC  TTCCAACAAG  AAATCGGCCA  ATTCTACTCG  GCAATCCTCC   9180
GCGGACACGA  TCCTTTGGCC  CAGATCGCAC  CGCTCTCGAT  CCAGTATCGC  GATTTCGCGA   9240
CTTGGCAGAG  GCAGATATTC  CAAGTCGCAG  AGCACCGGCG  GCAGCTTGCA  TACTGGACTA   9300
AACAGCTTGC  CGATAATAAA  CCAGCCGAGC  TGCTGACCGA  TTTCAAGCGA  CCGCCTATGC   9360
TCTCCGGCCG  CGCGGGCGAG  ATCCCGGTGG  TCGTCGACGG  CTTGATCTAT  GAGAAGCTTC   9420
AGGACTTCTG  TCGAATCCGC  CAGGTGACCG  CCTTTACCGT  GTTGCTGGCT  GCTTTCCGCG   9480
CAGCGCACTA  TCGTATGACC  GGGACTGAGG  ATGCGACGAT  TGGAACACCT  ATCGCGAACC   9540
GTAACCGGCC  GGAGCTTGAG  GGCTTGATCG  GCTTCTTCGT  CAACACACAG  TGCATGCGTA   9600
TCACCGTCGA  TGTAGAGGAT  TCGTTCGAAA  CGTTGGTTCA  CCAGGTTCGA  GAAACGACGC   9660
TGGCTGCACA  TGCCAACCAG  GATGTTCCTT  TCGAACAGAT  TGTCTCAAAC  ATCTTGCCCG   9720
GATCGAGCGA  CACTTCTCGG  AATCCGCTGG  TACAGCTCAT  GTTTGCTCTA  CATTCGCAGC   9780
AGAACCTTGG  CAAGGTCCGC  CTCGAGGGTA  TCGAGGAGGA  GATCATCTCC  ATTGCTGAGA   9840
CCACGAGATT  TGATATCGAG  TTCCATCTGT  ACCAAGAGGC  TGAGAGGCTG  AACGGTAGTA   9900
TCGTCTATGC  AGCTGATCTC  TTCGTGCCCG  AGACTATACA  GAGCGTCATC  ACCATCTTCC   9960
AAGGCATCCT  ACAGAAAGGC  CTCGGCGAGC  CGGATATGCC  CGTCGCCTCT  ATGGCGCTTG   10020
```

```
ATGGTGGGCT GGAGTCCCTC CGAAGCACAG GACTGCTGCA CCCTCAACAA ACTGATTATC    10080
CGTGCGATGC TTCAGTGGTG CAGATCTTCA AACAGCAGGT GGCAGTCAAC CCGGATGTCA    10140
TCGCGGTGAG AGATGAATCA ACACGGCTGA GCTATGCCGA CTTGGATCGG AAGTCGGATC    10200
AAGTGGCTTG CTGGCTATCT CGGCGAGGTA TCGCTCCTGA GACGTTCGTG GCGATCCTGG    10260
CACCACGCTC GTGCGAGACA ATCGTGGCCA TCCTCGGTGT GTTGAAGGCC AACCTTGCAT    10320
ATCTGCCTCT TGATGTCAAT GTTCCTGCGT CCCGGCTCGA GGCCATCCTT TCGGAGGTGT    10380
CGGGATCGAT GTTGGTCCTT GTGGGCGCAG AGACCCCGAT TCCGGAGGGG ATGGCTGAAG    10440
CGGAGACGAT CCGGATCACG GAGATTCTCG CCGACGCAAA GACCGACGAC ATCAACGGGC    10500
TGGCCGCGAG TCAGCCCACT GCAGCAAGCC TTGCGTATGT GATCTTTACG TCTGGATCGA    10560
CTGGTCGACC AAAGGGCGTC ATGGTCGAGC ATCGCGGAAT CGTTCGTCTT ACAAAGCAGA    10620
CCAACATCAC ATCCAAGCTG CCAGAGTCTT TCCACATGGC CCACATATCG AATCTTGCCT    10680
TCGATGCCTC CGTGTGGGAA GTGTTCACGA CGCTTCTCAA TGGAGGCACG TTGGTGTGTA    10740
TCGACTATTT CACTCTCTTG GAGAGCACAG CGCTCGAGAA GGTCTTCTTC GACCAACGCG    10800
TCAATGTTGC TCTGCTCCCT CCAGCCTTGC TGAAACAGTG CCTTGACAAC TCACCCGCTC    10860
TGGTCAAAAC TCTCAGCGTT CTCTATATTG GTGGTGATAG CTAGATGCT TCTGATGCTG    10920
CCAAAGCAAG GGGGCTCGTC CAGACGCAAG CTTTCAATGC GTACGGCCCA ACGGAAAACA    10980
CAGTCATGAG CACAATCTAT CCCATTGCCG AAGACCCTT CATCAATGGT GTGCCCATCG     11040
GTCATGCTGT CAGTAACTCG GGAGCTTTTG TCATGGACCA GAATCAGCAA ATCACCCCCC    11100
CTGGTGCAAT GGGAGAACTC ATCGTGACTG GAGACGGTCT TGCTCGAGGC TACACTACTT    11160
CCTCTCTCAA CACTGGTCGA TTTATCAACG TTGATATCGA TGGCGAGCAA GTCAGGGCAT    11220
ACCGCACAGG AGATCGAGTG CGCTACCGAC CAAAAGACCT CCAGATCGAA TTCTTCGGCC    11280
GTATCGATCA CCAGGTCAAG ATCCGCGGCC ACCGCATCGA ACCAGCTGAG GTCGAGTATG    11340
CTCTTCTAAG CCACGACCTG GTCACTGATG CGGCAGTCGT CACCCACTCT CAAGAAAATC    11400
AAGACCTGGA GATGGTTGGA TTCGTGGCCG CCCGAGTCGC TGATGTTAGA GAGGATGAGT    11460
CCAGCAACCA GGTCCAAGAA TGGCAGACTC ACTTCGACAG CATCGCATAC GCAGATATCA    11520
CCACAATCGA TCAGCAAAGC CTTGGACGGG ACTTCATGTC ATGGACCTCC ATGTACGATG    11580
GCAGCCTGAT CAAGAAGAGC CAGATGCAGG AGTGGCTCGA TGACACCATG CGGTCACTCC    11640
TGGATTCCCA GCCCCCTGGT CACGTACTCG AAGTTGGTAC AGGGACTGGC ATGGTTCTGT    11700
TCAACCTCGG CAGAGAAGGG GGTCTGCAAA GCTACGTTGG CCTAGAGCCA TCGCCATCCG    11760
CAACCGCGTT TGTCAACAAG GCCGCCAAGT CATTCCCTGG GCTTGAGGAT AGGATCCGGG    11820
TTGAAGTTGG AACAGCAACT GATATCGACC GGCTTGGAGA CGATCTGCAC GCAGGTCTTG    11880
TCGTCGTCAA CTCGGTCGCT CAATACTTCC CGAGTCAAGA CTATCTCGCC CAGTTGGTCA    11940
GAGATCTTAC CAAGGTCCCT GGCGTGGAGC GTATCTTCTT TGGTGATATG AGGTCGCACG    12000
CCATCAACAG GGATTTCCTT GTCGCTCGCG CAGTTCATGC ACTGGGCGAT AAGGCAACAA    12060
AGGCCGAGAT TCAACGGGAG GTTGTTCGAA TGGAAGAGTC TGAAGACGAA CTGCTCGTTG    12120
ATCCGGCCTT TTTCACCTCC CTGACGACGC AAGTAGAGAA TATCAAGCAC GTGGAGATTC    12180
TCCCCAAGAG AATGCGAGCC ACGAACGAGC TGAGCTCGTA TCGGTATGCT GCTGTTCTGC    12240
ACGTCAATGA TCTGGCGAAA CCGGCACACA AAGTCAGTCC TGGCGCCTGG GTTGATTTTG    12300
CCGCGACGAA GATGGATCGC GATGCCCTGA TCCGTCTGCT CAGGGGCACC AAAATTTCCG    12360
ACCACATTGC AATCGCCAAT ATTCCCAACA GCAAGACAAT CGTCGAGCGA ACCATCTGCG    12420
```

| | | | | | | |
|---|---|---|---|---|---|---|
| AATCGGTTTA | CGACCTTGGC | GGAGACGCCA | AAGACTCGAA | CGACAGAGTC | TCATGGCTTT | 12480 |
| CGGCTGCTCG | ATCGAATGCC | GTGAAAGTGG | CTTCCCTCTC | CGCGATCGAT | CTCGTTGATA | 12540 |
| TTGCACAAGA | GGCAGGCTTC | CGGGTCGAGA | TCAGCTGCGC | GCGGCAGTGG | TCTCAGAATG | 12600 |
| GCGCGTTGGA | CGCCGTATTC | CACCACCTTG | GCCCATCACC | ACAGTCGTCT | CATGTGTTGA | 12660 |
| TTGACTTCTT | GACCGACCAC | CAAGGTCGAC | CAGAAGAAGC | CCTGACGAAC | CACCCGCTGC | 12720 |
| ACCGAGCACA | GTCTCGACGC | GTCGAGAGGC | AGATCCGCGA | GAGACTCCAG | ACTCTCCTGC | 12780 |
| CGGCCTACAT | GATCCCGGCC | CAGATCATGG | TTCTTGACAA | GCTACCTCTC | AACGCGAATG | 12840 |
| GAAAGGTCGA | CCGGAAGCAG | TTGACGCAAC | GGGCCCAGAC | GGTACCCAAG | GCCAAGCAAG | 12900 |
| TGTCTGCTCC | TGTGGCCCCG | CGCACAGAGA | TCGAAAGGGT | GCTCTGCCAG | GAGTTCTCCG | 12960 |
| ACGTCCTAGG | GGTTGATATC | GGGATAATGG | AAAACTTCTT | CGATCTCGGT | GGCCACTCGC | 13020 |
| TCATGGCAAC | AAAGCTAGCC | GCACGCATCA | GCCGCCGACT | AGAGACTCAC | GTCTCCGTCA | 13080 |
| AGGAGATCTT | TGACCATCCG | CGAGTCTGCG | ATCTTGTTCT | CATAGTACAG | CAGGGATCAG | 13140 |
| CGCCTCATGA | CCCCATCGTT | TCGACCAAAT | ACACCGGGCC | AGTGCCTCAG | TCGTTTGCCC | 13200 |
| AGGGTCGTCT | TTGGTTCCTC | GACCAGCTCA | ACTTTGGCGC | AACATGGTAT | CTCATGCCCC | 13260 |
| TTGCCGTCCG | TCTTCGCGGT | GCCATGAACG | TTCATGCTCT | TACCGCGGCC | TTGTTGGCCC | 13320 |
| TCGAGAGGCG | TCACGAGCTC | CTCCGCACCA | CGTTCTACGA | ACAAAACGGC | GTCGGTATGC | 13380 |
| AAAAGGTCAA | TCCAGTTGTC | ACCGAGACCC | TGAGGATCAT | TGATCTCTCC | AACGGCGACG | 13440 |
| GCGACTATCT | CCCGACATTG | AAGAAGGAGC | AAACTGCTCC | GTTCCACCTG | GAAACCGAGC | 13500 |
| CCGGATGGCG | CGTGGCTCTA | CTGCGCCTCG | GGCCAGGCGA | CTACATCTTA | TCTGTCGTCA | 13560 |
| TGCATCACAT | CATTTCCGAC | GGCTGGTCTG | TGGATGTTCT | CTTCCAAGAG | CTGGGCCAGT | 13620 |
| TCTATTCCAC | GGCTGTCAAA | GGCCACGATC | CCCTATCGCA | GACCACACCC | CTCCCGATCC | 13680 |
| ATTATCGCGA | TTTTGCTCTG | TGGCAGAAGA | AGCCAACCCA | AGAAAGCGAA | CACGAGCGTC | 13740 |
| AGCTGCAATA | CTGGGTCGAG | CAACTTGTAG | ATAGTGCCCC | GGCCGAGCTA | CTCACGGATC | 13800 |
| TGCCGCGGCC | TTCGATCCTC | TCTGGTCAGG | CTGGGGAGAT | GTCGGTCACG | ATCGAGGGAG | 13860 |
| CACTATACAA | GAACTTGGAG | GAATTCTGCC | GGGTCCATCG | CGTTACCTCC | TTCGTGGTAC | 13920 |
| TGCTTGCGGC | CCTACGCGCA | GCCCATTATC | GCCTCACAGG | TTCCGAAGAC | GCAACTATAG | 13980 |
| GGACACCAAT | CGCCAATCGT | AACCGACCTG | AACTTGAGCA | GATAATCGGC | TTCTTCGTCA | 14040 |
| ATACGCAATG | TATACGCATT | ACCGTCAACG | AGGACGAGAC | CTTTGAGTCA | CTAGTGCAGC | 14100 |
| AGGTCCGGTC | AACGGCGACA | GCTGCATTCG | CCCATCAGGA | CGTCCCGTTC | GAGAAGATCG | 14160 |
| TCTCTACTCT | TTTGCCCGGT | TCTCGAGATG | CATCCCGAAA | CCCACTTGTG | CAGCTCATGT | 14220 |
| TTGCGGTGCA | TTCGCAGAAG | AACCTCGGTG | AGCTGAAGCT | GGAAAACGCT | CACAGCGAGG | 14280 |
| TTGTTCCCAC | GGAGATCACG | ACCCGGTTCG | ATTTGGAATT | CCACCTGTTC | CAGCAAGATG | 14340 |
| ACAAGCTTGA | GGGCTCCATC | CTCTATTCAA | CCGATCTCTT | CGAAGCAGTC | TCGGTCCAAA | 14400 |
| GTCTTCTTTC | AGTATTCCAG | GAAATTCTGC | GCCGGGGTTT | GAACGGTCCG | ACGTGCCCA | 14460 |
| TCAGCACCCT | ACCACTTCAG | GATGGAATCG | TCGACCTACA | AAGACAGGGC | CTGTTGGATG | 14520 |
| TCCAGAAGAC | GGAATATCCT | CGTGATTCCT | CTGTGGTTGA | TGTGTTCCAT | GAGCAGGTCT | 14580 |
| CGATCAACCC | CGATTCCATT | GCACTGATAC | ATGGCTCGGA | GAAGCTCAGC | TACGCCCAGC | 14640 |
| TCGACAGGGA | ATCTGACAGG | GTCGCTCGCT | GGCTCCGTCA | CCGTTCTTTC | AGCTCCGACA | 14700 |
| CGTTAATCGC | GGTGTTGGCG | CCACGGTCTT | GCGAGACGAT | CATCGCGTTC | CTCGGAATCC | 14760 |
| TCAAGGCAAA | CCTTGCGTAC | CTACCTCTGG | ATGTCAAGGC | TCCTGCTGCC | CGCATTGATG | 14820 |

| | | | | | | |
|---|---|---|---|---|---|---|
| CCATTGTATC | GTCGCTACCC | GGGAACAAGC | TCATCCTGCT | GGGCGCAAAC | GTTACGCCGC | 14880 |
| CCAAGCTTCA | GGAAGCGGCC | ATCGATTTCG | TGCCCATCCG | TGATACCTTC | ACTACACTCA | 14940 |
| CTGACGGCAC | ACTTCAAGAT | GGGCCTACCA | TCGAGCGACC | CTCTGCGCAA | AGCCTAGCGT | 15000 |
| ACGCCATGTT | CACGTCTGGT | TCTACCGGAC | GACCGAAGGG | TGTTATGGTC | CAGCACCGCA | 15060 |
| ACATCGTCCG | CTTGGTGAAG | AACAGTAACG | TCGTCGCTAA | GCAGCCCGCA | GCAGCTCGCA | 15120 |
| TAGCACATAT | ATCCAATTTG | GCGTTTGACG | CCTCGTCTTG | GGAGATCTAT | GCCCCGCTGC | 15180 |
| TCAACGGCGG | CGCAATTGTG | TGTGCCGACT | ACTTCACAAC | GATTGATCCA | CAGGCTCTTC | 15240 |
| AAGAAACCTT | CCAGGAACAC | GAGATCCGCG | GTGCTATGCT | GCCGCCCTCG | CTCCTCAAGC | 15300 |
| AGTGCCTGGT | TCAGGCCCCA | GACATGATCA | GCAGGCTTGA | CATCTTATTT | GCTGCTGGTG | 15360 |
| ATCGCTTCAG | TAGCGTGGAT | GCTCTCCAGG | CCCAACGTCT | CGTTGGCTCG | GGCGTCTTCA | 15420 |
| ATGCGTATGG | CCCTACGGAG | AATACGATTC | TGAGCACTAT | CTATAACGTT | GCTGAAAACG | 15480 |
| ACTCCTTCGT | TAACGGCGTT | CCCATAGGCA | GTGCTGTGAG | CAACTCCGGA | GCCTACATCA | 15540 |
| TGGATAAGAA | CCAGCAGCTC | GTGCCAGCTG | GAGTTATGGG | AGAACTGGTT | GTTACTGGTG | 15600 |
| ACGGTCTCGC | CCGCGGCTAT | ATGGATCCAA | AGCTAGATGC | AGACCGCTTT | ATCCAACTGA | 15660 |
| CAGTCAACGG | CAGCGAGCAA | GTCAGGGCAT | ATCGCACCGG | CGACCGTGTG | CGATACCGAC | 15720 |
| CAAAGGACTT | CCAGATCGAG | TTCTTCGGTC | GTATGGACCA | GCAAATCAAG | ATCCGCGGCC | 15780 |
| ACCGTATCGA | GCCGGCCGAG | GTAGAGCAGG | CCTTCCTGAA | TGATGGCTTC | GTCGAGGACG | 15840 |
| TTGCTATCGT | TATTCGGACC | CCAGAGAACC | AAGAGCCTGA | GATGGTCGCC | TTTGTTACTG | 15900 |
| CTAAGGGCGA | CAACTCCGCG | AGAGAAGAAG | AGGCTACAAC | CCAGATCGAA | GGTTGGGAGG | 15960 |
| CGCATTTCGA | GGGTGGTGCG | TACGCCAACA | TCGAGGAGAT | CGAAAGCGAG | GCGCTTGGTT | 16020 |
| ACGACTTTAT | GGGCTGGACG | TCTATGTACG | ATGGCACTGA | GATCGACAAG | GACGAGATGA | 16080 |
| GAGAGTGGCT | GAATGACACG | ATGCGCTCTC | TCCTCGATGG | AAAGCCGGCT | GGTCGAGTTC | 16140 |
| TTGAGGTCGG | TACCGGTACC | GGTATGATCA | TGTTTAACCT | TGGCAGGTCA | CAAGGGCTCG | 16200 |
| AAAGGTATAT | TGGCCTCGAA | CCTGCACCGT | CGGCAGCCGA | GTTCGTCAAC | AACGCTGCAA | 16260 |
| AGTCATTCCC | GGGTCTCGCG | GGCAGGGCCG | AAGTTCACGT | CGGCACCGCC | GCAGATGTCG | 16320 |
| GTACCCTGCA | AGGCCTGACC | TCAGATATGG | CCGTCATCAA | CTCGGTGGCG | CAGTACTTCC | 16380 |
| CAACGCCAGA | GTACCTGGCC | GAGACGATCA | AATCACTTGT | CCAAGTCCCG | GGCATGAAGC | 16440 |
| GCATATACCT | CGGCGATATG | CGGTCCTGGG | CCATGAACAG | GGACTTTGCT | GCCGCTCGCG | 16500 |
| CCGCCTATTC | ACTGGCCGAT | AATGCCAGCA | AGACCGCGT | GAGACAGAAG | ATGATGGAAT | 16560 |
| TGGAGGAGAA | GGAGGAAGAA | TTACTCGTTG | ACCCGGCCTT | CTTCACTGCC | TTGGCGAGCC | 16620 |
| AGCTGCAAGA | CAGGATCCAA | CACGTGGAGA | TCCTACCCAA | GCGAATGAAG | GCTACAAATG | 16680 |
| AGCTAAGCTC | GTACCGATAT | GCCGCCGTGC | TGCACATCTC | CGACGAGCCC | CTTCCTATCT | 16740 |
| ACAAGATTGA | TCCCGAAGCT | TGGATCAACT | TTGAGGGGTC | TCGATTGACC | CGAGAGGCGC | 16800 |
| TTGCACAAGT | ACTCAAGGAG | AATGAGAACG | CCGAGAGTGT | GGCCATCAGC | AACATTCCTT | 16860 |
| ATAGCAAGAC | CGTTGTAGAA | CGTCACATTG | TGCGGTCGCT | TGACCAGGAA | GACGCCAATG | 16920 |
| CCCCTGAGGA | ATCGATGGAT | GGCAGCGACT | GGATCTCGGC | CGTGCGCACA | AGAGCTCAGC | 16980 |
| AGTGCCACAC | TCTCTCCGCA | AGTGACCTGT | TCGACATTGC | AGAAGATGCT | GGGTTCCGTG | 17040 |
| TTGAGGTCAG | CTGGGCCCGT | CAACATTCGC | AGCACGGTGC | CCTGGATGCC | GTGTTCCACC | 17100 |
| ACCTGAAGCC | CGCTACGGAG | GACAGTCGCG | TTTTGATCAA | GTTCCCTACA | GATCACCAAG | 17160 |
| GCCGGCCGCT | CAAGAGCTTG | ACGAATCAAC | CGCTCCTGCC | AGCCCAGAGT | CGCCGAGCCG | 17220 |

```
AGCTCTTGAT  CCGCGAGGGG  CTGCAAACCC  TGCTGCCTCC  CTACATGATC  CCCTCGCAAA   17280
TCACGCTTAT  CGACCGGATG  CCACTCAATG  CTAACGGCAA  AGTCGACCGG  AGAGAACTCG   17340
CCCGTCGGGC  CAAAATCACA  CAGAAGAGCA  AGCCGGTTGA  GGACATCGTT  CCCCCTCGGA   17400
ACAGCGTCGA  GGCTACGGTC  TGCAAGGGCT  TCACTGACGT  GCTGGGCGTT  GAAGTTGGGA   17460
TAACAGACAA  TTTCTTCAAT  CTGGGCGGTC  ATTCACTGAT  GGCAACGAAG  TTGGCGGCGC   17520
GTCTAGGCCG  TCAACTCAAT  ACACGTATCT  CGGTGAGAGA  CGTCTTCGAT  CAACCAGTCG   17580
TTGCTGATCT  CGCCGCTGTG  ATCCAACGCA  ACTCGGCACC  TCACGAGCCG  ATCAAGCAG    17640
CAGACTACAC  AGGGCCCGTT  CCCCAGTCAT  TCGCACAGGG  CCGCCTTTGG  TTCCTCGATC   17700
AACTTAATGT  CGGGGCGACG  TGGTATCTTA  TGCCCCTTGG  TATCCGCCTT  CACGGATCTC   17760
TCCGGGTTGA  TGCCCTCGCT  ACCGCGATAT  CAGCCCTGGA  GCAACGTCAC  GAGCCTCTCC   17820
GTACGACATT  CCACGAGGAA  GATGGCGTCG  GTGTTCAAGT  CGTGCAAGAC  CACCGGCCCA   17880
AGGATCTGAG  AATCATCGAC  CTGTCCACTC  AGCCAAAGGA  CGCCTATCTT  GCCGTGTTGA   17940
AGCATGAGCA  GACCACGCTC  TTCGACCTCG  CAACCGAGCC  CGGTTGGCGC  GTCGCTCTGA   18000
TCAGGCTTGG  AGAAGAAGAG  CATATACTTT  CCATTGTTAT  GCACCATATC  ATATCTGACG   18060
GCTGGTCAGT  AGAGGTTCTG  TTTGATGAGA  TGCACCGGTT  CTACTCGAGT  GCGCTTAGGC   18120
AACAGGATCC  TATGGAGCAA  ATCTTGCCTC  TACCGATCCA  GTACCGCGAC  TTTGCAGCAT   18180
GGCAAAAGAC  TGAAGAGCAG  GTTGCCGAGC  ATCAGCGGCA  GTTGGACTAC  TGGACGGAGC   18240
ACCTTGCCGA  CAGTACCCCT  GCGGAGCTGT  TAACTGACCT  CCCTCGACCT  TCTATCTTGT   18300
CCGGCCGCGC  CAATGAGCTA  CCCCTTACCA  TCGAGGGGCG  TCTTCATGAT  AAATTGCGCG   18360
CTTTCTGCCG  AGTTCACCAA  GCCACGCCGT  TCGTCATTCT  CCTTGCGGCC  CTGAGGGCAG   18420
CACATTACCG  TCTTACAGGG  GCTGAAGATG  CCACGCTTGG  AACGCCAATT  GCTAACCGTA   18480
ACCGACCGGA  ACTTGAGAAC  ATGATCGGCT  TCTTTGTTAA  CACGCAGTGT  ATGCGTATTG   18540
CTATTGAGGA  GAATGATAAC  TTCGAGTCCC  TCGTCCGCCG  AGTACGATCG  ACTGCAACAT   18600
CCGCTTTCGC  GAACCAAGAC  GTTCCATTTG  AATCCATTGT  CTCGTCTCTT  CTGCCTGGAT   18660
CCAGGGACGC  CTCGCGCAAT  CCATTAGTGC  AGGTCATTCT  GGCTGTTCAC  TCTCAGCAGG   18720
ATTTGGGTAA  ACTCACCTTA  GAAGGCCTCA  GAGATGAAGC  TGTTGACTCG  GCTATCTCAA   18780
CCCGCTTCGA  TGTGGAGTTT  CATCTTTTCG  AGCACGCAGA  CAGGCTCAGC  GGTAGCGTGC   18840
TTTACGCAAA  GGAACTGTTC  AAGCTGCGCA  CGATCGAATC  AGTGGTCTCC  GTTTTCCTGG   18900
AGACTCTGCG  GCGGGCTCTC  GACCAGCCAC  TGACTCCTCT  CGCTGTCTTG  CCGCTGACTG   18960
ATGGAGTCGG  GGAGATCGCA  AGCAAGGGGC  TCCTTGATGT  GCCCAGGACA  GACTATCCAC   19020
GAGATGCAAA  TATCGTTGAG  GTCTTCCAAC  AGCACGTTCG  CGCTACCCCG  GACGCCATCG   19080
CCGTCAAGGA  CGCTACTTCC  ATACTGACGT  ATGCTCAGCT  AGATCAGCAG  TCTGATCGAC   19140
TTGCTATCTG  GTTGAGTCGC  CGGCACATGA  TGCCCGAAAC  GCTGGTGGGT  GTCCTTGCGC   19200
CGCGGTCATG  CGAGACCATT  ATCGCAATGT  TTGGCATTAT  GAAGGCCAAC  CTCGCCTACT   19260
TGCCTTTGGA  TATAAACTCG  CCTGCTGCTC  GACTCCGCAG  CATTCTCTCA  GCCGTAGATG   19320
GGAACAAGCT  TGTTTTGCTC  GGCAGTGGTG  TCACAGCCCC  CGAGCAAGAG  AACCCCGAGG   19380
TGGAAGCTGT  TGGTATTCAA  GAGATCTTGG  CCGGCACTGG  ACTGGACAAG  ACACAAGGCA   19440
GCAACGCCCG  ACCCTCGGCA  ACGAGCCTTG  CTTATGTTAT  CTTCACCTCT  GGTTCAACCG   19500
GCAAGCCCAA  GGGCGTCATG  GTCGAACATC  GTAGCGTTAC  GAGATTGGCA  AAGCCCAGCA   19560
ACGTTATCTC  CAAGCTACCA  CAAGGAGCCA  GGGTGGCGCA  CCTCGCCAAC  ATTGCCTTCG   19620
```

```
ATGCCTCGAT CTGGGAAATT GCCACAACTC TTCTGAATGG AGCCACGCTT GTTTGTCTCG    19680
ACTATCACAC CGTTCTCGAC TGCAGGACTC TCAAAGAAGT CTTCGAAAGG GAAAGCATTA    19740
CGGTTGTCAC ACTGATGCCT GCGCTCCTCA AGCAGTGCGT GGCCGAAATA CCCGAGACCC    19800
TCGCACACCT CGACCTCCTG TACACCGGTG GAGATCGAGT GGGTGGTCAC GATGCTATGC    19860
GGGCTCGCTC GCTAGTCAAG ATCGGCATGT TCAGCGGTTA CGGCCCTACG GAGAACACCG    19920
TCATCAGCAC CATCTACGAA GTTGATGCAG ACGAGATGTT TGTGAATGGT GTGCCTATCG    19980
GCAAGACTGT AAGCAACTCT GGGGCATATG TTATGGACAG GAATCAGCAG CTGGTGCCTA    20040
GTGGCGTGGT AGGTGAGCTT GTGGTCACTG GCGATGGCCT TGCTCGCGGA TACACTGATC    20100
CATCCCTAAA CAAGAACCGC TTCATTTACA TCACTGTCAA TGGAGAGAGT ATCAGGGCAT    20160
ATCGGACTGG CGATCGGGTG AGGTACCGGC CTCATGATCT GCAGATTGAA TTCTTTGGCC    20220
GCATGGACCA GCAGGTCAAG ATCCGTGGCC ATCGAATCGA GCCGGGAGAG GTGGAGAGCG    20280
CATTGCTCAG TCACAACTCG GTACAAGACG CCGCGGTCGT CATTTGCGCG CCAGCAGATC    20340
AAGACTCAGG CGCGGAAATG GTGGCATTCG TTGCCGCCCG GAATACCGAA GACGAAGACA    20400
CCCAGGAGGA AGAAGCAGTC GATCAGGTTC AAGGGTGGGA GACGCACTTC GAAACGGCCG    20460
CATATTCAGA AGTCAAGGAC ATTCGACAGT CAGAAGTCGG TAACGACTTC ATGGGCTGGA    20520
CTTCTATGTA TGACGGCAGC GAGATCGACA AGACAGATAT GCACGAGTGG CTCAACGACA    20580
CCATGCGTAT GATACTCGAC GCCAGAGAGC CGGGCCACGT ACTGGAGATC GGTACCGGCA    20640
CCGGCATGGT CATGTTCAAC CTTGCCAAGT GTCCTGGTCT GCAGGGCTAC GTCGGTTTCG    20700
AGCCTTCAAA GTCGGCAGCC CAATTCGTCA ATGATGCAGC CCAGTCATTC CCGGCTCTGA    20760
AGGATGGCCG GTCAATAGTC CATGTGGGCA CGGCGACAGA CATCAACAAG GCTGGGCCGA    20820
TTCAACCACG CCTCGTCGTT ATCAACTCAG TAGCGCAGTA TTTCCCCACG CCAGAGTACC    20880
TCTTCAGGGT TGTGGAGGCC CTTGTACAGA TCCCAAGCGT GGAACGCATC GTCTTTGGTG    20940
ACATGAGAAC CAACGCCATC AACAGAGACT TCGTCGCAAG CCGAGCATTG CACACCCTCG    21000
GCGAGAAGGC AAACAAGCGC CTGGTCCGCC AGATGATCTA TGAGCTCGAA GCCAACGAAG    21060
AGGAACTTCT GACGGACCCT GCATTCTTTA CATCTTTGCG TACGCGCTTG GGTGAGAAGA    21120
TCAAGCACGT CGAAATTCTC CCCAAGACCA TGAAGGCTAC CAACGAGCTC AGCAAGTACC    21180
GATATGCCGC AGTACTACAT GTGCGTGGCT CGAGAGAACA ATCAACTATA CACCAAGTCT    21240
CTCCCAACGC CTGGATAGAC TTTGCGGCAG ACGGTCTCGA CCGGCAGACC CTCATCAACT    21300
TGCTGAAGGA GCACAAGGAT GCCGGGACCG TCGCTATCGG TAATATCCCG TACAGCAAGA    21360
CCATTGTTGA GCGGTTTGTC AACAAGTCAC TGAGCGAGGA TGATATGGAG GAAGGCCAGA    21420
ACTCACTGGA CGGATCAGCT TGGGTTGCAG CCGTCCGGAT GGCCGCTCAA AGCTGCCCAT    21480
CACTCGATGC AATGGATGTC AAGGAGATTG CTCAGGAGGC GGGATACCAG GTCGAAGTCA    21540
GTTGGGCGCG TCAATGGTCC CAGAATGGTG CGCTCGATGC CATCTTCCAT CACTTCGAAC    21600
CGCCCAAGGA GGGTGCTCGC ACACTTATTG AGTTCCCGAC GGATTACGAA GGCCGGAATG    21660
TGAACACCTT AACGAACCGT CCCCTGAACA GCATTCAAAG CCGCCGTCTT GGGACGCAGA    21720
TCCGCGAGAA GCTGCAGACC CTCCTGCCGC CTTACATGAT CCCATCGCGC ATCATGGTCC    21780
TTGATCAGAT GCCTGTCAAC AACAACGGCA AGATTGACCG CAAGGAGCTT GTGCGGAGAG    21840
CTATCGTGGC CCCGAAGCCA AGGTCAGCGG CTACTCGGGT AGCCCCCGC AATGAGATCG    21900
AGGCTATTCT GAGAGACGAA TTCGAGGACG TGCTCGGAAC AGAAGTCAGC GTGCTGGATA    21960
ACTTCTTTGA TCTCGGCGGG CACTCACTTA TGGCCACGAA GCTCGCCGCC CGCGTTAGCC    22020
```

```
GCCGCCTTGA  TGCCCATATT  TCCATCAAAG  ATGTCTTTGA  TCAGCCGGTG  CTGGCGGATC   22080
TTGCGGCGTC  CATCCAGAGA  GAATCGGCTC  CTCATGAACC  GATTCCGCAA  AGGCCTTACA   22140
CCGGGCCGGC  TGAACAGTCA  TTTGCCCAAG  GTCGCCTATG  GTTCCTTGAC  CAGCTTAACC   22200
TTGGCGCGAC  CTGGTACCTG  ATGCCTTTAG  CCATCCGTAT  CCGTGGCCAG  TTGAGGGTAG   22260
CTGCGTTGTC  TGCCGCACTC  TTCGCCTTGG  AGAGACGACA  TGAGACCTTG  AGAACCACCT   22320
TTGAAGAAAG  CGACGGCGTT  GGCGTGCAAA  TTGTTGGAGA  GGCTCGCAAC  TCAGACCTTC   22380
GGGTTCATGA  CGTTTCTACC  GGAGACGACG  GGGAGTACCT  TGAGGTACTC  AGGAGGGAAC   22440
AGACTGTGCC  CTTCGACCTC  TCGTCAGAGC  CTGGCTGGAG  GGTTTGCCTG  GTCAAAACGG   22500
GCGAAGAGGA  TCATGTACTA  TCCATCGTCA  TGCACCATAT  TATTTACGAC  GGCTGGTCCG   22560
TGGACATTCT  CCGCGGAGAG  TTGGGTCAAT  TCTATTCCGC  TGCCCTACGC  GGCCAGGACC   22620
CCTTGCTGCA  CGCCAACCCC  CTTCCTATTC  AATACCGGGA  TTTCGCAGCG  TGGCAAAGGG   22680
AGGCAAAACA  GGTCGAAGAG  CATCAACGTC  AACTTGGGTA  CTGGTCGAAA  CAGCTCGTTG   22740
ACAGCACTCC  AGCTGAGCTC  TTGACGGATC  TGCCTCGCCC  GTCTATCTTG  TCCGGTCGTG   22800
CCGGGTCGGT  GGATGTCACG  ATCGAAGGCT  CTGTTTACGG  AGCCCTTCAG  TCATTCTGCC   22860
GCACGCGTTC  GGTAACCACA  TTCGTTGTGC  TTCTGACTGT  GTTCCGGATT  GCGCATTTCC   22920
GTCTCACTGC  CGTCGATGAC  GCGACTATCG  GCACGCCTAT  CGCAAACCGT  AACCGTCCTG   22980
AGCTGGAGAC  GTTGGTTGGC  TGCTTTGTAA  ACACGCAATG  TATGCGTATC  AGCATAGCCG   23040
ACGACGATAA  CTTTGAAGGT  CTTGTGCGAC  AGGTGCGTAA  TGTTGCAACG  GCAGCTTACG   23100
CGAACCAAGA  TGTTCCTTTC  GAACGAATCG  TGTCCGCCCT  AGTTCCAGGG  TCGAGAAACA   23160
CATCCCGCAA  CCCCCTGGTT  CAGCTCATGT  TTGCTGTCCA  GTCCGTGGAA  GATTATGACC   23220
AGGTCCGACT  CGAGGGCTTG  GAGAGTGTCA  TGATGCCTGG  AGAAGCCTCC  ACACGCTTTG   23280
ATATGGAATT  CCACCTCGTC  CCCGGCGATC  AGAAGCTTAC  GGGCAGCGTT  CTTTACTCCT   23340
CAGACCTTTT  TGAGCAAGGC  ACTATCCAGA  ACTTCGTCGA  CATCTTCCAA  GAATGTCTTC   23400
GCTCCGTCCT  GGACCAGCCA  TTGACCCCGA  TCTCCGTTCT  TCCCTTCAGC  AACGCCATTT   23460
CAAACCTCGA  GAGCTTGGAT  CTCCTGGAGA  TGCCGACCTC  AGACTACCCC  CGCGATCGGA   23520
CAGTCGTTGA  TCTCTTCCGA  GAGCAAGCGG  CAATCTGCCC  CGACAGCATC  GCCGTCAAAG   23580
ACTCATCGTC  GCAACTGACA  TATGCTCAAC  TGGATGAGCA  ATCCGACCGT  GTTGCCGCCT   23640
GGCTGCACGA  GCGCCACATG  CCGGCGGAGT  CTTTGGTCGG  TGTACTGTCG  CCACGGTCGT   23700
GCGAGACTAT  CATCGCGTAC  TTTGGCATCA  TGAAGGCAAA  CCTGGCTTAC  CTGCCGTTGG   23760
ATGTTTATGC  GCCAGATGCC  CGTCTGGCGG  CTATCCTGGA  TACAGTCGAA  GGCGAAAGAC   23820
TGCTTCTGTT  GGGCGCAGGT  GTCCCTCAGC  CCGGCATCCA  GATCCCTCGC  CTGTCAACAG   23880
CATACATCGC  GGAAGCACTG  AGCCATGCCA  CGACCGTCGA  TGTCACTTCC  ATCCCACAGC   23940
CCTCGGCCAC  CAGCCTTGCG  TACGTCATTT  TCACTTCGGG  ATCTACTGGC  AAGCCCAAGG   24000
GTGTCATGAT  CGAGCATCGC  GGCATCGTGC  GCCTGGTTAG  AGATACCAAC  GTCAACGTGT   24060
TCCCGGAATC  GGGATCAGCT  TTGCCTGTCT  CTCACTTCTC  CAACCTCGCC  TGGGATGCGG   24120
CGACTTGGGA  GATCTACACT  GCCGTGCTCA  ATGGAGGGAC  CGTTGTGTGC  ATTGACCGAG   24180
ACACCATGCT  GGACATAGCC  GCGTTGAACT  CAACATTCCG  GAAGGAGAAC  GTTCGGGCTG   24240
CCTTCTTCAC  CCCTGCCTTC  CTGAAGCAAT  GCCTTGCCGA  GACGCCAGAG  CTGGTCGCCA   24300
ACCTAGAGAT  CCTTCACACG  GCAGGCGATC  GTCTCGATCC  TGGAGATGCC  AACCTGGCTG   24360
GAAAGACAGC  CAAGGGTGGT  ATCTTCAACG  TCCTGGGTCA  CACAGAGAAC  ACTGCCTATA   24420
```

| | | | | | |
|---|---|---|---|---|---|
| GTACCTTCTA | CCCTGTGGTT | GGTGAGGAGA | CGTTCGTCAA | TGGTGTCCCC | GTCGGTCGCG 24480 |
| GCATCAGCAA | CTCCCATGCA | TATATCATCG | ACCGACACCA | GAAGCTCGTA | CCCGCAGGTG 24540 |
| TCATGGGAGA | GCTTATTCTC | ACTGGCGACG | GTGTTGCGCG | AGGTTACACC | GACTCTGCGC 24600 |
| TGAACAAGGA | TCGATTCGTT | TACATCGATA | TCAACGGCAA | AAGCACATGG | TCGTACCGCA 24660 |
| CAGGCGATAA | GGCACGTTAT | CGACCAAGGG | ACGGCCAGCT | GGAATTCTTT | GGCCGCATGG 24720 |
| ACCAAATGGT | CAAGATCCGT | GGTGTTCGAA | TCGAACCCGG | CGAAGTTGAG | CTCACCCTGC 24780 |
| TCGACCATAA | GTCCGTCCTG | GCCGCGACTG | TGGTGGTCAG | AAGACCACCC | AATGGCGACC 24840 |
| CGGAGATGAT | TGCCTTCATC | ACCATCGACG | CTGAAGACGA | CGTGCAAACT | CACAAGGCCA 24900 |
| TTTACAAGCA | CCTCCAGGGT | ATCTTGCCCG | CGTACATGAT | TCCCTCACAC | CTTGTCATCC 24960 |
| TTGACCAGAT | GCCGGTCACC | GACAACGGTA | AGGTCGATCG | CAAGGATCTC | GCACTCAGAG 25020 |
| CGCAGACAGT | ACAGAAACGC | AGGTCTACCG | CTGCAAGGGT | ACCACCTCGT | GACGAGGTGG 25080 |
| AGGCTGTTCT | TTGCGAAGAG | TACAGCAACT | TACTTGAAGT | TGAGGTTGGC | ATTACCGACG 25140 |
| GATTCTTCGA | CCTGGGTGGA | CATTCGCTCC | TCGCCACCAA | GCTTGCGGCC | CGCCTAAGCC 25200 |
| GACAACTCAA | CACTCGCGTG | TCTGTCAAGG | ACGTCTTTGA | CCAGCCAATA | CTCGCTGACC 25260 |
| TCGCTGATAT | CATCCGCCGC | GGTTCCCATC | GCCACGATCC | GATTCCTGCC | ACTCCATACA 25320 |
| CGGGCCCTGT | CGAACAGTCG | TTCGCTCAGG | GCCGCCTGTG | GTTCTTGGAA | CAACTGAACC 25380 |
| TAGGTGCCAG | CTGGTACTTG | ATGCCCTTCG | CGATCCGGAT | GCGTGGGCCC | CTCCAGACAA 25440 |
| AGGCGCTGGC | TGTCGCACTG | AACGCCTTGG | TGCACCGGCA | CGAGGCGTTG | CGGACGACTT 25500 |
| TCGAGGACCA | CGATGGGGTT | GGTGTTCAGG | TCATTCAACC | AAAGTCAAGC | CAAGACCTGC 25560 |
| GGATCATCGA | CCTATCAGAC | GCTGTAGATG | ATACTGCCTA | TCTCGCCGCG | CTCAAGAGGG 25620 |
| AACAGACAAC | AGCCTTCGAC | CTGACCTCTG | AACCAGGGTG | GAGAGTGTCA | CTCTTACGCC 25680 |
| TAGGTGACGA | TGATTACATC | CTTTCTATCG | TTATGCACCA | CATTATCTCT | GATGGCTGGA 25740 |
| CTGTTGATGT | GCTACGACAA | GAACTCGGCC | AGTTCTATTC | AGCTGCGATC | AGGGGTCAGG 25800 |
| AGCCTTTATC | GCAGGCCAAG | TCCCTCCCTA | TTCAATACCG | CGACTTTGCT | GTTTGGCAGA 25860 |
| GGCAGGAGAA | CCAGATCAAG | GAGCAAGCGA | AGCAGCTCAA | GTATTGGTCA | CAGCAGCTCG 25920 |
| CAGATAGCAC | CCCCTGCGAG | TTCCTAACGG | ACCTCCCTCG | GCCCTCTATC | CTGTCTGGTG 25980 |
| AAGCTGACGC | CGTTCCTATG | GTGATTGATG | GCACGGTGTA | TCAGCTCCTT | ACTGATTTCT 26040 |
| GCCGGACGCA | CCAAGTCACA | TCGTTCTCAG | TCCTGCTCGC | AGCCTTCCGC | ACTGCCCACT 26100 |
| ACCGCCTTAC | CGGGACACTC | GACGCGACGG | TTGGCACACC | AATCGCTAAC | CGGAACCGGC 26160 |
| CAGAGTTGGA | AGGTCTGATC | GGTTTCTTCG | TTAACACGCA | GTGTATGAGG | ATGGCAATCA 26220 |
| GTGAGACTGA | AACCTTTGAG | TCACTAGTCC | AGCAGGTTCG | CTTGACTACG | ACAGAAGCCT 26280 |
| TTGCGAACCA | AGATGTGCCG | TTTGAGCAGA | TTGTGTCAAC | CCTTCTTCCT | GGGTCACGAG 26340 |
| ATACGTCAAG | GAACCCGCTT | GTGCAGGTCA | TGTTTGCCCT | GCAATCACAG | CAAGACCTCG 26400 |
| GAAGAATCCA | GCTGGAAGGT | ATGACGGACG | AAGCTCTGGA | AACGCCGCTG | TCGACGAGAC 26460 |
| TCGACCTTGA | GGTTCACCTC | TTCCAGGAGG | TTGGAAAGCT | GAGCGGCAGC | CTCTTGTACT 26520 |
| CCACGGACCT | CTTCGAGGTC | GAGACGATTC | GTGGAATCGT | TGATGTGTTC | CTGGAGATCT 26580 |
| TGCGCCGCGG | CCTTGAGCAA | CCCAAGCAGC | GACTGATGGC | CATGCCAATT | ACCGATGGCA 26640 |
| TCACAAAGCT | ACGCGACCAG | GGTCTCCTAA | CAGTGGCGAA | ACCAGCCTAC | CCTCGCGAAT 26700 |
| CGAGTGTCAT | AGATCTGTTC | AGACAGCAGG | TTGCCGCCGC | ACCGGATGCC | ATCGCTGTGT 26760 |
| GGGATTCCTC | CTCAACATTG | ACCTATGCCG | ACCTCGATGG | GCAATCGAAC | AAGCTCGCCC 26820 |

```
ACTGGCTGTG CCAGCGCAAT ATGGCCCCAG AGACCTTGGT AGCTGTATTC GCGCCACGCT    26880
CATGCCTCAC CATCGTCGCA TTCCTCGGTG TTTTGAAGGC TAATCTGGCC TACCTGCCCT    26940
TGGATGTCAA TGCGCCTGCT GCTCGTATCG AGGCTATCCT GTCAGCAGTA CCAGGCCACA    27000
AGCTGGTCCT GGTGCAGGCT CATGGGCCCG AGCTTGGCCT GACGATGGCT GATACTGAAC    27060
TGGTGCAGAT CGACGAGGCA CTTGCATCCA GTTCATCCGG TGACCATGAG CAGATCCATG    27120
CGTCCGGCCC TACTGCCACA AGTCTTGCCT ACGTGATGTT TACGTCAGGG TCTACTGGGA    27180
AACCAAAGGG TGTCATGATC GACCACCGCA GCATCATTCG ACTTGTCAAG AACAGCGATG    27240
TTGTTGCCAC TCTGCCTACG CCAGTCCGGA TGGCGAATGT ATCAAACCTT GCCTTCGACA    27300
TCTCGGTGCA AGAAATCTAC ACGGCGCTCC TAAACGGTGG CACTCTGGTC TGCTTGGACT    27360
ATCTGACGCT ATTGGACAGC AAAATTCTTT ATAACGTTTT TGTGGAAGCA CAGGTCAACG    27420
CCGCCATGTT CACGCCGGTT CTCCTCAAGC AATGTCTTGG AAACATGCCC GCCATCATCA    27480
GTCGCCTGAG TGTTCTCTTT AACGTTGGTG ACAGGCTGGA TGCCCACGAT GCTGTGGCTG    27540
CATCAGGCCT GATCCAAGAC GCCGTATACA ACGCCTACGG TCCCACGGAG AACGGCATGC    27600
AGAGTACGAT GTACAAGGTC GACGTCAATG AGCCTTTCGT CAACGGCGTC CCGATCGGTC    27660
GATCCATCAC CAACTCTGGG GCTTACGTCA TGGACGGCAA TCAACAGCTC GTATCTCCTG    27720
GTGTGATGGG AGAAATTGTC GTTACCGGTG ATGGTCTTGC CCGTGGCTAT ACAGACTCAG    27780
CCCTAGACGA GGACCGGTTT GTTCACGTCA CGATCGATGG TGAGGAAAAT ATCAAGGCAT    27840
ACCGAACCGG TGATCGAGTC CGCTACCGGC CCAAGGACTT TGAGATTGAA TTCTTCGGCC    27900
GTATGGATCA ACAGGTGAAG ATTCGTGGTC ACCGCATTGA GCCAGCAGAA GTGGAACATG    27960
CACTGCTCGG CCACGACTTG GTTCACGATG CAGCTGTCGT GCTTCGAAAG CCAGCAAATC    28020
AAGAACCAGA GATGATTGCT TTCATCACCA GCCAGGAAGA CGAGACTATC GAGCAGCATG    28080
AGTCAAACAA GCAGGTCCAA GGCTGGGGAG AGCATTTCGA CGTAAGCAGG TATGCTGATA    28140
TCAAGGATCT CGACACTTCT ACCTTTGGTC ACGACTTTTT GGGATGGACA TCTATGTATG    28200
ACGGAGTTGA CATTCCTGTC AACGAGATGA AAGAGTGGCT TGATGAAACT ACGGCCTCCC    28260
TCCTAGACAA CCGCCCACCT GGTCATATCC TCGAGATCGG AGCCGGAACT GGCATGATTC    28320
TATCTAACCT GGGCAAAGTC GACGGCCTAC AGAAGTATGT CGGTCTTGAC CCGGCTCCCT    28380
CAGCCGCAAT CTTTGTCAAC GAAGCCGTCA AGTCTCTGCC AAGTCTAGCC GGTAAGGCCC    28440
GGGTACTTGT TGGAACTGCC CTGGATATCG GTTCTCTGGA CAAGAATGAG ATCCAACCTG    28500
AGCTTGTGGT TATCAACTCC GTGGCCCAGT ACTTCCCCAC ATCAGAGTAC TTGATCAAGG    28560
TGGTCAAAGC TGTTGTGGAA GTGCCCAGCG TCAAGCGTGT TTTCTTTGGC GATATCAGAT    28620
CCCAGGCCCT TAACAGGGAC TTCCTTGCAG CTCGTGCCGT TCGTGCGTTG GGTGACAATG    28680
CTAGCAAAGA GCAGATCCGG GAAAAGATCG CAGAGCTCGA AGAGAGCGAA GAAGAACTTC    28740
TCGTGGACCC AGCCTTCTTC GTGAGCTTGA GAAGCCAGCT GCCCAACATC AAGCACGTTG    28800
AGGTCCTGCC CAAGCTGATG AAGGCCACCA ACGAGCTGAG CTCGTACAGA TATGCTGCGG    28860
TTCTACACAT CAGCCACAAC GAAGAGGAGC AGCTGCTCAT ACAGGATATC GATCCCACAG    28920
CATGGGTTGA CTTTGCAGCA ACGCAAAAGG ACTCTCAAGG TCTGAGAAAC CTTCTACAAC    28980
AAGGACGAGA TGATGTGATG ATCGCGGTCG GGAACATCCC GTACAGCAAG ACCATAGTGG    29040
AGCGACACAT TATGAACTCT CTTGACCAAG ATCACGTCAA CTCACTCGAC GGGACATCCT    29100
GGATCTCAGA TGCTCGATCA GCCGCTGCAA TCTGCACTTC GTTCGACGCA CCCGCCCTCA    29160
CGCAGTTGGC CAAGGAGGAG GGATTCCGGG TAGAGTTGAG CTGGGCGCGA CAGAGATCTC    29220
```

```
AAAACGGCGC  CCTCGATGCC  GTTTTCCACC  GTCTTGCAAC  CGATGCAAAT  TGCGAGCGCA   29280

GTCGTGTCCT  GGTACACTTC  CCTACCGACC  ATCAAGGTCG  ACAACTTCGA  ACCCTGACGA   29340

ACCGGCCACT  CCAGCGAGCT  CAGAGCCGCC  GTATCGAGTC  ACAAGTCTTC  GAGGCACTGC   29400

AGACAGCACT  GCCGGCCTAC  ATGATCCCAT  CGCGCATTAT  CGTGCTCCCG  CAGATGCCGA   29460

CCAACGCCAA  CGGCAAAGTG  GACAGGAAAC  AGCTCGCTCG  CCGCGCGCAG  GTTGTGGCCA   29520

AGAGAAAGGC  AGTGTCAGCG  CGCGTTGCGC  CTCGTAATGA  CACCGAGATA  GTTCTTTGCG   29580

AGGAATACGC  AGATATCCTA  GGAACTGAAG  TTGGCATCAC  GGACAACTTC  TTCGACATGG   29640

GCGGGCATTC  ACTCATGGCT  ACGAAGCTCG  CAGCCCGACT  AAGCCGGCGA  CTAGATACCC   29700

GGGTTACGGT  CAAGGAGGTG  TTCGATAAAC  CCGTCCTGGC  TGACCTCGCT  GCTTCGATCG   29760

AACAGGGCTC  GACACCTCAT  CTGCCTATTG  CCTCATCGGT  GTATTCCGGA  CCGGTGGAGC   29820

AGTCGTACGC  CCAAGGTCGC  TTGTGGTTCT  TGGATCAGTT  CAACCTCAAC  GCGACGTGGT   29880

ATCACATGTC  GCTGGCGATG  AGGCTGCTCG  GGCCGCTCAA  CATGGACGCG  CTGGACGTGG   29940

CCTTACGGGC  GCTGGAGCAG  CGACACGAGA  CGCTTCGCAC  AACCTTTGAG  GCTCAAAAGG   30000

ACATCGGCGT  CCAGGTCGTT  CATGAGGCCG  GAATGAAGAG  GCTCAAGGTC  CTTGACCTAT   30060

CAGACAAGAA  CGAGAAGGAG  CACATGGCCG  TGCTAGAGAA  TGAACAGATG  AGACCGTTCA   30120

CTCTTGCTTC  AGAGCCAGGC  TGGAAGGGTC  ATCTTGCTCG  CCTTGGCCCC  ACGGAGTATA   30180

TCCTCTCCCT  CGTCATGCAT  CACATGTTCT  CAGACGGCTG  GTCCGTTGAT  ATCCTGAGAC   30240

AGGAGCTCGG  TCAATTCTAC  TCAGCCGCTT  TACGTGGCAG  GGATCCGTTA  TCTCAGGTCA   30300

AGCCCCTCCC  AATACAATAT  CGTGACTTTG  CGGCTTGGCA  GAAGGAAGCT  GCCCAAGTTG   30360

CCGAGCATGA  GAGGCAGCTC  GCGTACTGGG  AGAACCAGTT  AGCTGACAGT  ACTCCCGGTG   30420

AGCTTCTGAC  CGACTTTCCC  CGCCCACAGT  TCCTGAGTGG  GAAGGCTGGT  GTCATCCCGG   30480

TCACCATTGA  GGGGCCGGTC  TACGAGAAGC  TTCTGAAGTT  CTCCAAGGAG  CGCCAGGTAA   30540

CTCTGTTCTC  GGTGCTATTA  ACAGCGTTCC  GGGCCACACA  CTTTCGTCTC  ACTGGTGCAG   30600

AGGATGCTAC  GATCGGTACC  CCAATTGCAA  ATCGCAACCG  GCCAGAACTC  GAGCATATCA   30660

TTGGATTCTT  CGTCAACACC  CAATGCATGC  GTCTTCTCCT  CGATACCGGC  AGCACATTCG   30720

AATCCCTAGT  CCAGCATGTT  CGGTCCGTGG  CTACAGATGC  CTATTCCAAT  CAGGATATTC   30780

CCTTCGAACG  GATCGTCTCG  GCACTTCTCC  CTGGCTCGAG  AGATGCCTCA  CGAAGCCCAC   30840

TAATCCAGCT  TATGTTTGCC  TTGCACTCAC  AGCCAGATCT  CGGGAACATT  ACTCTCGAAG   30900

GACTCGAGCA  TGAGCGCCTG  CCAACAAGCG  TCGCAACACG  TTTCGACATG  GAGTTCCACC   30960

TGTTCCAAGA  GCCTAACAAG  CTGAGTGGTT  CAATACTCTT  TGCCGATGAG  CTCTTCCAGC   31020

CTGAAACAAT  CAACAGCGTC  GTGACTGTGT  TCCAGGAGAT  ACTCCGACGC  GGCCTCGACC   31080

AACCCCAAGT  CTCCATTTCT  ACTATGCCCC  TGACTGATGG  GTTGATTGAT  CTCGAGAAAC   31140

TGGGCTTGCT  GGAAATCGAG  AGCAGCAACT  TCCCTCGCGA  CTACTCGGTT  GTCGACGTCT   31200

TCCGACAGCA  GGTGGCTGCC  AATCCAAATG  CGCCCGCTGT  CGTGGATTCG  GAGACATCCA   31260

TGAGCTACAC  CTCGCTAGAT  CAGAAGTCTG  AGCAGATTGC  TGCCTGGTTA  CACGCTCAAG   31320

GCCTCCGCCC  TGAGTCATTG  ATCTGCGTGA  TGGCGCCACG  ATCTTTCGAA  ACGATCGTCT   31380

CCTTATTCGG  TATCTTGAAG  GCTGGCTACG  CCTACCTGCC  TCTGGATGTG  AATTCCCCTG   31440

CAGCTCGAAT  CCAACCGATC  CTATCCGAGG  TTGAAGGAAA  AAGACTGGTA  CTGCTAGGAT   31500

CAGGGATAGA  CATGCCTCAA  AGCGACCGAA  TGGATGTTGA  AACCGCTCGA  ATTCAGGACA   31560

TCCTAACGAA  CACAAAGGTC  GAGAGATCTG  ATCCCATGAG  CAGGCCATCG  GCAACTAGCC   31620
```

| | | | | | |
|---|---|---|---|---|---|
| TTGCCTATGT | CATCTTCACC | TCCGGGTCAA | CTGGCCGTCC | CAAGGGCGTG | ATGATCGAGC | 31680
| ATCGCAATAT | TCTGCGCCTT | GTCAAGCAGT | CTAATGTTAC | GTCTCAGCTG | CCGCAGGATC | 31740
| TGCGCATGGC | ACATATCTCC | AACCTAGCCT | TTGACGCGTC | CATCTGGGAG | ATATTCACGG | 31800
| CAATTTTGAA | TGGCGGCGCC | CTTATTTGCA | TTGATTACTT | CACTTTGCTG | GATAGTCAAG | 31860
| CCCTCCGGAC | GACATTCGAA | AAAGCCAGGG | TCAATGCTAC | CCTATTCGCG | CCGGCCTTGC | 31920
| TCAAAGAATG | CCTCAATCAC | GCGCCGACCT | TGTTTGAGGA | TCTCAAAGTG | CTCTATATCG | 31980
| GTGGCGACCG | ACTCGATGCC | ACCGACGCGG | CCAAAATACA | AGCCCTTGTG | AAGGGCACGG | 32040
| TCTACAACGC | GTACGGGCCG | ACAGAGAACA | CAGTCATGAG | CACGATCTAC | AGGCTCACAG | 32100
| ATGGAGAGTC | TTATGCTAAC | GGTGTGCCAA | TCGGCAATGC | TGTGAGCAGC | TCTGGCGCTT | 32160
| ATATCATGGA | CCAAAAGCAG | CGCCTCGTTC | CTCCCGGTGT | TATGGGAGAG | CTCGTTGTGA | 32220
| GCGGCGATGG | CCTCGCCCGT | GGCTACACCA | ACTCGACCCT | CAATGCTGAT | CGTTTCGTTG | 32280
| ATATTGTCAT | CAACGATCAA | AAAGCCCGCG | CATACCGGAC | CGGAGATCGC | ACTCGTTACC | 32340
| GGCCCAAGGA | TGGTAGCATC | GAGTTCTTCG | GCCGTATGGA | TCAGCAAGTT | AAAATCCGTG | 32400
| GTCATCGAGT | TGAGCCGGCC | GAGGTCGAGC | AAGCCATGCT | CGGCAATAAG | GCTATCCATG | 32460
| ATGCAGCAGT | TGTTGTTCAG | GCGGTGGATG | CCAGGAAAC | GGAGATGATC | GGCTTTGTTT | 32520
| CCATGGCCAG | CGACAGATTC | AGCGAAGGGG | AGGAGGAGAT | CACCAACCAA | GTCCAGGAGT | 32580
| GGGAAGACCA | CTTCGAAAGC | ACCGCCTACG | CTGGCATTGA | GGCCATCGAC | CAGGCTACCC | 32640
| TGGGACGCGA | TTTCACTTCA | TGGACCTCGA | TGTACAACGG | CAACTTGATT | GACAAAGCCG | 32700
| AAATGGAGGA | GTGGCTTGAC | GATACAATGC | AATCCCTCCT | TGATAAGGAG | GATGCCAGGC | 32760
| CGTGTGCTGA | GATCGGAACA | GGTACCGGCA | TGGTTCTATT | CAATTTGCCC | AAGAACGATG | 32820
| GCCTTGAGAG | CTATGTCGGT | ATAGAGCCTT | CACGGTCTGC | AGCCTTGTTC | GTCGACAAAG | 32880
| CAGCCCAAGA | TTTCCCAGGT | CTGCAAGGAA | AGACGCAAAT | CCTTGTCGGC | ACAGCCGAGG | 32940
| ACATCAAGCT | GGTCAAGGAC | TTCCACCCTG | ACGTGGTTGT | CATTAACTCG | GTAGCCCAAT | 33000
| ATTTCCCGAG | CCGGAGCTAC | CTTGTACAGA | TAGCGAGCGA | ACTGATTCAC | ATGACCAGCG | 33060
| TCAAGACGAT | CTTCTTTGGA | GATATGCGAT | CCTGGGCCAC | CAACAGGGAT | TTCCTCGTGT | 33120
| CCCGAGCTCT | TTACACGCTA | GGTGACAAGG | CTACAAAGGA | TCAGATTCGC | CAGGAGGTTG | 33180
| CCCGACTTGA | GGAGAATGAA | GACGAGTTGC | TTGTTGACCC | AGCATTCTTC | ACCTCTTTGA | 33240
| CCAGCCAATG | GCCCGGCAAG | GTCAAGCATG | TTGAGATCTT | GCCGAAGCGG | ATGAGGACGA | 33300
| GCAATGAACT | AAGCTCGTAC | CGATATGCTG | CGGTGCTACA | CATCTGCAGG | GATGGGGAGG | 33360
| GTAGGAACAG | ATATGGCAGG | CGTGTCCACT | CAGTGGAAGA | GAACGCCTGG | ATCGACTTCG | 33420
| CGTCGTCTGG | CATGGATCGT | CACGCCCTCG | TTCAGATGCT | CGATGAACGT | AGAGACGCCA | 33480
| AGACTGTCGC | CATCGGCAAC | ATCCCTCACA | GCAACACGAT | CAACGAGCGA | CACTTTACGA | 33540
| CATCCCTGGA | TACTGAGGGA | GAAGGCATTG | CCCAAGATTC | ACTGGATGGA | TCCGCCTGGC | 33600
| AATCGGCTAC | GAAGGCAATG | GCCGCGCGCT | GTCCTTGCCT | TTCCGTCACC | GAACTGGTCG | 33660
| AGATCGGCCA | AGCGGCAGGA | TTCAGGGTCG | AGGTCAGCTG | GGCTCGTCAA | CGATCCCAAC | 33720
| ATGGTGCACT | GGACGTCGTC | TTCCATCATC | TTGAAGATGA | CAGAGTAGGC | CGCGTCTTGA | 33780
| TCAACTTCCC | CACAGACTTC | GAGCGTCTAC | CCCCTAGCAC | CGGCCTGACC | AGTCGGCCGC | 33840
| TGCAGCGCAT | CCAGAACCGT | CGGTTCGAGT | CGCAGATCCG | CGAACAGCTG | CAAACACTGC | 33900
| TGCCACCTTA | TATGGTTCCA | TCACGGATCG | TCGTGTTGGA | GCGGATGCCT | CTCAACGCAA | 33960
| ACAGCAAAGT | CGACCGTAAA | GAATTGGCAA | GGAAGGCGAG | GACCCTACAA | ACCATCAAGC | 34020

```
CTTCTGCAAC  GCGCGTGGCT  CCTCGCAACG  ATATTGAAGC  CGTCTTGTGC  GACGAGTTCC   34080
AGGCAGTTCT  TGGTGTTACA  GTCGGAGTCA  TGGATAACTT  TTTCGAGTTG  GGCGGACACT   34140
CCCTGATGGC  TACGAAACTG  GCCGCCCGTC  TCAGTCGCCG  CCTCGACACC  CGCGTCTCTG   34200
TGAAGGATAT  CTTCAACCAA  CCAATCCTTC  AAGATCTCGC  GGACGTGGTC  CAGACTGGCT   34260
CCGCTCCTCA  TGAAGCTATT  CCCTCCACGC  CCTACTCTGG  TCCCGTGGAG  CAATCCTTCT   34320
CTCAGGGCCG  TCTATGGTTC  TTGGATCAGC  TGAATCTCAA  TGCATCGTGG  TACCACATGC   34380
CATTAGCGAG  TCGCTTGCGA  GGCCCGCTTC  GGATCGAGGC  GCTGCAGTCA  GCCCTGGCTA   34440
CGATTGAGGC  GCGGCACGAG  TCCCTGCGCA  CCACATTCGA  GGAGCAAGAT  GGTGTTCCCG   34500
TTCAGATTGT  ACGCGCTGCG  CGCAACAAGC  AGCTGAGGAT  CATCGACGTG  TCGGGCACCG   34560
AGGATGCGTA  TCTCGCAGCA  TTGAAGCAAG  AGCAAGACGC  CGCATTCGAT  CTGACTGCTG   34620
AGCCAGGCTG  GCGAGTAGCA  CTGTTGCGCT  TGGGACCGGA  TGATCATGTC  CTGTCTATCG   34680
TCATGCACCA  CATCATATCT  GACGGATGGT  CGGTTGATAT  CCTGCGACAA  GAACTCGGGC   34740
AGCTCTACTC  GAATGCCTCA  TCGCAGCCCG  CTCCTCTTCC  GATTCAATAC  CGAGATTTCG   34800
CCATCTGGCA  GAAGCAGGAT  AGTCAGATCG  CTGAGCACCA  AAAGCAGCTG  AACTACTGGA   34860
AGAGACAACT  GGTCAACAGC  AAGCCGGCTG  AGCTCCTGGC  GGACTTCACT  CGTCCGAAGG   34920
CGTTATCTGG  CGATGCTGAT  GTCATACCGA  TAGAGATTGA  TGACCAGGTA  TATCAGAACC   34980
TCCGCTCGTT  TTGTCGCGCT  CGGCATGTCA  CCAGCTTTGT  TGCACTCTTA  GCAGCTTTCC   35040
GGGCTGCTCA  CTACCGCCTA  ACTGGGGCCG  AAGATGCAAC  TATCGGCTCT  CCAATCGCCA   35100
ACAGAAATCG  ACCTGAGCTT  GAAGGCCTCA  TTGGATGCTT  TGTTAACACC  CAGTGTCTCC   35160
GAATTCCTGT  TAAGAGCGAG  GACACATTTG  ACACGTTGGT  TAAACAGGCA  CGAGAAACGG   35220
CGACCGAGGC  CCAGGACAAC  CAAGATGTCC  CGTTCGAGAG  GATCGTTTCT  TCCATGGTTG   35280
CTAGCTCGCG  AGATACCTCG  CGAAATCCAC  TCGTTCAGGT  CATGTTTGCT  GTGCACTCTC   35340
AGCACGACCT  TGGTAACATT  CGTCTCGAAG  GTGTTGAGGG  GAAGCCCGTT  TCGATGGCAG   35400
CGTCCACACG  CTTTGACGCG  GAAATGCACC  TATTTGAGGA  CCAAGGGATG  CTCGGCGGCA   35460
ACGTCGTCTT  TTCGAAGGAT  CTGTTCGAAT  CCGAGACGAT  CCGCAGTGTT  GTGGCCGTGT   35520
TCCAGGAGAC  CCTGAGGCGT  GGCCTAGCCA  ATCCTCACGC  AAATCTCGCA  ACACTTCCTC   35580
TTACCGATGG  ATTGCCCAGT  CTTCGAAGCC  TGTGTCTTCA  AGTCAATCAG  CCTGACTACC   35640
CCCGAGATGC  CTCCGTGATC  GACGTTTTCA  GAGAGCAGGT  AGCATCGATA  CCCAAGTCTA   35700
TCGCCGTTAT  CGATGCTTCT  TCACAGCTCA  CCTACACCGA  GCTCGACGAG  AGATCTAGCC   35760
AGCTCGCCAC  GTGGCTACGC  CGACAAGTCA  CAGTCCCTGA  GGAGCTGGTC  GGCGTCCTCG   35820
CTCCACGGTC  CTGTGAGACA  ATCATCGCTT  TCCTCGGCAT  CATCAAAGCG  AATCTCGCCT   35880
ATCTGCCACT  TGACGTCAAC  GCACCCGCTG  GTCGGATCGA  GACAATCCTG  TCATCTCTAC   35940
CAGGAAACAG  GCTTATTTTA  CTTGGATCAG  ATACGCAGGC  GGTCAAGCTT  CACGCAAACA   36000
GCGTTCGATT  CACCCGGATC  AGCGACGCCC  TCGTCGAGAG  CGGCAGTCCC  CCTACCGAAG   36060
AACTTTCCAC  ACGGCCGACT  GCACAAAGCC  TTGCCTATGT  CATGTTCACA  TCAGGCTCAA   36120
CTGGCGTCCC  GAAGGGTGTC  ATGGTAGAGC  ACCGGGGTAT  CACACGTCTC  GTGAAAAACA   36180
GCAACGTGGT  CGCAAAGCAA  CCGGCAGCAG  CTGCTATCGC  TCATCTTTCG  AACATTGCTT   36240
TCGACGCCTC  TTCCTGGGAG  ATATACGCTC  CTCTCCTTAA  CGGCGGTACA  GTCGTCTGCA   36300
TTGATTACTA  CACCACGATC  GATATCAAAG  CCCTCGAGGC  GGTATTCAAA  CAGCACCACA   36360
TCCGCGGAGC  AATGCTTCCA  CCAGCACTTC  TCAAACAGTG  TCTGGTCTCT  GCCCCTACTA   36420
```

```
TGATCAGCTC  TCTGGAGATA  CTTTTCGCCG  CCGGCGATCG  GTTGAGCAGC  CAAGATGCCA   36480
TCCTGGCGCG  ACGTGCCGTT  GGTTCGGGCG  TTTACAACGC  TTACGGCCCT  ACTGAGAACA   36540
CGGTCCTGAG  TACGATACAC  AACATCGGCG  AGAATGAGGC  ATTTTCGAAT  GGCGTTCCCA   36600
TTGGAAACGC  TGTCAGTAAC  TCCGGTGCCT  TTGTCATGGA  TCAAAATCAG  CAGCTGGTCT   36660
CCGCCGGTGT  GATCGGAGAG  CTTGTTGTGA  CCGGAGATGG  CCTTGCCCGC  GGATACACAG   36720
ATTCTAAGCT  TAGGGTGGAT  CGATTCATCT  ATATTACCCT  TGACGGGAAC  CGGGTCAGAG   36780
CTTACCGCAC  GGGCGACCGT  GTCAGGCACC  GGCCTAAGGA  TGGGCAAATT  GAGTTCTTCG   36840
GGCGAATGGA  TCAGCAGATC  AAGATCCGTG  GTCATCGCAT  CGAGCCAGCA  GAGGTGGAGC   36900
AGGCTCTCGC  CCGTGACCCG  GCCATCAGCG  ATTCGGCTGT  TATCACTCAG  CTCACGGATG   36960
AAGAGGAGCC  GGAACTGGTG  GCTTTCTTCT  CATTGAAGGG  GAATGCCAAC  GGCACCAACG   37020
GTGTCAACGG  TGTGAGCGAT  CAAGAGAAGA  TCGACGGCGA  TGAGCAACAT  GCTCTGCTGA   37080
TGGAGAACAA  GATCCGTCAC  AACCTACAGG  CGCTGCTGCC  CACTTACATG  ATCCCCTCGC   37140
GGATCATCCA  TGTCGATCAG  CTGCCGGTCA  ATGCCAACGG  TAAGATTGAC  CGCAATGAGC   37200
TGGCTGTTCG  AGCCCAGGCA  ACGCCAAGGA  CCAGTTCAGT  GTCAACCTAC  GTGGCCCCTC   37260
GCAACGATAT  CGAAACCATC  ATCTGTAAGG  AATTCGCAGA  TATCCTCAGC  GTTCGAGTCG   37320
GAATCACAGA  CAACTTCTTC  GACCTGGGTG  GACACTCACT  TATAGCCACC  AAGCTAGCCG   37380
CCCGCCTTAG  CCGTCGACTA  GATACTCGCG  TGTCTGTTAG  GGACGTCTTT  GACACTCCCG   37440
TGGTAGGCCA  ATTGGCGGCT  TCTATCCAGC  AAGGCTCGAC  CCCTCATGAA  GCTATTCCGG   37500
CGTTATCACA  CTCGGGACCT  GTGCAACAGT  CCTTTGCTCA  AGGCCGTCTT  TGGTTCCTGG   37560
ACCGTTTCAA  TCTCAACGCT  GCCTGGTACA  TCATGCCATT  CGGCGTTCGT  CTTCGCGGAC   37620
CTCTCCGAGT  CGATGCACTT  CAGACTGCAT  TGAGGGCTCT  CGAAGAACGG  CACGAGTTGC   37680
TACGCACCAC  GTTCGAAGAA  CAGGATGGCG  TTGGTATGCA  AATCGTTCAC  TCGCCCCGAA   37740
TGAGGGACAT  CTGCGTCGTA  GACATCTCTG  GCGCCAATGA  GGATCTTGCG  AAGCTGAAGG   37800
AGGAGCAGCA  AGCTCCTTTC  AATCTCTCTA  CTGAAGTCGC  TTGGAGGGTA  GCACTCTTCA   37860
AGGCTGGAGA  GAACCACCAC  ATCCTCTCTA  TCGTCATGCA  TCACATAATT  TCAGATGGCT   37920
GGTCAGTTGA  CATCTTCCAG  CAGGAGCTTG  CCCAATTCTA  CTCGGTAGCT  GTACGAGGGC   37980
ATGACCCCCT  TTCCCAGGTC  AAACCGCTCC  CCATTCACTA  CCGCGATTTT  GCTGTCTGGC   38040
AGAGACAAGA  TAAGCAAGTT  GCCGTTCACG  AAAGCCAACT  TCAGTACTGG  ATAGAGCAGC   38100
TCGCGGATAG  CACGCCAGCC  GAGATCCTAT  CTGATTTTAA  CCGACCGGAG  GTCTTGTCCG   38160
GCGAAGCTGG  TACAGTTCCC  ATCGTGATCG  AGGACGAGGT  TTATGAGAAG  CTCTCCCTCT   38220
TCTGCCGCAA  TCATCAGGTC  ACCAGCTTCG  TCGTCCTTCT  GGCTGCTTTC  CGCGTCGCAC   38280
ATTATCGCCT  AACTGGGGCA  GAGGATGCGA  CTATCGGTAC  ACCAATTGCG  AACCGCAACC   38340
GCCCCGAACT  TGAGGACTTG  ATCGGTTTCT  TTGTCAATAC  ACAATGCATG  AGAATCGCGC   38400
TCGAAGAACA  CGATAATTTC  CTATCAGTAG  TGCGAAGAGT  TCGCTCAACA  GCGGCAAGCG   38460
CCTTCGAAAA  CCAGGATGTG  CCATTCGAGC  GCCTTGTATC  TGCACTTCTG  CCCGGCTCTA   38520
GAGATGCCTC  CCGGAATCCC  CTCGTTCAAC  TCATGTTTGT  CGTCCACTCC  CAGCGAAATC   38580
TCGGTAAACT  GCAACTGGAG  GGCTTGGAAG  GCGAACCAAC  CCCGTACACC  GCGACGACCC   38640
GCTTCGATGT  TGAGTTCCAC  CTCTTCGAAC  AAGACAAAGG  CCTCGCCGGA  AATGTTGTCT   38700
TCGCAGCAGA  CTTGTTCGAG  GCTGCCACTA  TCCGCAGCGT  TGTTGAAGTC  TTCCACGAGA   38760
TCCTCCGTCG  TGGTCTCGAC  CAGCCAGATA  TCGCAATTTC  CACCATGCCA  CTTGTCGATG   38820
```

```
GCCTGGCGGC GCTCAACAGC CGTAACTTAC CCGCAGTTGA AGACATCGAA CCTGACTTCG    38880
CCACCGAGGC CTCGGTGGTT GATGTCTTCC AGACACAAGT GGTCGCTAAC CCAGATGCCC    38940
TGGCTGTGAC CGACACATCC ACAAAGCTTA CATATGCGGA GCTGGATCAA CAATCCGATC    39000
ATGTCGCGGC TTGGCTGTCC AAACAGAAGC TACCAGCAGA GAGCATCGTC GTTGTTCTTG    39060
CGCCACGATC CTCTGAGACT ATCGTAGCAT GCATTGGCAT CCTCAAAGCG AACCTCGCAT    39120
ATCTCCCCAT GGATTCCAAC GTCCCCGAAG CCCGTCGCCA AGCAATTCTT TCGGAGATTC    39180
CAGGGGAGAA GTTCGTTTTG CTTGGAGCAG GAGTGCCTAT TCCTGACAAC AAGACAGCTG    39240
ATGTCAGGAT GGTCTTCATC AGCGATATCG TCGCCAGCAA GACAGACAAG TCCTACTCAC    39300
CCGGCACTCG GCCATCTGCA TCAAGCCTTG CCTATGTTAT CTTCACATCA GGCTCGACAG    39360
GTCGGCCAAA GGGTGTCATG GTCGAGCATC GGGGTGTTAT TTCTTTGGTG AAGCAGAACG    39420
CTTCAAGAAT ACCACAAAGT CTGCGGATGG CACATGTTTC CAATCTCGCA TTCGATGCTT    39480
CCGTGTGGGA GATATTCACC ACGCTGCTCA ATGGAGGAAC GCTTTTCTGT ATCAGCTACT    39540
TTACTGTCTT GGACAGCAAA GCACTTTCTG CCGCTTTCTC CGATCATCGC ATTAACATCA    39600
CCCTGCTCCC ACCGGCCTTG CTCAAGCAAT GTCTTGCAGA CGCGCCATCT GTCCTGAGCT    39660
CCCTCGAGTC TCTGTACATT GGAGGCGACC GCCTTGATGG AGCTGATGCA ACCAAGGTGA    39720
AGGACCTCGT CAAAGGCAAG GCCTACAATG CCTACGGTCC CACCGAGAAT TCCGTCATGA    39780
GCACGATCTA TACCATCGAA CACGAGACTT TTGCGAATGG CGTTCCCATC GGCACATCTT    39840
TAGGCCCCAA GTCCAAGGCC TACATTATGG ACCAGGATCA GCAGCTCGTA CCAGCAGGCG    39900
TGATGGGAGA GCTTGTCGTT GCTGGCGATG GTCTCGCACG AGGGTATACC GATCCATCAC    39960
TGAACACGGG CCGGTTCATC CACATCACGA TCGATGGCAA ACAAGTTCAG GCATACCGGA    40020
CCGGCGATCG AGTCAGATAC CGACCTAGGG ACTACCAAAT CGAGTTCTTT GGCCGTTTAG    40080
ATCAGCAGAT CAAGATTCGC GGTCATCGCA TCGAGCCAGC TGAAGTGGAG CAGGCTCTTC    40140
TCAGCGACTC ATCGATCAAC GATGCCGTTG TTGTGTCGGC ACAAAACAAG GAGGGACTCG    40200
AAATGGTTGG TTACATCACG ACCCAGGCTG CACAATCCGT CGACAAGGAG GAAGCCAGCA    40260
ACAAGGTGCA GGAGTGGGAG GCTCATTTCG ACTCAACTGC ATATGCCAAC ATCGGGGGTA    40320
TTGATCGCGA TGCCCTCGGA CAGGACTTCT TATCCTGGAC ATCTATGTAC GACGGCTCAT    40380
TGATTCCCCG TGAAGAGATG CAGGAATGGC TCAACGACAC TATGCGCTCA CTCCTCGACA    40440
ACCAACCACC CGGAAAAGTG CTCGAGATCG GAACTGGTAC CGGTATGGTG CTGTTCAATC    40500
TCGGCAAGGT TGAGGGACTA CAGAGCTATG CCGGTCTTGA GCCCTCGCGC TCCGTCACCG    40560
CCTGGGTTAA CAAGGCAATC GAAACTTTCC CAAGCCTGGC AGGAAGCGCC CGAGTCCACG    40620
TTGGAACCGC CGAGGATATC AGCTCCATTG ATGGACTTCG TTCCGATCTC GTTGTGATCA    40680
ACTCAGTCGC CCAATACTTC CCAAGTCGAG AATATCTCGC TGAGCTGACG GCCAACTTGA    40740
TTCGACTGCC CGGCGTTAAG CGTATTTTCT TCGGTGACAT GAGAACGTAT GCTACCAATA    40800
AGGACTTCTT GGTGGCACGA GCAGTCCATA CCCTAGGGTC CAATGCATCG AAGGCCATGG    40860
TTCGACAACA AGTGGCCAAG CTTGAAGATG ACGAGGAAGA GTTGCTTGTT GACCCTGCCT    40920
TCTTCACCAG CCTGAGCGAC CAGTTCCCTG ACGAAATCAA GCATGTCGAA ATTCTGCCAA    40980
AGAGGATGGC CGCGACCAAC GAACTCAGCT CTTACAGATA TGCTGCTGTC ATTCATGTGG    41040
GAGGCCACCA GATGCCGAAT GGGGAGGATG AGGATAAGCA ATGGGCTGTC AAGGATATCA    41100
ATCCGAAGGC CTGGGTGGAC TTTGCTGGCA CGAGGATGGA CCGTCAGGCT CTCTTGCAGC    41160
TCCTTCAGGA CCGCCAACGT GGCGATGACG TTGTTGCCGT CAGTAACATC CCATACAGCA    41220
```

```
AGACCATCAT  GGAGCGCCAT  CTGTCTCAGT  CACTTGATGA  TGACGAGGAC  GGCACTTCAG   41280
CGGTAGACGG  AACGGCCTGG  ATATCGCGTA  CGCAATCACG  GGCGAAGGAA  TGCCCTGCTC   41340
TCTCAGTGGC  CGACCTGATT  GAGATTGGTA  AGGGGATCGG  CTTCGAAGTT  GAGGCCAGCT   41400
GGGCTCGACA  ACACTCCCAG  CGCGGCGGAC  TCGATGCTGT  TTTCCACCGA  TTCGAACCAC   41460
CAAGACACTC  AGGTCATGTC  ATGTTCAGGT  TCCCGACTGA  ACACAAGGGC  CGGTCTTCGA   41520
GCAGTCTCAC  GAATCGCCCG  CTACACCTGC  TTCAGAGCCG  CCGACTGGAG  GCAAAGGTCC   41580
GCGAGCGGCT  GCAATCACTG  CTTCCACCGT  ACATGATTCC  GTCTCGGATC  ACGTTGCTCG   41640
ATCAGATGCC  TCTCACGTCC  AACGGCAAGG  TGGATCGCAA  GAAGCTTGCT  CGACAAGCCC   41700
GGGTCATCCC  AAGAAGTGCG  GCAAGCACGT  TGGACTTTGT  GGCGCCACGC  ACGGAAATCG   41760
AAGTCGTCCT  CTGCGAAGAA  TTTACCGATC  TACTAGGCGT  CAAGGTTGGC  ATCACAGACA   41820
ACTTCTTCGA  GTTGGGCGGC  CATTCGCTGC  TGGCCACGAA  ACTGAGCGCA  CGTCTAAGTC   41880
GCAGACTGGA  CGCCGGTATC  ACTGTGAAGC  AGGTCTTTGA  CCAGCCAGTA  CTTGCTGATC   41940
TTGCTGCTTC  TATTCTTCAA  GGCTCGTCTC  GTCACAGGTC  TATCCCGTCT  TTACCCTACG   42000
AAGGACCCGT  GGAGCAGTCC  TTTGCCCAGG  GGCGCCTGTG  GTTCCTCGAC  CAGTTCAACA   42060
TCGATGCCTT  GTGGTACCTT  ATTCCATTTG  CACTCCGCAT  GCGCGGGCCG  CTGCAAGTTG   42120
ACGCCCTCGC  TGCTGCCCTG  GTGGCACTTG  AAGAGCGTCA  TGAATCTCTG  CGCACAACGT   42180
TTGAGGAACG  AGACGGAGTC  GGCATCCAAG  TGGTGCAACC  CCTCCGCACG  ACCAAGGATA   42240
TCCGGATCAT  CGACGTGTCA  GGCATGCGAG  ACGACGACGC  CTACCTCGAG  CCATTGCAGA   42300
AAGAACAGCA  GACTCCTTTC  GACCTTGCTT  CAGAGCCTGG  CTGGAGGGTA  GCACTGCTGA   42360
AGCTTGGAAA  GGATGACCAC  ATCCTCTCTA  TTGTCATGCA  CCACATCATC  TCTGACGGGT   42420
GGTCTACTGA  AGTCTTGCAA  AGGGAACTCG  GTCAATTCTA  CTTGGCAGCG  AAATCCGGGA   42480
AAGCCCCCTT  ATCGCAGGTT  GCCCCGCTTC  CTATTCAGTA  TCGCGATTTT  GCTGTTTGGC   42540
AGAGACAAGA  GGAACAGGTC  GCTGAGAGTC  AAAGGCAGCT  CGACTACTGG  AAGAAGCAGC   42600
TTGCGGACAG  TAGCCCGGCT  GAGCTCTTGG  CTGACTACAC  CAGGCCGAAC  GTACTGTCTG   42660
GAGAGGCAGG  CAGCGTGTCT  TTCGTGATCA  ACGATTCGGT  TTACAAGAGC  CTCGTCTCCT   42720
TCTGCCGGTC  TCGCCAAGTA  ACCACCTTTA  CGACTTTACT  GGCAGCGTTT  CGCGCCGCTC   42780
ACTATCGAAT  GACCGGGTCA  GACGACGCAA  CTATTGGCAC  GCCAATTGCC  AATCGCAACA   42840
GGCCTGAGCT  TGAAAACTTG  ATCGGCTGCT  TCGTCAATAC  CCAGTGCATG  CGTATCACTA   42900
TCGGCGACGA  TGAGACGTTT  GAATCACTGG  TACAACAGGT  ACGGTCTACC  ACCGCGACAG   42960
CCTTCGAGAA  TCAAGACGTT  CCGTTTGAAC  GAATCGTTTC  CACCCTCAGT  GCCGGGTCCA   43020
GGGATACGTC  CCGAAACCCC  CTAGTACAGC  TTCTCTTTGC  GGTTCATTCT  CAACAAGGCC   43080
TGGGCAGGAT  CCAGCTCGAC  GGTGTCGTCG  ATGAGCCGGT  TCTGTCGACC  GTTTCGACTC   43140
GGTTCGATCT  CGAATTCCAC  GCCTTCCAAG  AGGCCGACCG  GCTCAATGGA  AGTGTCATGT   43200
TTGCCACGGA  CCTGTTCCAG  CCCGAGACCA  TCCAAGGTTT  CGTTGCGGTT  GTCGAAGAGG   43260
TTCTACAGCG  TGGCCTGGAG  CAGCCGCAGA  GTCCCATCGC  AACCATGCCG  CTGGCCGAAG   43320
GCATCGCTCA  GCTCCGAGAT  GCCGGCGCGC  TGCAGATGCC  AAAGTCTGAT  TACCCTCGCA   43380
ACGCGTCCCT  CGTCGATGTC  TTCCAGCAGC  AGGCTATGGC  CAGCCCGTCA  ACTGTCGCCG   43440
TCACTGACTC  GACCTCCAAG  CTGACGTATG  CCGAGCTGGA  TCGACTCTCC  GATCAAGCTG   43500
CTTCCTATCT  GCGTCGGCAG  CAACTCCCGG  CGGAGACAAT  GGTGGCCGTT  CTCGCACCGC   43560
GCTCTTGTGA  GACCATCATC  GCGTTCCTAG  CTATTCTCAA  AGCAAATCTT  GCCTACATGC   43620
```

| | | | | | | |
|---|---|---|---|---|---|---|
| CTCTCGACGT | CAACACGCCA | TCTGCTCGCA | TGGAAGCCAT | CATATCGTCC | GTCCCAGGGC | 43680 |
| GTAGGCTCAT | CTTGGTTGGC | TCGGGCGTCC | GCCATGCTGA | TATCAACGTA | CCGAACGCAA | 43740 |
| AGACGATGCT | GATCAGCGAC | ACGGTTACCG | GGACTGATGC | TATTGGCACT | CCCGAACCTC | 43800 |
| TGGTTGTCCG | ACCCAGTGCT | ACAAGTCTCG | CATATGTCAT | CTTCACTTCA | GGGTCAACGG | 43860 |
| GCAAGCCAAA | GGGTGTCATG | GTGGAGCACC | GTGCTATCAT | GCGCCTTGTG | AAGGACAGTA | 43920 |
| ACGTCGTGAC | TCACATGCCA | CCAGCGACAC | GGATGGCCCA | CGTCACGAAT | ATCGCATTCG | 43980 |
| ACGTTTCACT | GTTCGAGATG | TGCGCAACGC | TCCTCAACGG | CGGAACTCTA | GTCTGCATTG | 44040 |
| ACTACCTGAC | CCTTCTTGAC | AGCACCATGC | TCCGGGAGAC | GTTTGAGCGT | GAGCAGGTTC | 44100 |
| GCGCAGCCAT | CTTCCCGCCA | GCACTCCTGC | GACAGTGCTT | GGTCAACATG | CCCGATGCGA | 44160 |
| TCGGCATGTT | AGAGGCTGTT | TACGTTGCCG | GTGATCGCTT | CCACTCCCGC | GACGCCCGCG | 44220 |
| CAACCCAGGC | ACTGGCCGGG | CCTCGTGTGT | ACAACGCGTA | TGGCCCAACT | GAGAACGCAA | 44280 |
| TCCTTAGCAC | GATATATAAC | ATCGATAAGC | ACGATCCGTA | TGTGAACGGT | GTTCCTATCG | 44340 |
| GTAGCGCTGT | CAGCAATTCA | GGGGCCTATG | TCATGGATCG | GAACCAGCAG | CTTCTCCCTC | 44400 |
| CCGGTGTGAT | GGGAGAGCTG | GTTGTTACAG | GAGAGGGTGT | AGCTCGCGGC | TATACCGACG | 44460 |
| CAAGTCTCGA | TACGGACCGC | TTCGTCACCG | TCACGATCGA | TGGCCAGCGC | CAGAGGGCGT | 44520 |
| ACCGCACGGG | TGACCGGGTG | CGATATCGAC | CAAAGGGATT | CCAGATAGAG | TTCTTCGGCC | 44580 |
| GCCTGGACCA | GCAGGCCAAG | ATTCGCGGCC | ACCGTGTTGA | ACTGGGCGAG | GTCGAACATG | 44640 |
| CTCTGCTCAG | CGAGAATTCA | GTCACGGATG | CGGCTGTCGT | ACTCCGCACC | ATGGAAGAGG | 44700 |
| AGGACCCGCA | ACTGGTTGCC | TTTGTGACTA | CTGATCACGA | ATATCGCTCG | GGTTCGAGCA | 44760 |
| ACGAAGAGGA | GGATCCGTAC | GCCACACAGG | CAGCAGGCGA | TATGCGCAAG | CGACTCCGGT | 44820 |
| CGCTTCTGCC | ATACTACATG | GTCCCGTCCC | GGGTCACAAT | ACTCAGGCAA | ATGCCTCTCA | 44880 |
| ACGCCAACGG | CAAGGTGGAC | CGAAAAGACC | TCGCTCGGCG | GGCCCAGATG | ACTCCGACAG | 44940 |
| CAAGCAGCTC | GGGCCCCGTG | CATGTGGCTC | CTCGCAACGA | GACTGAGGCA | GCAATTTGCG | 45000 |
| ACGAGTTCGA | GACTATACTC | GGAGTCAAGG | TGGGAATCAC | AGACAACTTC | TTCGAACTAG | 45060 |
| GCGGGCACTC | ACTCCTGGCC | ACCAAACTCG | CTGCTCGGCT | CAGCCGCCGG | ATGGGCCTTC | 45120 |
| GCATATCCGT | CAAGGATCTG | TTTGACGATC | CTGTTCCTGT | TTCTCTCGCC | GGCAAGCTGG | 45180 |
| AACAACAGCA | GGGGTTCTCG | GGAGAAGATG | AAAGCTCGAC | AGTTGGTATT | GTCCCCTTCC | 45240 |
| AACTCCTCCC | CGCGGAAATG | TCGAGAGAGA | TCATCCAGCG | CGATGTTGTA | CCTCAGATTG | 45300 |
| AGAACGGTCA | CAGCACACCC | CTGGACATGT | ATCCAGCCAC | GCAGACGCAG | ATCTTCTTCC | 45360 |
| TGCACGACAA | AGCGACGGGC | CACCCAGCCA | CGCCGCCACT | GTTCTCCTTG | GACTTCCCCG | 45420 |
| AGACCGCCGA | CTGCCGTCGT | CTGGCAAGCG | CCTGCGCCGC | TCTCGTCCAG | CACTTTGACA | 45480 |
| TATTCAGAAC | CGTGTTCGTG | TCAAGAGGCG | GCCGCTTCTA | CCAAGTTGTT | CTTGCTCATC | 45540 |
| TCGATGTACC | TGTCGAGGTC | ATCGAGACCG | AGCAAGAGTT | GGATGAGGTT | GCTCTCGCGC | 45600 |
| TGCATGAAGC | AGACAAGCAG | CAGCCCCTAC | GTCTGGGACG | TGCGATGCTG | CGGATCGCCA | 45660 |
| TCCTCAAGAG | ACCGGGAGCC | AAGATGCGAC | TTGTTCTCCG | AATGTCTCAT | TCCCTGTACG | 45720 |
| ACGGCTTGAG | TCTTGAACAC | ATCGTCAACG | CTCTACATGC | CTTGTACAGT | GATAAGCACC | 45780 |
| TTGCGCAAGC | ACCCAAGTTT | GGTCTCTACA | TGCATCACAT | GGCTAGCCGA | CGTGCAGAGG | 45840 |
| GCTACAATTT | CTGGCGATCT | ATTCTTCAGG | GCTCTTCAAT | GACATCCCTG | AAGCGCTCTG | 45900 |
| TCGGCGCCCT | CGAGGCCATG | ACGCCGTCTG | CCGGTACATG | GCAGACGTCA | AAGTCCATCA | 45960 |
| GGATCCCTCC | TGCGGCACTC | AAGAACGGCA | TTACGCAGGC | GACCCTCTTC | ACCGCCGCCG | 46020 |

-continued

```
TCTCTCTCTT GCTCGCCAAG CATACCAAGT CGACAGACGT CGTCTTCGGC CGCGTCGTAT    46080

CTGGACGACA GGATCTCTCC ATAAACTGCC AAGACATCGT GGGACCTTGC ATCAACGAGG    46140

TGCCTGTGCG CGTTCGGATC GACGAGGGCG ACGACATGGG TGGTCTGCTG CGCGCCATTC    46200

AAGACCAGTA CACCAGCAGC TTCCGGCACG AGACCTTGGG CTTGCAAGAA GTGAAGGAGA    46260

ACTGCACGGA CTGGACTGAT GCGACCAAGG AGTTCAGTTG CTGCATTGCC TTCCAGAACC    46320

TCAACCTGCA TCCTGAGGCC GAGATTGAAG GGCAGCAGAT TCGCCTGGAG GGTTTGCCAG    46380

CAAAGGATCA AGCACGCCAG GCCAATGGTC ATGCCCAAA TGGCACGAAC GGCACGAATG     46440

GCACGAATGG CACGAATGGC GCGAACGGCA CGAATGGCAC GAATGGCACG AATGGTACCC    46500

ATGCCAACGG TATCAATGGT AGCAACGGTG TCAATGGCCG CGATAGCAAC GTGGTTTCAG    46560

CCGCTGGCGA TCAAGCTCCT GTTCACGATC TGGACATTGT TGGGATTCCG GAGCCCGACG    46620

GCAGCGTCAA GATTGGCATT GGTGCGAGCC GGCAGATCCT TGGAGAAG GTCGTGGGCA      46680

GCATGCTCAA TGAACTTTGC GAGACCATGC TCGCTTTGAG CAGAACATAG CAGCTTTTCC    46740

AGGGAGATTG GTTGGATGGA CAAGATTCTC TTCAATTATG GAGGTTGGCA TGAGGCAACA    46800

GGAGGACTAC TGACTTTTCA TGTTTTTTGG GGTTTTTTGG GGTTTTCTTT TTCCTTTCAT    46860

CTTTACTTGA TGCGCGATGT CTGCTTTCCT CTAGAATTC                           46899
```

( 2 ) INFORMATION FOR SEQ ID NO:2:

( i ) SEQUENCE CHARACTERISTICS:
        ( A ) LENGTH: 15281 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Tolypocladium niveum
        ( B ) STRAIN: ATCC 34921

( x i ) SEQUENCE DESCRIPTION: SEQ ID NO:2:

```
Met Gly Ala Ile Gly Gln Asp Met Ala Tyr Asp Arg Leu Ala Asn Pro
 1               5                  10                  15

Ser Arg Ala Ser Ser Ile Ser Ser Asn Arg Tyr Ser Glu Pro Val Glu
            20                  25                  30

Gln Ser Phe Ala Gln Gly Arg Leu Trp Phe Leu His Gln Leu Lys Leu
        35                  40                  45

Gly Ala Ser Trp Asp Ile Thr Pro Ala Ala Ile Arg Leu Arg Gly His
    50                  55                  60

Leu Asp Ile Asp Ala Leu Asn Ala Ala Ser Arg Ala Leu Thr Gln Arg
65                  70                  75                  80

His Glu Thr Leu Arg Thr Thr Phe Lys Glu Gln Asp Gly Val Gly Val
                85                  90                  95

Gln Val Val His Ala Ser Gly Leu Glu Arg Gly Leu Arg Ile Val Asp
            100                 105                 110

Ala Ser Ser Arg Asp Leu Ala Gln Leu Leu Ala Glu Glu Gln Thr Met
        115                 120                 125

Lys Phe Asp Leu Glu Ser Glu Pro Ala Trp Arg Val Ala Leu Leu Lys
    130                 135                 140

Val Ala Glu Asp His His Ile Leu Ser Ile Val Val His His Ile Ile
```

-continued

|     | 145 |     |     |     | 150 |     |     |     | 155 |     |     |     | 160 |
|-----|-----|-----|-----|-----|-----|-----|-----|-----|-----|-----|-----|-----|-----|

Ser Asp Ser Arg Ser Leu Asp Ile Ile Gln Glu Leu Gly Glu Leu
                165             170             175

Tyr Thr Ala Ala Ser Gln Gly Lys Ser Ile Ser Ala Cys Pro Leu Gly
            180             185             190

Pro Ile Pro Ile Gln Tyr Arg Asp Leu Thr Thr Trp Gln Asn Gln Asp
            195             200             205

Glu Gln Val Ala Glu Gln Arg Gln Leu Gly Tyr Trp Ile Glu Gln
    210             215             220

Leu Asp Asn Asn Thr Pro Ala Glu Leu Leu Thr Glu Leu Pro Arg Pro
225             230             235             240

Ala Ile Pro Ser Gly Glu Thr Gly Lys Ile Ser Phe Gln Ile Asp Gly
                245             250             255

Ser Val His Lys Glu Leu Leu Ala Phe Cys Arg Ser Gln Gln Val Thr
            260             265             270

Ala Tyr Ala Val Leu Leu Ala Ala Phe Arg Val Ala His Phe Arg Leu
        275             280             285

Thr Gly Ala Glu Asp Ala Thr Ile Gly Ala Pro Val Ala Asn Arg Asp
    290             295             300

Arg Pro Glu Leu Glu Asn Met Val Ala Pro Leu Ala Thr Leu Gln Cys
305             310             315             320

Met Arg Val Val Leu Asp Glu Asp Thr Phe Glu Ser Val Leu Arg
                325             330             335

Gln Ile Met Ser Val Met Thr Glu Ala His Ala Asn Arg Asp Val Pro
            340             345             350

Phe Glu Arg Ile Val Ser Ala Leu Leu Pro Gly Ser Thr Asp Thr Ser
        355             360             365

Arg His Pro Leu Val Gln Leu Met Phe Ala Leu His Pro Ala Gln Asp
    370             375             380

Thr Gly Arg Ala Arg Trp Gly Phe Leu Glu Ala Glu Thr Leu Gln Ser
385             390             395             400

Ala Ala Pro Thr Arg Phe Asp Met Glu Met His Leu Phe Glu Gly Asp
                405             410             415

Asp Arg Phe Asp Ala Asn Val Leu Phe Ser Thr Gly Leu Phe Asp Ala
            420             425             430

Glu Ala Ile Arg Ser Val Val Ser Ile Phe Arg Glu Val Leu Arg Arg
        435             440             445

Gly Ile Ser Glu Pro Ala Val His Val Lys Thr Met Pro Leu Thr Asp
    450             455             460

Gly Leu Ala Ala Ile Arg Asp Met Gly Leu Leu Asp Ile Gly Thr Thr
465             470             475             480

Asp Tyr Pro Arg Glu Ala Ser Val Val Asp Met Phe Gln Glu Gln Val
                485             490             495

Ala Leu Asn Pro Ser Ala Thr Ala Val Ala Asp Ala Ser Ser Arg Leu
            500             505             510

Ser Tyr Ser Glu Leu Asp His Lys Ser Asp Gln Leu Ala Ala Trp Leu
        515             520             525

Arg Arg Arg Gln Leu Lys Pro Glu Thr Leu Ile Gly Val Leu Ser Pro
    530             535             540

Pro Ser Cys Glu Thr Met Val Ser Phe Leu Gly Ile Leu Lys Ala His
545             550             555             560

Leu Ala Tyr Leu Pro Leu Asp Ile Asn Val Pro Leu Ala Arg Ile Glu
                565             570             575

```
Ser  Ile  Leu  Ser  Ala  Val  Asp  Gly  His  Lys  Leu  Val  Leu  Leu  Gly  Ser
               580                 585                          590

Asn  Val  Pro  Gln  Pro  Lys  Val  Asp  Val  Pro  Asp  Val  Glu  Leu  Leu  Arg
               595                 600                 605

Ile  Ser  Asp  Ala  Leu  Asn  Gly  Ser  Gln  Val  Asn  Gly  Leu  Ala  Gly  Lys
     610                      615                     620

Gln  Ala  Thr  Ala  Lys  Pro  Ser  Ala  Thr  Asp  Leu  Ala  Tyr  Val  Ile  Phe
625                      630                      635                       640

Thr  Ser  Gly  Ser  Thr  Gly  Lys  Pro  Lys  Gly  Val  Met  Ile  Glu  His  Arg
                    645                 650                           655

Gly  Ile  Val  Arg  Leu  Val  Lys  Gly  Thr  Asn  Ile  Ile  Ser  Pro  Ala  Gln
                    660                 665                      670

Ala  Ala  Val  Pro  Thr  Ala  His  Leu  Ala  Asn  Ile  Ala  Phe  Asp  Leu  Ser
               675                 680                           685

Thr  Trp  Glu  Ile  Tyr  Thr  Pro  Ile  Leu  Asn  Gly  Gly  Thr  Leu  Val  Cys
     690                      695                      700

Ile  Glu  His  Ser  Val  Thr  Leu  Asp  Ser  Lys  Ala  Leu  Glu  Ala  Val  Phe
705                           710                 715                       720

Thr  Lys  Glu  Gly  Ile  Arg  Val  Ala  Phe  Leu  Ala  Pro  Ala  Leu  Ile  Lys
                    725                 730                           735

Gln  Cys  Leu  Ala  Asp  Arg  Pro  Ala  Ile  Phe  Ala  Gly  Leu  Asp  Ser  Leu
               740                      745                      750

Tyr  Ala  Ile  Gly  Asp  Arg  Phe  Asp  Arg  Arg  Asp  Ala  Leu  His  Ala  Lys
          755                      760                           765

Ser  Leu  Val  Lys  His  Gly  Val  Tyr  Asn  Ala  Tyr  Gly  Pro  Thr  Glu  Asn
     770                      775                      780

Ser  Val  Val  Ser  Thr  Ile  Tyr  Ser  Val  Ser  Glu  Ala  Ser  Pro  Phe  Val
785                      790                      795                       800

Thr  Gly  Val  Pro  Val  Gly  Arg  Ala  Ile  Ser  Asn  Ser  Gly  Ala  Tyr  Val
               805                      810                           815

Met  Asp  Gln  Asp  Gln  Gln  Leu  Val  Ser  Pro  Gly  Val  Met  Gly  Glu  Leu
               820                 825                      830

Val  Val  Ser  Gly  Asp  Gly  Leu  Ala  Arg  Gly  Tyr  Thr  Asp  Ser  Ala  Leu
          835                      840                      845

Asp  Lys  Asn  Arg  Phe  Val  Val  Gln  Ile  Asp  Gly  Glu  Ser  Ile  Arg
850                           855                 860

Gly  Tyr  Arg  Thr  Gly  Asp  Arg  Ala  Arg  Tyr  Ser  Leu  Lys  Gly  Gly  Gln
865                      870                 875                           880

Ile  Glu  Phe  Phe  Gly  Arg  Met  Asp  Gln  Gln  Val  Lys  Ile  Arg  Gly  His
                    885                 890                           895

Arg  Ile  Glu  Pro  Ala  Glu  Val  Glu  His  Ala  Leu  Leu  Asn  Ser  Asp  Gln
               900                 905                      910

Val  Arg  Asp  Ala  Ala  Val  Val  Ile  Arg  Arg  Gln  Glu  Glu  Glu  Pro
          915                 920                 925

Ala  Met  Ile  Ala  Phe  Val  Thr  Thr  Gln  Gly  Thr  Leu  Pro  Asp  His  Leu
     930                 935                      940

Val  Asn  Ile  Asn  Gly  Asn  Gly  His  Val  Pro  Asp  Gly  Asn  Gly  Ser  Lys
945                      950                 955                           960

Asn  Asp  Gln  Phe  Ala  Val  His  Val  Glu  Ser  Glu  Leu  Arg  Arg  Arg  Leu
               965                      970                           975

Gln  Met  Leu  Leu  Pro  Ser  Tyr  Met  Met  Pro  Ala  Arg  Ile  Val  Val  Leu
               980                 985                           990

Asp  His  Leu  Pro  Leu  Asn  Pro  Asn  Gly  Lys  Val  Asp  Arg  Lys  Ala  Leu
               995                      1000                     1005
```

```
Gly Gln Ser Ala Lys Thr Val Gln Lys Ser Lys Leu Val Ser Gln Arg
        1010                1015                1020
Val Ala Pro Arg Asn Glu Ile Glu Ala Val Leu Cys Glu Glu Tyr Arg
1025                1030                1035                1040
Ser Val Leu Gly Val Glu Val Gly Ile Thr Asp Asn Phe Phe Asp Leu
                1045                1050                1055
Gly Gly His Ser Leu Thr Ala Met Lys Leu Ala Ala Arg Ile Ser Gln
        1060                1065                1070
Arg Leu Asp Ile Gln Ala Ser Val Ala Thr Val Phe Glu Gln Pro Met
        1075                1080                1085
Leu Ala Asp Leu Ala Ala Thr Ile Gln Arg Gly Ser Thr Leu Tyr Ser
        1090                1095                1100
Val Ile Pro Thr Thr Glu Tyr Thr Gly Pro Val Glu Gln Ser Phe Ala
1105                1110                1115                1120
Gln Gly Arg Leu Trp Phe Leu Glu Gln Leu Asn Thr Gly Ala Ser Trp
                1125                1130                1135
Tyr Asn Val Met Leu Thr Val Arg Leu Arg Gly His Leu Asp Val Asp
                1140                1145                1150
Ala Leu Gly Thr Ala Leu Leu Ala Leu Glu Lys Arg His Glu Thr Leu
        1155                1160                1165
Arg Thr Thr Phe Glu Glu Arg Asp Gly Val Gly Met Gln Val Val His
        1170                1175                1180
Ser Ser Leu Met Gly Glu Leu Arg Leu Ile Asp Ile Ser Glu Lys Ser
1185                1190                1195                1200
Gly Thr Ala Ala His Glu Ala Leu Met Lys Glu Gln Ser Thr Arg Phe
                1205                1210                1215
Asp Leu Thr Arg Glu Pro Gly Trp Arg Val Ala Leu Leu Lys Leu Ala
        1220                1225                1230
Asp His His Ile Phe Ser Ile Val Met His His Ile Val Ser Asp Gly
        1235                1240                1245
Trp Ser Leu Asp Leu Leu Arg His Glu Leu Gly Gln Leu Tyr Ser Ala
        1250                1255                1260
Ala Leu Arg Gly Gln Asp Pro Leu Ser Arg Leu Glu Pro Leu Pro Ile
1265                1270                1275                1280
Gln Tyr Arg Asp Phe Ala Val Trp Gln Lys Gln Asp Ser Gln Gln Lys
                1285                1290                1295
Ala Ala His Gln Arg Gln Leu Glu Tyr Trp Thr Lys Gln Leu Ala Asp
                1300                1305                1310
Ser Thr Pro Ala Glu Leu Leu Thr Asp Phe Pro Arg Pro Ser Ile Leu
        1315                1320                1325
Ser Gly Lys Ala Gly Lys Val Pro Val Ala Ile Glu Gly Ser Leu Tyr
        1330                1335                1340
Asp Thr Leu Gln Val Phe Ser Arg Thr His Gln Val Thr Ser Phe Ala
1345                1350                1355                1360
Val Leu Leu Ala Ala Phe Arg Ala Ala His Phe Arg Leu Thr Gly Ser
                1365                1370                1375
Asp Asn Ala Thr Ile Gly Val Pro Ser Ala Asn Arg Asn Arg Pro Glu
                1380                1385                1390
Leu Glu Asn Val Ile Gly Phe Phe Val Asn Thr Gln Cys Ile Arg Ile
        1395                1400                1405
Thr Ile Asp Glu Asn Asp Asn Phe Glu Ser Leu Val Arg Gln Val Arg
        1410                1415                1420
Ser Thr Thr Thr Ala Ala Gln Asp Asn Gln Asp Val Pro Phe Glu Gln
```

```
1425                1430                1435                1440
Val Val Ser Ser Leu Met Pro Ser Ser Ser Arg Asp Ala Ser Arg Asn
                1445                1450                1455
Pro Leu Val Gln Leu Met Phe Ala Leu His Gly Gln Gln Asp Leu Phe
                1460                1465                1470
Lys Ile Gln Leu Glu Gly Thr Glu Glu Val Ile Pro Thr Glu Glu
            1475                1480                1485
Val Thr Arg Phe Asp Ile Glu Phe His Leu Tyr Gln Gly Ala Ser Lys
                1490                1495                1500
Leu Ser Gly Asp Ile Ile Phe Ala Ala Asp Leu Phe Glu Ala Glu Thr
1505                1510                1515                1520
Ile Arg Gly Val Val Ser Val Phe Gln Glu Val Leu Arg Arg Gly Leu
                1525                1530                1535
Gln Gln Pro Gln Thr Pro Ile Met Thr Met Pro Leu Thr Asp Gly Ile
                1540                1545                1550
Pro Glu Leu Glu Arg Met Gly Leu Leu His Met Val Lys Thr Asp Tyr
1555                1560                1565
Pro Arg Asn Met Ser Val Val Asp Val Phe Gln Gln Val Arg Leu
            1570                1575                1580
Ser Ala Glu Ala Thr Ala Val Ile Asp Ser Ser Arg Met Ser Tyr
1585                1590                1595                1600
Ala Glu Leu Asp Gln Arg Ser Asp Gln Val Ala Ala Trp Leu Arg Gln
                1605                1610                1615
Arg Gln Leu Pro Ala Glu Thr Phe Val Ala Val Leu Ala Pro Arg Ser
                1620                1625                1630
Cys Glu Ala Val Ile Ala Leu Phe Gly Ile Leu Lys Ala Gly His Ala
            1635                1640                1645
Tyr Leu Pro Leu Asp Val Asn Val Pro Ala Ala Arg Leu Arg Ala Ile
            1650                1655                1660
Leu Ala Glu Val Lys Gly Glu Lys Leu Val Leu Leu Gly Ala Gly Glu
1665                1670                1675                1680
Pro Ser Pro Glu Gly Gln Ser Pro Glu Val Ser Ile Val Arg Ile Ala
                1685                1690                1695
Asp Ala Thr Ser Pro Ala Gly His Ala Ser Leu Arg Asp Gly Lys Ser
                1700                1705                1710
Lys Pro Thr Ala Gly Ser Leu Ala Tyr Val Ile Phe Thr Ser Gly Ser
            1715                1720                1725
Thr Gly Lys Pro Lys Gly Val Met Ile Glu His Arg Gly Val Leu Arg
            1730                1735                1740
Leu Val Lys Gln Thr Asn Ile Leu Ser Ser Leu Pro Pro Ala Gln Thr
1745                1750                1755                1760
Phe Arg Met Ala His Met Ser Asn Leu Ala Phe Asp Ala Ser Ile Trp
                1765                1770                1775
Glu Val Phe Thr Ala Leu Leu Asn Gly Gly Ser Leu Val Cys Ile Asp
            1780                1785                1790
Arg Phe Thr Ile Leu Asp Ala Gln Ala Leu Glu Ala Leu Phe Leu Arg
            1795                1800                1805
Glu His Ile Asn Ile Ala Leu Phe Pro Pro Ala Leu Leu Lys Gln Cys
            1810                1815                1820
Leu Thr Asp Ala Ala Ala Thr Ile Lys Ser Leu Asp Leu Leu Tyr Val
1825                1830                1835                1840
Gly Gly Asp Arg Leu Asp Thr Ala Asp Ala Ala Leu Ala Lys Ala Leu
                1845                1850                1855
```

```
Val Lys Ser Glu Val Tyr Asn Ala Tyr Gly Pro Thr Glu Asn Thr Val
            1860                1865                1870

Met Ser Thr Leu Tyr Ser Ile Ala Asp Thr Glu Arg Phe Val Asn Gly
            1875                1880                1885

Val Pro Ile Gly Arg Ala Val Ser Asn Ser Gly Val Tyr Val Met Asp
        1890                1895                1900

Gln Asn Gln Gln Leu Val Pro Leu Gly Val Met Gly Glu Leu Val Val
1905                1910                1915                1920

Thr Gly Asp Gly Leu Ala Arg Gly Tyr Thr Asn Pro Ala Leu Asp Ser
            1925                1930                1935

Asp Arg Phe Val Asp Val Ile Ala Arg Gly Gln Leu Leu Arg Ala Tyr
            1940                1945                1950

Arg Thr Gly Asp Arg Ala Arg Tyr Arg Pro Lys Asp Gly Gln Val Glu
            1955                1960                1965

Phe Phe Gly Arg Met Asp His Gln Val Lys Val Arg Gly His Arg Ile
            1970                1975                1980

Glu Leu Ala Glu Val Glu His Ala Leu Leu Ser Ser Ala Gly Val His
1985                1990                1995                2000

Asp Ala Val Val Val Ser Asn Ser Gln Glu Asp Asn Gln Gly Val Glu
            2005                2010                2015

Met Val Ala Phe Ile Thr Ala Gln Asp Asn Glu Thr Leu Gln Glu Ala
            2020                2025                2030

Gln Ser Ser Asn Gln Val Gln Glu Trp Glu Ser His Phe Glu Thr Thr
            2035                2040                2045

Ala Tyr Ala Asp Ile Thr Ala Ile Asp Gln Asn Thr Leu Gly Arg Asp
            2050                2055                2060

Phe Thr Ser Trp Thr Ser Met Tyr Asp Gly Thr Leu Ile Asp Lys Arg
2065                2070                2075                2080

Glu Met Gln Glu Trp Leu Asp Asp Thr Met Arg Thr Phe Leu Asp Gly
            2085                2090                2095

Gln Ala Ala Gly His Val Leu Glu Ile Gly Thr Gly Thr Gly Met Val
            2100                2105                2110

Leu Phe Asn Leu Gly Gln Ala Gly Leu Lys Ser Tyr Ile Gly Leu Glu
            2115                2120                2125

Pro Ser Gln Ser Ala Val Gln Phe Val Asn Lys Ala Ala Gln Thr Phe
            2130                2135                2140

Pro Gly Leu Glu Gly Lys Ala Gln Val His Val Gly Thr Ala Met Asp
2145                2150                2155                2160

Thr Gly Arg Leu Ser Ala Leu Ser Pro Asp Leu Ile Val Ile Asn Ser
            2165                2170                2175

Val Ala Gln Tyr Phe Pro Ser Arg Glu Tyr Leu Ala Glu Val Val Glu
            2180                2185                2190

Ala Leu Val Arg Ile Pro Gly Val Arg Arg Ile Phe Phe Gly Asp Met
            2195                2200                2205

Arg Thr Tyr Ala Thr His Lys Asp Phe Leu Val Ala Arg Ala Val His
            2210                2215                2220

Thr Asn Gly Ser Lys Val Thr Arg Ser Lys Val Gln Gln Glu Val Ala
2225                2230                2235                2240

Arg Leu Glu Glu Leu Glu Glu Glu Leu Leu Val Asp Pro Ala Phe Phe
            2245                2250                2255

Thr Ser Leu Lys Glu Ser Leu Ser Glu Glu Ile Glu His Val Glu Ile
            2260                2265                2270

Leu Pro Lys Asn Met Lys Val Asn Asn Glu Leu Ser Ser Tyr Arg Tyr
            2275                2280                2285
```

```
Gly Ala Val Leu His Ile Arg Asn His Asn Gln Asn Gln Ser Arg Ser
        2290                2295                2300
Ile His Lys Ile Asn Ala Glu Ser Trp Ile Asp Phe Ala Ser Ser Gln
2305                2310                2315                2320
Met Asp Arg Gln Gly Leu Ala Arg Leu Leu Lys Glu Asn Lys Asp Ala
            2325                2330                2335
Glu Ser Ile Ala Val Phe Asn Ile Pro Tyr Ser Lys Thr Ile Val Glu
            2340                2345                2350
Arg His Ile Ala Lys Ser Leu Ala Asp His Asp Gly Asp Asp Thr
            2355                2360                2365
His Ser Ser Ile Asp Gly Val Ala Trp Ile Ser Ala Ala Arg Glu Lys
        2370                2375                2380
Ala Ser Gln Cys Pro Ser Leu Asp Val His Asp Leu Val Gln Leu Ala
2385                2390                2395                2400
Glu Asp Ala Gly Phe Arg Val Glu Val Ser Trp Ala Arg Gln Arg Ser
            2405                2410                2415
Gln Asn Gly Ala Leu Asp Val Phe Phe His His Phe Gln Pro Thr Glu
            2420                2425                2430
Asn Glu Ser Arg Ala Leu Val Asp Phe Pro Thr Asp Tyr Lys Gly Gln
            2435                2440                2445
Gln Ala Arg Ser Leu Thr Asn Arg Pro Leu Gln Arg Val Glu Ser Arg
        2450                2455                2460
Arg Ile Glu Ala Gln Val Arg Glu Gln Leu Gln Val Leu Leu Pro Ala
2465                2470                2475                2480
Tyr Met Ile Pro Ala Arg Ile Val Val Leu Gln Asn Met Pro Leu Asn
            2485                2490                2495
Thr Ser Gly Lys Val Asp Arg Lys Glu Leu Thr Leu Arg Ala Lys Val
            2500                2505                2510
Thr Ala Ala Arg Thr Pro Ser Ser Glu Leu Val Ala Pro Arg Asp Ser
            2515                2520                2525
Ile Glu Ala Ile Ile Cys Lys Glu Phe Lys Asp Val Leu Gly Val Glu
            2530                2535                2540
Val Gly Ile Thr Asp Asn Phe Phe Asn Val Gly Gly His Ser Leu Leu
2545                2550                2555                2560
Ala Thr Lys Leu Ala Ala Arg Leu Ser Arg Gln Leu Asn Ala Gln Ile
            2565                2570                2575
Ala Val Lys Asp Ile Phe Asp Arg Pro Val Ile Ala Asp Leu Ala Ala
            2580                2585                2590
Thr Ile Gln Gln Asp Thr Thr Glu His Asn Pro Ile Leu Pro Thr Ser
            2595                2600                2605
Tyr Thr Gly Pro Val Glu Gln Ser Phe Ala Gln Gly Arg Leu Trp Phe
        2610                2615                2620
Leu Asp Gln Leu Asn Val Gly Ala Thr Trp Tyr Leu Met Pro Phe Ala
2625                2630                2635                2640
Val Arg Leu Arg Gly Pro Leu Val Val Ser Ala Leu Ala Ala Ala Leu
            2645                2650                2655
Leu Ala Leu Glu Glu Arg His Glu Thr Leu Arg Thr Thr Phe Ile Glu
            2660                2665                2670
Gln Glu Gly Ile Gly Met Gln Val Ile His Pro Phe Ala Pro Lys Glu
            2675                2680                2685
Leu Arg Val Ile Asp Val Ser Gly Glu Glu Ser Thr Ile Gln Lys
        2690                2695                2700
Ile Leu Glu Lys Glu Gln Thr Thr Pro Phe Asn Leu Ala Ser Glu Pro
```

```
    2705                 2710                 2715                 2720
Gly Phe Arg Leu Ala Leu Leu Lys Thr Gly Glu Asp Glu His Ile Leu
                2725                 2730                 2735
Ser Thr Val Met His His Ala Ile Ser Asp Gly Trp Ser Val Asp Ile
                2740                 2745                 2750
Phe Gln Gln Glu Ile Gly Gln Phe Tyr Ser Ala Ile Leu Arg Gly His
                2755                 2760                 2765
Asp Pro Leu Ala Gln Ile Ala Pro Leu Ser Ile Gln Tyr Arg Asp Phe
                2770                 2775                 2780
Ala Thr Trp Gln Arg Gln Ile Phe Gln Val Ala Glu His Arg Arg Gln
2785                 2790                 2795                 2800
Leu Ala Tyr Trp Thr Lys Gln Leu Ala Asp Asn Lys Pro Ala Glu Leu
                2805                 2810                 2815
Leu Thr Asp Phe Lys Arg Pro Pro Met Leu Ser Gly Arg Ala Gly Glu
                2820                 2825                 2830
Ile Pro Val Val Val Asp Gly Leu Ile Tyr Glu Lys Leu Gln Asp Phe
                2835                 2840                 2845
Cys Arg Ile Arg Gln Val Thr Ala Phe Thr Val Leu Leu Ala Ala Phe
                2850                 2855                 2860
Arg Ala Ala His Tyr Arg Met Thr Gly Thr Glu Asp Ala Thr Ile Gly
2865                 2870                 2875                 2880
Thr Pro Ile Ala Asn Arg Asn Arg Pro Glu Leu Glu Gly Leu Ile Gly
                2885                 2890                 2895
Phe Phe Val Asn Thr Gln Cys Met Arg Ile Thr Val Asp Val Glu Asp
                2900                 2905                 2910
Ser Phe Glu Thr Leu Val His Gln Val Arg Glu Thr Thr Leu Ala Ala
                2915                 2920                 2925
His Ala Asn Gln Asp Val Pro Phe Glu Gln Ile Val Ser Asn Ile Leu
                2930                 2935                 2940
Pro Gly Ser Ser Asp Thr Ser Arg Asn Pro Leu Val Gln Leu Met Phe
2945                 2950                 2955                 2960
Ala Leu His Ser Gln Gln Asn Leu Gly Lys Val Arg Leu Glu Gly Ile
                2965                 2970                 2975
Glu Glu Glu Ile Ile Ser Ile Ala Glu Thr Thr Arg Phe Asp Ile Glu
                2980                 2985                 2990
Phe His Leu Tyr Gln Glu Ala Glu Arg Leu Asn Gly Ser Ile Val Tyr
                2995                 3000                 3005
Ala Ala Asp Leu Phe Val Pro Glu Thr Ile Gln Ser Val Ile Thr Ile
                3010                 3015                 3020
Phe Gln Gly Ile Leu Gln Lys Gly Leu Gly Glu Pro Asp Met Pro Val
3025                 3030                 3035                 3040
Ala Ser Met Ala Leu Asp Gly Gly Leu Glu Ser Leu Arg Ser Thr Gly
                3045                 3050                 3055
Leu Leu His Pro Gln Gln Thr Asp Tyr Pro Cys Asp Ala Ser Val Val
                3060                 3065                 3070
Gln Ile Phe Lys Gln Gln Val Ala Val Asn Pro Asp Val Ile Ala Val
                3075                 3080                 3085
Arg Asp Glu Ser Thr Arg Leu Ser Tyr Ala Asp Leu Asp Arg Lys Ser
                3090                 3095                 3100
Asp Gln Val Ala Cys Trp Leu Ser Arg Arg Gly Ile Ala Pro Glu Thr
3105                 3110                 3115                 3120
Phe Val Ala Ile Leu Ala Pro Arg Ser Cys Glu Thr Ile Val Ala Ile
                3125                 3130                 3135
```

```
Leu Gly Val Leu Lys Ala Asn Leu Ala Tyr Leu Pro Leu Asp Val Asn
            3140                3145                3150

Val Pro Ala Ser Arg Leu Glu Ala Ile Leu Ser Glu Val Ser Gly Ser
        3155                3160                3165

Met Leu Val Leu Val Gly Ala Glu Thr Pro Ile Pro Gly Met Ala
    3170                3175                3180

Glu Ala Glu Thr Ile Arg Ile Thr Glu Ile Leu Ala Asp Ala Lys Thr
3185                3190                3195                3200

Asp Asp Ile Asn Gly Leu Ala Ala Ser Gln Pro Thr Ala Ala Ser Leu
            3205                3210                3215

Ala Tyr Val Ile Phe Thr Ser Gly Ser Thr Gly Arg Pro Lys Gly Val
            3220                3225                3230

Met Val Glu His Arg Gly Ile Val Arg Leu Thr Lys Gln Thr Asn Ile
    3235                3240                3245

Thr Ser Lys Leu Pro Glu Ser Phe His Met Ala His Ile Ser Asn Leu
        3250                3255                3260

Ala Phe Asp Ala Ser Val Trp Glu Val Phe Thr Thr Leu Leu Asn Gly
3265                3270                3275                3280

Gly Thr Leu Val Cys Ile Asp Tyr Phe Thr Leu Leu Glu Ser Thr Ala
            3285                3290                3295

Leu Glu Lys Val Phe Phe Asp Gln Arg Val Asn Val Ala Leu Leu Pro
            3300                3305                3310

Pro Ala Leu Leu Lys Gln Cys Leu Asp Asn Ser Pro Ala Leu Val Lys
            3315                3320                3325

Thr Leu Ser Val Leu Tyr Ile Gly Gly Asp Arg Leu Asp Ala Ser Asp
3330                3335                3340

Ala Ala Lys Ala Arg Gly Leu Val Gln Thr Gln Ala Phe Asn Ala Tyr
3345                3350                3355                3360

Gly Pro Thr Glu Asn Thr Val Met Ser Thr Ile Tyr Pro Ile Ala Glu
            3365                3370                3375

Asp Pro Phe Ile Asn Gly Val Pro Ile Gly His Ala Val Ser Asn Ser
            3380                3385                3390

Gly Ala Phe Val Met Asp Gln Asn Gln Gln Ile Thr Pro Pro Gly Ala
            3395                3400                3405

Met Gly Glu Leu Ile Val Thr Gly Asp Gly Leu Ala Arg Gly Tyr Thr
    3410                3415                3420

Thr Ser Ser Leu Asn Thr Gly Arg Phe Ile Asn Val Asp Ile Asp Gly
3425                3430                3435                3440

Glu Gln Val Arg Ala Tyr Arg Thr Gly Asp Arg Val Arg Tyr Arg Pro
            3445                3450                3455

Lys Asp Leu Gln Ile Glu Phe Phe Gly Arg Ile Asp His Gln Val Lys
            3460                3465                3470

Ile Arg Gly His Arg Ile Glu Pro Ala Glu Val Glu Tyr Ala Leu Leu
        3475                3480                3485

Ser His Asp Leu Val Thr Asp Ala Ala Val Val Thr His Ser Gln Glu
    3490                3495                3500

Asn Gln Asp Leu Glu Met Val Gly Phe Val Ala Ala Arg Val Ala Asp
3505                3510                3515                3520

Val Arg Glu Asp Glu Ser Ser Asn Gln Val Gln Glu Trp Gln Thr His
            3525                3530                3535

Phe Asp Ser Ile Ala Tyr Ala Asp Ile Thr Thr Ile Asp Gln Gln Ser
            3540                3545                3550

Leu Gly Arg Asp Phe Met Ser Trp Thr Ser Met Tyr Asp Gly Ser Leu
            3555                3560                3565
```

Ile Lys Lys Ser Gln Met Gln Glu Trp Leu Asp Asp Thr Met Arg Ser
3570                3575                3580

Leu Leu Asp Ser Gln Pro Pro Gly His Val Leu Glu Val Gly Thr Gly
3585                3590                3595                3600

Thr Gly Met Val Leu Phe Asn Leu Gly Arg Glu Gly Gly Leu Gln Ser
            3605                3610                3615

Tyr Val Gly Leu Glu Pro Ser Pro Ser Ala Thr Ala Phe Val Asn Lys
            3620                3625                3630

Ala Ala Lys Ser Phe Pro Gly Leu Glu Asp Arg Ile Arg Val Glu Val
            3635                3640                3645

Gly Thr Ala Thr Asp Ile Asp Arg Leu Gly Asp Asp Leu His Ala Gly
            3650                3655                3660

Leu Val Val Val Asn Ser Val Ala Gln Tyr Phe Pro Ser Gln Asp Tyr
3665                3670                3675                3680

Leu Ala Gln Leu Val Arg Asp Leu Thr Lys Val Pro Gly Val Glu Arg
                3685                3690                3695

Ile Phe Phe Gly Asp Met Arg Ser His Ala Ile Asn Arg Asp Phe Leu
                3700                3705                3710

Val Ala Arg Ala Val His Ala Leu Gly Asp Lys Ala Thr Lys Ala Glu
            3715                3720                3725

Ile Gln Arg Glu Val Val Arg Met Glu Glu Ser Glu Asp Glu Leu Leu
            3730                3735                3740

Val Asp Pro Ala Phe Phe Thr Ser Leu Thr Thr Gln Val Glu Asn Ile
3745                3750                3755                3760

Lys His Val Glu Ile Leu Pro Lys Arg Met Arg Ala Thr Asn Glu Leu
                3765                3770                3775

Ser Ser Tyr Arg Tyr Ala Ala Val Leu His Val Asn Asp Leu Ala Lys
            3780                3785                3790

Pro Ala His Lys Val Ser Pro Gly Ala Trp Val Asp Phe Ala Ala Thr
            3795                3800                3805

Lys Met Asp Arg Asp Ala Leu Ile Arg Leu Leu Arg Gly Thr Lys Ile
            3810                3815                3820

Ser Asp His Ile Ala Ile Ala Asn Ile Pro Asn Ser Lys Thr Ile Val
3825                3830                3835                3840

Glu Arg Thr Ile Cys Glu Ser Val Tyr Asp Leu Gly Gly Asp Ala Lys
                3845                3850                3855

Asp Ser Asn Asp Arg Val Ser Trp Leu Ser Ala Ala Arg Ser Asn Ala
            3860                3865                3870

Val Lys Val Ala Ser Leu Ser Ala Ile Asp Leu Val Asp Ile Ala Gln
            3875                3880                3885

Glu Ala Gly Phe Arg Val Glu Ile Ser Cys Ala Arg Gln Trp Ser Gln
    3890                3895                3900

Asn Gly Ala Leu Asp Ala Val Phe His His Leu Gly Pro Ser Pro Gln
3905                3910                3915                3920

Ser Ser His Val Leu Ile Asp Phe Leu Thr Asp His Gln Gly Arg Pro
                3925                3930                3935

Glu Glu Ala Leu Thr Asn His Pro Leu His Arg Ala Gln Ser Arg Arg
            3940                3945                3950

Val Glu Arg Gln Ile Arg Glu Arg Leu Gln Thr Leu Leu Pro Ala Tyr
            3955                3960                3965

Met Ile Pro Ala Gln Ile Met Val Leu Asp Lys Leu Pro Leu Asn Ala
3970                3975                3980

Asn Gly Lys Val Asp Arg Lys Gln Leu Thr Gln Arg Ala Gln Thr Val

```
3985                3990                3995                4000
Pro  Lys  Ala  Lys  Gln  Val  Ser  Ala  Pro  Val  Ala  Pro  Arg  Thr  Glu  Ile
               4005                4010                4015
Glu  Arg  Val  Leu  Cys  Gln  Glu  Phe  Ser  Asp  Val  Leu  Gly  Val  Asp  Ile
4020                4025                4030
Gly  Ile  Met  Glu  Asn  Phe  Phe  Asp  Leu  Gly  Gly  His  Ser  Leu  Met  Ala
          4035                4040                4045
Thr  Lys  Leu  Ala  Ala  Arg  Ile  Ser  Arg  Arg  Leu  Glu  Thr  His  Val  Ser
4050                4055                4060
Val  Lys  Glu  Ile  Phe  Asp  His  Pro  Arg  Val  Cys  Asp  Leu  Val  Leu  Ile
4065                4070                4075                4080
Val  Gln  Gln  Gly  Ser  Ala  Pro  His  Asp  Pro  Ile  Val  Ser  Thr  Lys  Tyr
               4085                4090                4095
Thr  Gly  Pro  Val  Pro  Gln  Ser  Phe  Ala  Gln  Gly  Arg  Leu  Trp  Phe  Leu
               4100                4105                4110
Asp  Gln  Leu  Asn  Phe  Gly  Ala  Thr  Trp  Tyr  Leu  Met  Pro  Leu  Ala  Val
               4115                4120                4125
Arg  Leu  Arg  Gly  Ala  Met  Asn  Val  His  Ala  Leu  Thr  Ala  Ala  Leu  Leu
               4130                4135                4140
Ala  Leu  Glu  Arg  Arg  His  Glu  Leu  Leu  Arg  Thr  Thr  Phe  Tyr  Glu  Gln
4145                4150                4155                4160
Asn  Gly  Val  Gly  Met  Gln  Lys  Val  Asn  Pro  Val  Val  Thr  Glu  Thr  Leu
               4165                4170                4175
Arg  Ile  Ile  Asp  Leu  Ser  Asn  Gly  Asp  Gly  Asp  Tyr  Leu  Pro  Thr  Leu
               4180                4185                4190
Lys  Lys  Glu  Gln  Thr  Ala  Pro  Phe  His  Leu  Glu  Thr  Glu  Pro  Gly  Trp
               4195                4200                4205
Arg  Val  Ala  Leu  Leu  Arg  Leu  Gly  Pro  Gly  Asp  Tyr  Ile  Leu  Ser  Val
               4210                4215                4220
Val  Met  His  His  Ile  Ile  Ser  Asp  Gly  Trp  Ser  Val  Asp  Val  Leu  Phe
4225                4230                4235                4240
Gln  Glu  Leu  Gly  Gln  Phe  Tyr  Ser  Thr  Ala  Val  Lys  Gly  His  Asp  Pro
               4245                4250                4255
Leu  Ser  Gln  Thr  Thr  Pro  Leu  Pro  Ile  His  Tyr  Arg  Asp  Phe  Ala  Leu
               4260                4265                4270
Trp  Gln  Lys  Lys  Pro  Thr  Gln  Glu  Ser  Glu  His  Glu  Arg  Gln  Leu  Gln
               4275                4280                4285
Tyr  Trp  Val  Glu  Gln  Leu  Val  Asp  Ser  Ala  Pro  Ala  Glu  Leu  Leu  Thr
               4290                4295                4300
Asp  Leu  Pro  Arg  Pro  Ser  Ile  Leu  Ser  Gly  Gln  Ala  Gly  Glu  Met  Ser
4305                4310                4315                4320
Val  Thr  Ile  Glu  Gly  Ala  Leu  Tyr  Lys  Asn  Leu  Glu  Glu  Phe  Cys  Arg
               4325                4330                4335
Val  His  Arg  Val  Thr  Ser  Phe  Val  Val  Leu  Leu  Ala  Ala  Leu  Arg  Ala
               4340                4345                4350
Ala  His  Tyr  Arg  Leu  Thr  Gly  Ser  Glu  Asp  Ala  Thr  Ile  Gly  Thr  Pro
               4355                4360                4365
Ile  Ala  Asn  Arg  Asn  Arg  Pro  Glu  Leu  Glu  Gln  Ile  Ile  Gly  Phe  Phe
               4370                4375                4380
Val  Asn  Thr  Gln  Cys  Ile  Arg  Ile  Thr  Val  Asn  Glu  Asp  Glu  Thr  Phe
4385                4390                4395                4400
Glu  Ser  Leu  Val  Gln  Gln  Val  Arg  Ser  Thr  Ala  Thr  Ala  Ala  Phe  Ala
               4405                4410                4415
```

His Gln Asp Val Pro Phe Glu Lys Ile Val Ser Thr Leu Leu Pro Gly
                4420                4425                4430

Ser Arg Asp Ala Ser Arg Asn Pro Leu Val Gln Leu Met Phe Ala Val
            4435                4440                4445

His Ser Gln Lys Asn Leu Gly Glu Leu Lys Leu Asn Ala His Ser
        4450                4455                4460

Glu Val Val Pro Thr Glu Ile Thr Thr Arg Phe Asp Leu Glu Phe His
4465                4470                4475                4480

Leu Phe Gln Gln Asp Asp Lys Leu Glu Gly Ser Ile Leu Tyr Ser Thr
                4485                4490                4495

Asp Leu Phe Glu Ala Val Ser Val Gln Ser Leu Leu Ser Val Phe Gln
                4500                4505                4510

Glu Ile Leu Arg Arg Gly Leu Asn Gly Pro Asp Val Pro Ile Ser Thr
            4515                4520                4525

Leu Pro Leu Gln Asp Gly Ile Val Asp Leu Gln Arg Gln Gly Leu Leu
        4530                4535                4540

Asp Val Gln Lys Thr Glu Tyr Pro Arg Asp Ser Ser Val Val Asp Val
4545                4550                4555                4560

Phe His Glu Gln Val Ser Ile Asn Pro Asp Ser Ile Ala Leu Ile His
                4565                4570                4575

Gly Ser Glu Lys Leu Ser Tyr Ala Gln Leu Asp Arg Glu Ser Asp Arg
            4580                4585                4590

Val Ala Arg Trp Leu Arg His Arg Ser Phe Ser Ser Asp Thr Leu Ile
        4595                4600                4605

Ala Val Leu Ala Pro Arg Ser Cys Glu Thr Ile Ile Ala Phe Leu Gly
        4610                4615                4620

Ile Leu Lys Ala Asn Leu Ala Tyr Leu Pro Leu Asp Val Lys Ala Pro
4625                4630                4635                4640

Ala Ala Arg Ile Asp Ala Ile Val Ser Ser Leu Pro Gly Asn Lys Leu
                4645                4650                4655

Ile Leu Leu Gly Ala Asn Val Thr Pro Pro Lys Leu Gln Glu Ala Ala
            4660                4665                4670

Ile Asp Phe Val Pro Ile Arg Asp Thr Phe Thr Thr Leu Thr Asp Gly
        4675                4680                4685

Thr Leu Gln Asp Gly Pro Thr Ile Glu Arg Pro Ser Ala Gln Ser Leu
    4690                4695                4700

Ala Tyr Ala Met Phe Thr Ser Gly Ser Thr Gly Arg Pro Lys Gly Val
4705                4710                4715                4720

Met Val Gln His Arg Asn Ile Val Arg Leu Val Lys Asn Ser Asn Val
                4725                4730                4735

Val Ala Lys Gln Pro Ala Ala Ala Arg Ile Ala His Ile Ser Asn Leu
            4740                4745                4750

Ala Phe Asp Ala Ser Ser Trp Glu Ile Tyr Ala Pro Leu Leu Asn Gly
        4755                4760                4765

Gly Ala Ile Val Cys Ala Asp Tyr Phe Thr Thr Ile Asp Pro Gln Ala
    4770                4775                4780

Leu Gln Glu Thr Phe Gln Glu His Glu Ile Arg Gly Ala Met Leu Pro
4785                4790                4795                4800

Pro Ser Leu Leu Lys Gln Cys Leu Val Gln Ala Pro Asp Met Ile Ser
                4805                4810                4815

Arg Leu Asp Ile Leu Phe Ala Ala Gly Asp Arg Phe Ser Ser Val Asp
            4820                4825                4830

Ala Leu Gln Ala Gln Arg Leu Val Gly Ser Gly Val Phe Asn Ala Tyr
        4835                4840                4845

```
Gly Pro Thr Glu Asn Thr Ile Leu Ser Thr Ile Tyr Asn Val Ala Glu
    4850                4855                4860
Asn Asp Ser Phe Val Asn Gly Val Pro Ile Gly Ser Ala Val Ser Asn
4865                4870                4875                4880
Ser Gly Ala Tyr Ile Met Asp Lys Asn Gln Gln Leu Val Pro Ala Gly
                4885                4890                4895
Val Met Gly Glu Leu Val Val Thr Gly Asp Gly Leu Ala Arg Gly Tyr
        4900                4905                4910
Met Asp Pro Lys Leu Asp Ala Asp Arg Phe Ile Gln Leu Thr Val Asn
            4915                4920                4925
Gly Ser Glu Gln Val Arg Ala Tyr Arg Thr Gly Asp Arg Val Arg Tyr
    4930                4935                4940
Arg Pro Lys Asp Phe Gln Ile Glu Phe Phe Gly Arg Met Asp Gln Gln
4945                4950                4955                4960
Ile Lys Ile Arg Gly His Arg Ile Glu Pro Ala Glu Val Glu Gln Ala
                4965                4970                4975
Phe Leu Asn Asp Gly Phe Val Glu Asp Val Ala Ile Val Ile Arg Thr
            4980                4985                4990
Pro Glu Asn Gln Glu Pro Glu Met Val Ala Phe Val Thr Ala Lys Gly
        4995                5000                5005
Asp Asn Ser Ala Arg Glu Glu Ala Thr Thr Gln Ile Glu Gly Trp
    5010                5015                5020
Glu Ala His Phe Glu Gly Gly Ala Tyr Ala Asn Ile Glu Glu Ile Glu
5025                5030                5035                5040
Ser Glu Ala Leu Gly Tyr Asp Phe Met Gly Trp Thr Ser Met Tyr Asp
                5045                5050                5055
Gly Thr Glu Ile Asp Lys Asp Glu Met Arg Glu Trp Leu Asn Asp Thr
            5060                5065                5070
Met Arg Ser Leu Leu Asp Gly Lys Pro Ala Gly Arg Val Leu Glu Val
        5075                5080                5085
Gly Thr Gly Thr Gly Met Ile Met Phe Asn Leu Gly Arg Ser Gln Gly
    5090                5095                5100
Leu Glu Arg Tyr Ile Gly Leu Glu Pro Ala Pro Ser Ala Ala Glu Phe
5105                5110                5115                5120
Val Asn Asn Ala Ala Lys Ser Phe Pro Gly Leu Ala Gly Arg Ala Glu
                5125                5130                5135
Val His Val Gly Thr Ala Ala Asp Val Gly Thr Leu Gln Gly Leu Thr
            5140                5145                5150
Ser Asp Met Ala Val Ile Asn Ser Val Ala Gln Tyr Phe Pro Thr Pro
        5155                5160                5165
Glu Tyr Leu Ala Glu Thr Ile Lys Ser Leu Val Gln Val Pro Gly Met
    5170                5175                5180
Lys Arg Ile Tyr Leu Gly Asp Met Arg Ser Trp Ala Met Asn Arg Asp
5185                5190                5195                5200
Phe Ala Ala Ala Arg Ala Ala Tyr Ser Leu Ala Asp Asn Ala Ser Lys
                5205                5210                5215
Asp Arg Val Arg Gln Lys Met Met Glu Leu Glu Glu Lys Glu Glu Glu
            5220                5225                5230
Leu Leu Val Asp Pro Ala Phe Phe Thr Ala Leu Ala Ser Gln Leu Gln
        5235                5240                5245
Asp Arg Ile Gln His Val Glu Ile Leu Pro Lys Arg Met Lys Ala Thr
    5250                5255                5260
Asn Glu Leu Ser Ser Tyr Arg Tyr Ala Ala Val Leu His Ile Ser Asp
```

```
           5265                   5270                   5275                   5280
     Glu Pro Leu Pro Ile Tyr Lys Ile Asp Pro Glu Ala Trp Ile Asn Phe
                             5285                   5290                   5295
     Glu Gly Ser Arg Leu Thr Arg Glu Ala Leu Ala Gln Val Leu Lys Glu
                     5300                   5305                   5310
     Asn Glu Asn Ala Glu Ser Val Ala Ile Ser Asn Ile Pro Tyr Ser Lys
                     5315                   5320                   5325
     Thr Val Val Glu Arg His Ile Val Arg Ser Leu Asp Gln Glu Asp Ala
             5330                   5335                   5340
     Asn Ala Pro Glu Glu Ser Met Asp Gly Ser Asp Trp Ile Ser Ala Val
     5345                   5350                   5355                   5360
     Arg Thr Arg Ala Gln Gln Cys His Thr Leu Ser Ala Ser Asp Leu Phe
                             5365                   5370                   5375
     Asp Ile Ala Glu Asp Ala Gly Phe Arg Val Glu Val Ser Trp Ala Arg
                             5380                   5385                   5390
     Gln His Ser Gln His Gly Ala Leu Asp Ala Val Phe His His Leu Lys
                     5395                   5400                   5405
     Pro Ala Thr Glu Asp Ser Arg Val Leu Ile Lys Phe Pro Thr Asp His
                     5410                   5415                   5420
     Gln Gly Arg Pro Leu Lys Ser Leu Thr Asn Gln Pro Leu Leu Pro Ala
     5425                   5430                   5435                   5440
     Gln Ser Arg Arg Ala Glu Leu Leu Ile Arg Glu Gly Leu Gln Thr Leu
                             5445                   5450                   5455
     Leu Pro Pro Tyr Met Ile Pro Ser Gln Ile Thr Leu Ile Asp Arg Met
                             5460                   5465                   5470
     Pro Leu Asn Ala Asn Gly Lys Val Asp Arg Arg Glu Leu Ala Arg Arg
                             5475                   5480                   5485
     Ala Lys Ile Thr Gln Lys Ser Lys Pro Val Glu Asp Ile Val Pro Pro
                     5490                   5495                   5500
     Arg Asn Ser Val Glu Ala Thr Val Cys Lys Gly Phe Thr Asp Val Leu
     5505                   5510                   5515                   5520
     Gly Val Glu Val Gly Ile Thr Asp Asn Phe Phe Asn Leu Gly Gly His
                             5525                   5530                   5535
     Ser Leu Met Ala Thr Lys Leu Ala Ala Arg Leu Gly Arg Gln Leu Asn
                     5540                   5545                   5550
     Thr Arg Ile Ser Val Arg Asp Val Phe Asp Gln Pro Val Val Ala Asp
                     5555                   5560                   5565
     Leu Ala Ala Val Ile Gln Arg Asn Ser Ala Pro His Glu Pro Ile Lys
                     5570                   5575                   5580
     Pro Ala Asp Tyr Thr Gly Pro Val Pro Gln Ser Phe Ala Gln Gly Arg
     5585                   5590                   5595                   5600
     Leu Trp Phe Leu Asp Gln Leu Asn Val Gly Ala Thr Trp Tyr Leu Met
                             5605                   5610                   5615
     Pro Leu Gly Ile Arg Leu His Gly Ser Leu Arg Val Asp Ala Leu Ala
                     5620                   5625                   5630
     Thr Ala Ile Ser Ala Leu Glu Gln Arg His Glu Pro Leu Arg Thr Thr
                     5635                   5640                   5645
     Phe His Glu Glu Asp Gly Val Gly Val Gln Val Val Gln Asp His Arg
                     5650                   5655                   5660
     Pro Lys Asp Leu Arg Ile Ile Asp Leu Ser Thr Gln Pro Lys Asp Ala
     5665                   5670                   5675                   5680
     Tyr Leu Ala Val Leu Lys His Glu Gln Thr Thr Leu Phe Asp Leu Ala
                             5685                   5690                   5695
```

```
Thr Glu Pro Gly Trp Arg Val Ala Leu Ile Arg Leu Gly Glu Glu
            5700              5705                  5710
His Ile Leu Ser Ile Val Met His His Ile Ile Ser Asp Gly Trp Ser
            5715              5720                  5725
Val Glu Val Leu Phe Asp Met His Arg Phe Tyr Ser Ser Ala Leu
    5730              5735                  5740
Arg Gln Gln Asp Pro Met Glu Gln Ile Leu Pro Leu Pro Ile Gln Tyr
5745              5750                  5755                  5760
Arg Asp Phe Ala Ala Trp Gln Lys Thr Glu Glu Gln Val Ala Glu His
                5765              5770                  5775
Gln Arg Gln Leu Asp Tyr Trp Thr Glu His Leu Ala Asp Ser Thr Pro
            5780              5785                  5790
Ala Glu Leu Leu Thr Asp Leu Pro Arg Pro Ser Ile Leu Ser Gly Arg
    5795              5800                  5805
Ala Asn Glu Leu Pro Leu Thr Ile Glu Gly Arg Leu His Asp Lys Leu
    5810              5815                  5820
Arg Ala Phe Cys Arg Val His Gln Ala Thr Pro Phe Val Ile Leu Leu
5825              5830                  5835                  5840
Ala Ala Leu Arg Ala Ala His Tyr Arg Leu Thr Gly Ala Glu Asp Ala
                5845              5850                  5855
Thr Leu Gly Thr Pro Ile Ala Asn Arg Asn Arg Pro Glu Leu Glu Asn
            5860              5865                  5870
Met Ile Gly Phe Phe Val Asn Thr Gln Cys Met Arg Ile Ala Ile Glu
            5875              5880                  5885
Glu Asn Asp Asn Phe Glu Ser Leu Val Arg Arg Val Arg Ser Thr Ala
    5890              5895                  5900
Thr Ser Ala Phe Ala Asn Gln Asp Val Pro Phe Glu Ser Ile Val Ser
5905              5910                  5915                  5920
Ser Leu Leu Pro Gly Ser Arg Asp Ala Ser Arg Asn Pro Leu Val Gln
                5925              5930                  5935
Val Ile Leu Ala Val His Ser Gln Gln Asp Leu Gly Lys Leu Thr Leu
            5940              5945                  5950
Glu Gly Leu Arg Asp Glu Ala Val Asp Ser Ala Ile Ser Thr Arg Phe
            5955              5960                  5965
Asp Val Glu Phe His Leu Phe Glu His Ala Asp Arg Leu Ser Gly Ser
    5970              5975                  5980
Val Leu Tyr Ala Lys Glu Leu Phe Lys Leu Arg Thr Ile Glu Ser Val
5985              5990                  5995                  6000
Val Ser Val Phe Leu Glu Thr Leu Arg Arg Ala Leu Asp Gln Pro Leu
                6005              6010                  6015
Thr Pro Leu Ala Val Leu Pro Leu Thr Asp Gly Val Gly Glu Ile Ala
            6020              6025                  6030
Ser Lys Gly Leu Leu Asp Val Pro Arg Thr Asp Tyr Pro Arg Asp Ala
            6035              6040                  6045
Asn Ile Val Glu Val Phe Gln Gln His Val Arg Ala Thr Pro Asp Ala
            6050              6055                  6060
Ile Ala Val Lys Asp Ala Thr Ser Ile Leu Thr Tyr Ala Gln Leu Asp
6065              6070                  6075                  6080
Gln Gln Ser Asp Arg Leu Ala Ile Trp Leu Ser Arg Arg His Met Met
                6085              6090                  6095
Pro Glu Thr Leu Val Gly Val Leu Ala Pro Arg Ser Cys Glu Thr Ile
            6100              6105                  6110
Ile Ala Met Phe Gly Ile Met Lys Ala Asn Leu Ala Tyr Leu Pro Leu
            6115              6120                  6125
```

```
Asp  Ile  Asn  Ser  Pro  Ala  Ala  Arg  Leu  Arg  Ser  Ile  Leu  Ser  Ala  Val
         6130                6135                6140

Asp  Gly  Asn  Lys  Leu  Val  Leu  Leu  Gly  Ser  Gly  Val  Thr  Ala  Pro  Glu
6145                6150                6155                          6160

Gln  Glu  Asn  Pro  Glu  Val  Glu  Ala  Val  Gly  Ile  Gln  Glu  Ile  Leu  Ala
              6165                6170                     6175

Gly  Thr  Gly  Leu  Asp  Lys  Thr  Gln  Gly  Ser  Asn  Ala  Arg  Pro  Ser  Ala
         6180                6185                          6190

Thr  Ser  Leu  Ala  Tyr  Val  Ile  Phe  Thr  Ser  Gly  Ser  Thr  Gly  Lys  Pro
              6195                6200                6205

Lys  Gly  Val  Met  Val  Glu  His  Arg  Ser  Val  Thr  Arg  Leu  Ala  Lys  Pro
6210                6215                          6220

Ser  Asn  Val  Ile  Ser  Lys  Leu  Pro  Gln  Gly  Ala  Arg  Val  Ala  His  Leu
6225                6230                6235                          6240

Ala  Asn  Ile  Ala  Phe  Asp  Ala  Ser  Ile  Trp  Glu  Ile  Ala  Thr  Thr  Leu
              6245                6250                     6255

Leu  Asn  Gly  Ala  Thr  Leu  Val  Cys  Leu  Asp  Tyr  His  Thr  Val  Leu  Asp
         6260                6265                     6270

Cys  Arg  Thr  Leu  Lys  Glu  Val  Phe  Glu  Arg  Glu  Ser  Ile  Thr  Val  Val
         6275                6280                     6285

Thr  Leu  Met  Pro  Ala  Leu  Leu  Lys  Gln  Cys  Val  Ala  Glu  Ile  Pro  Glu
         6290                6295                     6300

Thr  Leu  Ala  His  Leu  Asp  Leu  Leu  Tyr  Thr  Gly  Gly  Asp  Arg  Val  Gly
6305                6310                6315                          6320

Gly  His  Asp  Ala  Met  Arg  Ala  Arg  Ser  Leu  Val  Lys  Ile  Gly  Met  Phe
              6325                6330                     6335

Ser  Gly  Tyr  Gly  Pro  Thr  Glu  Asn  Thr  Val  Ile  Ser  Thr  Ile  Tyr  Glu
              6340                6345                     6350

Val  Asp  Ala  Asp  Glu  Met  Phe  Val  Asn  Gly  Val  Pro  Ile  Gly  Lys  Thr
              6355                6360                     6365

Val  Ser  Asn  Ser  Gly  Ala  Tyr  Val  Met  Asp  Arg  Asn  Gln  Gln  Leu  Val
              6370                6375                     6380

Pro  Ser  Gly  Val  Val  Gly  Glu  Leu  Val  Val  Thr  Gly  Asp  Gly  Leu  Ala
6385                6390                6395                          6400

Arg  Gly  Tyr  Thr  Asp  Pro  Ser  Leu  Asn  Lys  Asn  Arg  Phe  Ile  Tyr  Ile
              6405                6410                     6415

Thr  Val  Asn  Gly  Glu  Ser  Ile  Arg  Ala  Tyr  Arg  Thr  Gly  Asp  Arg  Val
              6420                6425                     6430

Arg  Tyr  Arg  Pro  His  Asp  Leu  Gln  Ile  Glu  Phe  Phe  Gly  Arg  Met  Asp
              6435                6440                     6445

Gln  Gln  Val  Lys  Ile  Arg  Gly  His  Arg  Ile  Glu  Pro  Gly  Glu  Val  Glu
         6450                6455                     6460

Ser  Ala  Leu  Leu  Ser  His  Asn  Ser  Val  Gln  Asp  Ala  Ala  Val  Val  Ile
6465                6470                6475                          6480

Cys  Ala  Pro  Ala  Asp  Gln  Asp  Ser  Gly  Ala  Glu  Met  Val  Ala  Phe  Val
                   6485                6490                          6495

Ala  Ala  Arg  Asn  Thr  Glu  Asp  Glu  Asp  Thr  Gln  Glu  Glu  Glu  Ala  Val
                   6500                6505                          6510

Asp  Gln  Val  Gln  Gly  Trp  Glu  Thr  His  Phe  Glu  Thr  Ala  Ala  Tyr  Ser
              6515                6520                     6525

Glu  Val  Lys  Asp  Ile  Arg  Gln  Ser  Glu  Val  Gly  Asn  Asp  Phe  Met  Gly
         6530                6535                     6540

Trp  Thr  Ser  Met  Tyr  Asp  Gly  Ser  Glu  Ile  Asp  Lys  Thr  Asp  Met  His
```

-continued

```
6545                  6550                  6555                  6560
Glu  Trp  Leu  Asn  Asp  Thr  Met  Arg  Met  Ile  Leu  Asp  Ala  Arg  Glu  Pro
               6565                 6570                          6575
Gly  His  Val  Leu  Glu  Ile  Gly  Thr  Gly  Thr  Gly  Met  Val  Met  Phe  Asn
               6580                          6585                 6590
Leu  Ala  Lys  Cys  Pro  Gly  Leu  Gln  Gly  Tyr  Val  Gly  Phe  Glu  Pro  Ser
               6595                          6600                 6605
Lys  Ser  Ala  Ala  Gln  Phe  Val  Asn  Asp  Ala  Ala  Gln  Ser  Phe  Pro  Ala
     6610                          6615                          6620
Leu  Lys  Asp  Gly  Arg  Ser  Ile  Val  His  Val  Gly  Thr  Ala  Thr  Asp  Ile
6625                      6630                          6635                 6640
Asn  Lys  Ala  Gly  Pro  Ile  Gln  Pro  Arg  Leu  Val  Val  Ile  Asn  Ser  Val
                    6645                          6650                 6655
Ala  Gln  Tyr  Phe  Pro  Thr  Pro  Glu  Tyr  Leu  Phe  Arg  Val  Val  Glu  Ala
               6660                          6665                 6670
Leu  Val  Gln  Ile  Pro  Ser  Val  Glu  Arg  Ile  Val  Phe  Gly  Asp  Met  Arg
               6675                          6680                 6685
Thr  Asn  Ala  Ile  Asn  Arg  Asp  Phe  Val  Ala  Ser  Arg  Ala  Leu  His  Thr
               6690                          6695                 6700
Leu  Gly  Glu  Lys  Ala  Asn  Lys  Arg  Leu  Val  Arg  Gln  Met  Ile  Tyr  Glu
6705                      6710                          6715                 6720
Leu  Glu  Ala  Asn  Glu  Glu  Glu  Leu  Leu  Thr  Asp  Pro  Ala  Phe  Phe  Thr
                    6725                          6730                 6735
Ser  Leu  Arg  Thr  Arg  Leu  Gly  Glu  Lys  Ile  Lys  His  Val  Glu  Ile  Leu
               6740                          6745                 6750
Pro  Lys  Thr  Met  Lys  Ala  Thr  Asn  Glu  Leu  Ser  Lys  Tyr  Arg  Tyr  Ala
               6755                          6760                 6765
Ala  Val  Leu  His  Val  Arg  Gly  Ser  Arg  Glu  Gln  Ser  Thr  Ile  His  Gln
6770                      6775                          6780
Val  Ser  Pro  Asn  Ala  Trp  Ile  Asp  Phe  Ala  Ala  Asp  Gly  Leu  Asp  Arg
6785                      6790                          6795                 6800
Gln  Thr  Leu  Ile  Asn  Leu  Leu  Lys  Glu  His  Lys  Asp  Ala  Gly  Thr  Val
                    6805                          6810                 6815
Ala  Ile  Gly  Asn  Ile  Pro  Tyr  Ser  Lys  Thr  Ile  Val  Glu  Arg  Phe  Val
               6820                          6825                 6830
Asn  Lys  Ser  Leu  Ser  Glu  Asp  Met  Glu  Glu  Gly  Gln  Asn  Ser  Leu
               6835                          6840                 6845
Asp  Gly  Ser  Ala  Trp  Val  Ala  Val  Arg  Met  Ala  Gln  Ser  Cys
               6850                          6855                 6860
Pro  Ser  Leu  Asp  Ala  Met  Asp  Val  Lys  Glu  Ile  Ala  Gln  Glu  Ala  Gly
6865                      6870                          6875                 6880
Tyr  Gln  Val  Glu  Val  Ser  Trp  Ala  Arg  Gln  Trp  Ser  Gln  Asn  Gly  Ala
                    6885                          6890                 6895
Leu  Asp  Ala  Ile  Phe  His  His  Phe  Glu  Pro  Pro  Lys  Glu  Gly  Ala  Arg
                    6900                          6905                 6910
Thr  Leu  Ile  Glu  Phe  Pro  Thr  Asp  Tyr  Glu  Gly  Arg  Asn  Val  Asn  Thr
               6915                          6920                 6925
Leu  Thr  Asn  Arg  Pro  Leu  Asn  Ser  Ile  Gln  Ser  Arg  Arg  Leu  Gly  Thr
               6930                          6935                 6940
Gln  Ile  Arg  Glu  Lys  Leu  Gln  Thr  Leu  Leu  Pro  Pro  Tyr  Met  Ile  Pro
6945                      6950                          6955                 6960
Ser  Arg  Ile  Met  Val  Leu  Asp  Gln  Met  Pro  Val  Asn  Asn  Asn  Gly  Lys
                    6965                          6970                 6975
```

```
Ile Asp Arg Lys Glu Leu Val Arg Arg Ala Ile Val Ala Pro Lys Pro
            6980                6985                6990

Arg Ser Ala Ala Thr Arg Val Ala Pro Arg Asn Glu Ile Glu Ala Ile
        6995                7000                7005

Leu Arg Asp Glu Phe Glu Asp Val Leu Gly Thr Val Ser Val Leu
    7010                7015                7020

Asp Asn Phe Phe Asp Leu Gly Gly His Ser Leu Met Ala Thr Lys Leu
7025            7030                7035                    7040

Ala Ala Arg Val Ser Arg Arg Leu Asp Ala His Ile Ser Ile Lys Asp
                7045                7050                7055

Val Phe Asp Gln Pro Val Leu Ala Asp Leu Ala Ala Ser Ile Gln Arg
            7060                7065                7070

Glu Ser Ala Pro His Glu Pro Ile Pro Gln Arg Pro Tyr Thr Gly Pro
        7075                7080                7085

Ala Glu Gln Ser Phe Ala Gln Gly Arg Leu Trp Phe Leu Asp Gln Leu
    7090                7095                7100

Asn Leu Gly Ala Thr Trp Tyr Leu Met Pro Leu Ala Ile Arg Ile Arg
7105            7110                7115                    7120

Gly Gln Leu Arg Val Ala Ala Leu Ser Ala Leu Phe Ala Leu Glu
                7125                7130                7135

Arg Arg His Glu Thr Leu Arg Thr Thr Phe Glu Glu Ser Asp Gly Val
            7140                7145                7150

Gly Val Gln Ile Val Gly Glu Ala Arg Asn Ser Asp Leu Arg Val His
        7155                7160                7165

Asp Val Ser Thr Gly Asp Asp Gly Glu Tyr Leu Glu Val Leu Arg Arg
    7170                7175                7180

Glu Gln Thr Val Pro Phe Asp Leu Ser Ser Glu Pro Gly Trp Arg Val
7185            7190                7195                    7200

Cys Leu Val Lys Thr Gly Glu Glu Asp His Val Leu Ser Ile Val Met
                7205                7210                7215

His His Ile Ile Tyr Asp Gly Trp Ser Val Asp Ile Leu Arg Gly Glu
            7220                7225                7230

Leu Gly Gln Phe Tyr Ser Ala Ala Leu Arg Gly Gln Asp Pro Leu Leu
        7235                7240                7245

His Ala Asn Pro Leu Pro Ile Gln Tyr Arg Asp Phe Ala Ala Trp Gln
    7250                7255                7260

Arg Glu Ala Lys Gln Val Glu Glu His Gln Arg Gln Leu Gly Tyr Trp
7265            7270                7275                    7280

Ser Lys Gln Leu Val Asp Ser Thr Pro Ala Glu Leu Leu Thr Asp Leu
            7285                7290                7295

Pro Arg Pro Ser Ile Leu Ser Gly Arg Ala Gly Ser Val Asp Val Thr
        7300                7305                7310

Ile Glu Gly Ser Val Tyr Gly Ala Leu Gln Ser Phe Cys Arg Thr Arg
    7315                7320                7325

Ser Val Thr Thr Phe Val Val Leu Leu Thr Val Phe Arg Ile Ala His
7330            7335                7340

Phe Arg Leu Thr Ala Val Asp Asp Ala Thr Ile Gly Thr Pro Ile Ala
7345            7350                7355                    7360

Asn Arg Asn Arg Pro Glu Leu Glu Thr Leu Val Gly Cys Phe Val Asn
                7365                7370                7375

Thr Gln Cys Met Arg Ile Ser Ile Ala Asp Asp Asp Asn Phe Glu Gly
            7380                7385                7390

Leu Val Arg Gln Val Arg Asn Val Ala Thr Ala Ala Tyr Ala Asn Gln
        7395                7400                7405
```

```
Asp Val Pro Phe Glu Arg Ile Val Ser Ala Leu Val Pro Gly Ser Arg
    7410                7415                7420
Asn Thr Ser Arg Asn Pro Leu Val Gln Leu Met Phe Ala Val Gln Ser
7425            7430                7435                    7440
Val Glu Asp Tyr Asp Gln Val Arg Leu Glu Gly Leu Glu Ser Val Met
                7445                7450                7455
Met Pro Gly Glu Ala Ser Thr Arg Phe Asp Met Glu Phe His Leu Val
            7460                7465                7470
Pro Gly Asp Gln Lys Leu Thr Gly Ser Val Leu Tyr Ser Ser Asp Leu
            7475                7480                7485
Phe Glu Gln Gly Thr Ile Gln Asn Phe Val Asp Ile Phe Gln Glu Cys
    7490                7495                7500
Leu Arg Ser Val Leu Asp Gln Pro Leu Thr Pro Ile Ser Val Leu Pro
7505            7510                7515                    7520
Phe Ser Asn Ala Ile Ser Asn Leu Glu Ser Leu Asp Leu Leu Glu Met
                7525                7530                7535
Pro Thr Ser Asp Tyr Pro Arg Asp Arg Thr Val Val Asp Leu Phe Arg
            7540                7545                7550
Glu Gln Ala Ala Ile Cys Pro Asp Ser Ile Ala Val Lys Asp Ser Ser
            7555                7560                7565
Ser Gln Leu Thr Tyr Ala Gln Leu Asp Glu Gln Ser Asp Arg Val Ala
    7570                7575                7580
Ala Trp Leu His Glu Arg His Met Pro Ala Glu Ser Leu Val Gly Val
7585            7590                7595                    7600
Leu Ser Pro Arg Ser Cys Glu Thr Ile Ile Ala Tyr Phe Gly Ile Met
                7605                7610                7615
Lys Ala Asn Leu Ala Tyr Leu Pro Leu Asp Val Tyr Ala Pro Asp Ala
            7620                7625                7630
Arg Leu Ala Ala Ile Leu Asp Thr Val Glu Gly Glu Arg Leu Leu Leu
            7635                7640                7645
Leu Gly Ala Gly Val Pro Gln Pro Gly Ile Gln Ile Pro Arg Leu Ser
            7650                7655                7660
Thr Ala Tyr Ile Ala Glu Ala Leu Ser His Ala Thr Thr Val Asp Val
7665            7670                7675                    7680
Thr Ser Ile Pro Gln Pro Ser Ala Thr Ser Leu Ala Tyr Val Ile Phe
                7685                7690                7695
Thr Ser Gly Ser Thr Gly Lys Pro Lys Gly Val Met Ile Glu His Arg
            7700                7705                7710
Gly Ile Val Arg Leu Val Arg Asp Thr Asn Val Asn Val Phe Pro Glu
            7715                7720                7725
Ser Gly Ser Ala Leu Pro Val Ser His Phe Ser Asn Leu Ala Trp Asp
7730            7735                7740
Ala Ala Thr Trp Glu Ile Tyr Thr Ala Val Leu Asn Gly Gly Thr Val
7745            7750                7755                    7760
Val Cys Ile Asp Arg Asp Thr Met Leu Asp Ile Ala Ala Leu Asn Ser
                7765                7770                7775
Thr Phe Arg Lys Glu Asn Val Arg Ala Ala Phe Phe Thr Pro Ala Phe
            7780                7785                7790
Leu Lys Gln Cys Leu Ala Glu Thr Pro Glu Leu Val Ala Asn Leu Glu
            7795                7800                7805
Ile Leu His Thr Ala Gly Asp Arg Leu Asp Pro Gly Asp Ala Asn Leu
            7810                7815                7820
Ala Gly Lys Thr Ala Lys Gly Gly Ile Phe Asn Val Leu Gly His Thr
```

```
             7825                    7830                    7835                    7840
   Glu  Asn  Thr  Ala  Tyr  Ser  Thr  Phe  Tyr  Pro  Val  Val  Gly  Glu  Glu  Thr
                            7845                    7850                    7855
   Phe  Val  Asn  Gly  Val  Pro  Val  Gly  Arg  Gly  Ile  Ser  Asn  Ser  His  Ala
                            7860                    7865                    7870
   Tyr  Ile  Ile  Asp  Arg  His  Gln  Lys  Leu  Val  Pro  Ala  Gly  Val  Met  Gly
                            7875                    7880                    7885
   Glu  Leu  Ile  Leu  Thr  Gly  Asp  Gly  Val  Ala  Arg  Gly  Tyr  Thr  Asp  Ser
        7890                    7895                    7900
   Ala  Leu  Asn  Lys  Asp  Arg  Phe  Val  Tyr  Ile  Asp  Ile  Asn  Gly  Lys  Ser
   7905                    7910                    7915                    7920
   Thr  Trp  Ser  Tyr  Arg  Thr  Gly  Asp  Lys  Ala  Arg  Tyr  Arg  Pro  Arg  Asp
                            7925                    7930                    7935
   Gly  Gln  Leu  Glu  Phe  Phe  Gly  Arg  Met  Asp  Gln  Met  Val  Lys  Ile  Arg
                       7940                    7945                    7950
   Gly  Val  Arg  Ile  Glu  Pro  Gly  Glu  Val  Glu  Leu  Thr  Leu  Leu  Asp  His
             7955                    7960                    7965
   Lys  Ser  Val  Leu  Ala  Ala  Thr  Val  Val  Val  Arg  Arg  Pro  Pro  Asn  Gly
                       7970                    7975                    7980
   Asp  Pro  Glu  Met  Ile  Ala  Phe  Ile  Thr  Ile  Asp  Ala  Glu  Asp  Asp  Val
   7985                    7990                    7995                    8000
   Gln  Thr  His  Lys  Ala  Ile  Tyr  Lys  His  Leu  Gln  Gly  Ile  Leu  Pro  Ala
                       8005                    8010                    8015
   Tyr  Met  Ile  Pro  Ser  His  Leu  Val  Ile  Leu  Asp  Gln  Met  Pro  Val  Thr
                       8020                    8025                    8030
   Asp  Asn  Gly  Lys  Val  Asp  Arg  Lys  Asp  Leu  Ala  Leu  Arg  Ala  Gln  Thr
                       8035                    8040                    8045
   Val  Gln  Lys  Arg  Arg  Ser  Thr  Ala  Ala  Arg  Val  Pro  Pro  Arg  Asp  Glu
             8050                    8055                    8060
   Val  Glu  Ala  Val  Leu  Cys  Glu  Glu  Tyr  Ser  Asn  Leu  Leu  Glu  Val  Glu
   8065                    8070                    8075                    8080
   Val  Gly  Ile  Thr  Asp  Gly  Phe  Phe  Asp  Leu  Gly  Gly  His  Ser  Leu  Leu
                       8085                    8090                    8095
   Ala  Thr  Lys  Leu  Ala  Ala  Arg  Leu  Ser  Arg  Gln  Leu  Asn  Thr  Arg  Val
                       8100                    8105                    8110
   Ser  Val  Lys  Asp  Val  Phe  Asp  Gln  Pro  Ile  Leu  Ala  Asp  Leu  Ala  Asp
             8115                    8120                    8125
   Ile  Ile  Arg  Arg  Gly  Ser  His  Arg  His  Asp  Pro  Ile  Pro  Ala  Thr  Pro
             8130                    8135                    8140
   Tyr  Thr  Gly  Pro  Val  Glu  Gln  Ser  Phe  Ala  Gln  Gly  Arg  Leu  Trp  Phe
   8145                    8150                    8155                    8160
   Leu  Glu  Gln  Leu  Asn  Leu  Gly  Ala  Ser  Trp  Tyr  Leu  Met  Pro  Phe  Ala
                       8165                    8170                    8175
   Ile  Arg  Met  Arg  Gly  Pro  Leu  Gln  Thr  Lys  Ala  Leu  Ala  Val  Ala  Leu
                  8180                    8185                    8190
   Asn  Ala  Leu  Val  His  Arg  His  Glu  Ala  Leu  Arg  Thr  Thr  Phe  Glu  Asp
                  8195                    8200                    8205
   His  Asp  Gly  Val  Gly  Val  Gln  Val  Ile  Gln  Pro  Lys  Ser  Ser  Gln  Asp
             8210                    8215                    8220
   Leu  Arg  Ile  Ile  Asp  Leu  Ser  Asp  Ala  Val  Asp  Asp  Thr  Ala  Tyr  Leu
   8225                    8230                    8235                    8240
   Ala  Ala  Leu  Lys  Arg  Glu  Gln  Thr  Thr  Ala  Phe  Asp  Leu  Thr  Ser  Glu
                       8245                    8250                    8255
```

Pro Gly Trp Arg Val Ser Leu Leu Arg Leu Gly Asp Asp Tyr Ile
            8260                8265                8270

Leu Ser Ile Val Met His His Ile Ile Ser Asp Gly Trp Thr Val Asp
            8275                8280                8285

Val Leu Arg Gln Glu Leu Gly Gln Phe Tyr Ser Ala Ala Ile Arg Gly
            8290                8295                8300

Gln Glu Pro Leu Ser Gln Ala Lys Ser Leu Pro Ile Gln Tyr Arg Asp
8305                8310                8315                8320

Phe Ala Val Trp Gln Arg Gln Glu Asn Gln Ile Lys Glu Gln Ala Lys
                    8325                8330                8335

Gln Leu Lys Tyr Trp Ser Gln Gln Leu Ala Asp Ser Thr Pro Cys Glu
                    8340                8345                8350

Phe Leu Thr Asp Leu Pro Arg Pro Ser Ile Leu Ser Gly Glu Ala Asp
                    8355                8360                8365

Ala Val Pro Met Val Ile Asp Gly Thr Val Tyr Gln Leu Leu Thr Asp
                    8370                8375                8380

Phe Cys Arg Thr His Gln Val Thr Ser Phe Ser Val Leu Leu Ala Ala
8385                8390                8395                8400

Phe Arg Thr Ala His Tyr Arg Leu Thr Gly Thr Leu Asp Ala Thr Val
                    8405                8410                8415

Gly Thr Pro Ile Ala Asn Arg Asn Arg Pro Glu Leu Glu Gly Leu Ile
                    8420                8425                8430

Gly Phe Phe Val Asn Thr Gln Cys Met Arg Met Ala Ile Ser Glu Thr
                    8435                8440                8445

Glu Thr Phe Glu Ser Leu Val Gln Gln Val Arg Leu Thr Thr Thr Glu
                    8450                8455                8460

Ala Phe Ala Asn Gln Asp Val Pro Phe Glu Gln Ile Val Ser Thr Leu
8465                8470                8475                8480

Leu Pro Gly Ser Arg Asp Thr Ser Arg Asn Pro Leu Val Gln Val Met
                    8485                8490                8495

Phe Ala Leu Gln Ser Gln Gln Asp Leu Gly Arg Ile Gln Leu Glu Gly
                    8500                8505                8510

Met Thr Asp Glu Ala Leu Glu Thr Pro Leu Ser Thr Arg Leu Asp Leu
                    8515                8520                8525

Glu Val His Leu Phe Gln Glu Val Gly Lys Leu Ser Gly Ser Leu Leu
                    8530                8535                8540

Tyr Ser Thr Asp Leu Phe Glu Val Glu Thr Ile Arg Gly Ile Val Asp
8545                8550                8555                8560

Val Phe Leu Glu Ile Leu Arg Arg Gly Leu Glu Gln Pro Lys Gln Arg
                    8565                8570                8575

Leu Met Ala Met Pro Ile Thr Asp Gly Ile Thr Lys Leu Arg Asp Gln
                    8580                8585                8590

Gly Leu Leu Thr Val Ala Lys Pro Ala Tyr Pro Arg Glu Ser Ser Val
                    8595                8600                8605

Ile Asp Leu Phe Arg Gln Gln Val Ala Ala Ala Pro Asp Ala Ile Ala
                    8610                8615                8620

Val Trp Asp Ser Ser Ser Thr Leu Thr Tyr Ala Asp Leu Asp Gly Gln
8625                8630                8635                8640

Ser Asn Lys Leu Ala His Trp Leu Cys Gln Arg Asn Met Ala Pro Glu
                    8645                8650                8655

Thr Leu Val Ala Val Phe Ala Pro Arg Ser Cys Leu Thr Ile Val Ala
                    8660                8665                8670

Phe Leu Gly Val Leu Lys Ala Asn Leu Ala Tyr Leu Pro Leu Asp Val
                    8675                8680                8685

```
Asn Ala Pro Ala Ala Arg Ile Glu Ala Ile Leu Ser Ala Val Pro Gly
    8690                8695                8700
His Lys Leu Val Leu Val Gln Ala His Gly Pro Glu Leu Gly Leu Thr
8705                8710                8715                8720
Met Ala Asp Thr Glu Leu Val Gln Ile Asp Glu Ala Leu Ala Ser Ser
                8725                8730                8735
Ser Ser Gly Asp His Glu Gln Ile Ala Ser Gly Pro Thr Ala Thr
            8740                8745                8750
Ser Leu Ala Tyr Val Met Phe Thr Ser Gly Ser Thr Gly Lys Pro Lys
            8755                8760                8765
Gly Val Met Ile Asp His Arg Ser Ile Ile Arg Leu Val Lys Asn Ser
            8770                8775                8780
Asp Val Val Ala Thr Leu Pro Thr Pro Val Arg Met Ala Asn Val Ser
8785                8790                8795                8800
Asn Leu Ala Phe Asp Ile Ser Val Gln Glu Ile Tyr Thr Ala Leu Leu
                8805                8810                8815
Asn Gly Gly Thr Leu Val Cys Leu Asp Tyr Leu Thr Leu Leu Asp Ser
                8820                8825                8830
Lys Ile Leu Tyr Asn Val Phe Val Glu Ala Gln Val Asn Ala Ala Met
            8835                8840                8845
Phe Thr Pro Val Leu Leu Lys Gln Cys Leu Gly Asn Met Pro Ala Ile
    8850                8855                8860
Ile Ser Arg Leu Ser Val Leu Phe Asn Val Gly Asp Arg Leu Asp Ala
8865                8870                8875                8880
His Asp Ala Val Ala Ala Ser Gly Leu Ile Gln Asp Ala Val Tyr Asn
                8885                8890                8895
Ala Tyr Gly Pro Thr Glu Asn Gly Met Gln Ser Thr Met Tyr Lys Val
            8900                8905                8910
Asp Val Asn Glu Pro Phe Val Asn Gly Val Pro Ile Gly Arg Ser Ile
            8915                8920                8925
Thr Asn Ser Gly Ala Tyr Val Met Asp Gly Asn Gln Gln Leu Val Ser
    8930                8935                8940
Pro Gly Val Met Gly Glu Ile Val Val Thr Gly Asp Gly Leu Ala Arg
8945                8950                8955                8960
Gly Tyr Thr Asp Ser Ala Leu Asp Glu Asp Arg Phe Val His Val Thr
                8965                8970                8975
Ile Asp Gly Glu Glu Asn Ile Lys Ala Tyr Arg Thr Gly Asp Arg Val
            8980                8985                8990
Arg Tyr Arg Pro Lys Asp Phe Glu Ile Glu Phe Phe Gly Arg Met Asp
            8995                9000                9005
Gln Gln Val Lys Ile Arg Gly His Arg Ile Glu Pro Ala Glu Val Glu
    9010                9015                9020
His Ala Leu Leu Gly His Asp Leu Val His Asp Ala Ala Val Val Leu
9025                9030                9035                9040
Arg Lys Pro Ala Asn Gln Glu Pro Glu Met Ile Ala Phe Ile Thr Ser
                9045                9050                9055
Gln Glu Asp Glu Thr Ile Glu Gln His Glu Ser Asn Lys Gln Val Gln
            9060                9065                9070
Gly Trp Gly Glu His Phe Asp Val Ser Arg Tyr Ala Asp Ile Lys Asp
            9075                9080                9085
Leu Asp Thr Ser Thr Phe Gly His Asp Phe Leu Gly Trp Thr Ser Met
    9090                9095                9100
Tyr Asp Gly Val Asp Ile Pro Val Asn Glu Met Lys Glu Trp Leu Asp
```

```
                9105                    9110                    9115                    9120

Glu  Thr  Thr  Ala  Ser  Leu  Leu  Asp  Asn  Arg  Pro  Pro  Gly  His  Ile  Leu
                           9125                    9130                    9135

Glu  Ile  Gly  Ala  Gly  Thr  Gly  Met  Ile  Leu  Ser  Asn  Leu  Gly  Lys  Val
                      9140                    9145                    9150

Asp  Gly  Leu  Gln  Lys  Tyr  Val  Gly  Leu  Asp  Pro  Ala  Pro  Ser  Ala  Ala
                      9155                    9160                    9165

Ile  Phe  Val  Asn  Glu  Ala  Val  Lys  Ser  Leu  Pro  Ser  Leu  Ala  Gly  Lys
                 9170                    9175                    9180

Ala  Arg  Val  Leu  Val  Gly  Thr  Ala  Leu  Asp  Ile  Gly  Ser  Leu  Asp  Lys
        9185                    9190                    9195                    9200

Asn  Glu  Ile  Gln  Pro  Glu  Leu  Val  Val  Ile  Asn  Ser  Val  Ala  Gln  Tyr
                           9205                    9210                    9215

Phe  Pro  Thr  Ser  Glu  Tyr  Leu  Ile  Lys  Val  Val  Lys  Ala  Val  Val  Glu
                           9220                    9225                    9230

Val  Pro  Ser  Val  Lys  Arg  Val  Phe  Phe  Gly  Asp  Ile  Arg  Ser  Gln  Ala
                           9235                    9240                    9245

Leu  Asn  Arg  Asp  Phe  Leu  Ala  Ala  Arg  Ala  Val  Arg  Ala  Leu  Gly  Asp
                      9250                    9255                    9260

Asn  Ala  Ser  Lys  Glu  Gln  Ile  Arg  Glu  Lys  Ile  Ala  Glu  Leu  Glu  Glu
        9265                    9270                    9275                    9280

Ser  Glu  Glu  Glu  Leu  Leu  Val  Asp  Pro  Ala  Phe  Phe  Val  Ser  Leu  Arg
                           9285                    9290                    9295

Ser  Gln  Leu  Pro  Asn  Ile  Lys  His  Val  Glu  Val  Leu  Pro  Lys  Leu  Met
                      9300                    9305                    9310

Lys  Ala  Thr  Asn  Glu  Leu  Ser  Ser  Tyr  Arg  Tyr  Ala  Ala  Val  Leu  His
                      9315                    9320                    9325

Ile  Ser  His  Asn  Glu  Glu  Glu  Gln  Leu  Leu  Ile  Gln  Asp  Ile  Asp  Pro
                      9330                    9335                    9340

Thr  Ala  Trp  Val  Asp  Phe  Ala  Ala  Thr  Gln  Lys  Asp  Ser  Gln  Gly  Leu
        9345                    9350                    9355                    9360

Arg  Asn  Leu  Leu  Gln  Gln  Gly  Arg  Asp  Asp  Val  Met  Ile  Ala  Val  Gly
                           9365                    9370                    9375

Asn  Ile  Pro  Tyr  Ser  Lys  Thr  Ile  Val  Glu  Arg  His  Ile  Met  Asn  Ser
                           9380                    9385                    9390

Leu  Asp  Gln  Asp  His  Val  Asn  Ser  Leu  Asp  Gly  Thr  Ser  Trp  Ile  Ser
                      9395                    9400                    9405

Asp  Ala  Arg  Ser  Ala  Ala  Ala  Ile  Cys  Thr  Ser  Phe  Asp  Ala  Pro  Ala
                      9410                    9415                    9420

Leu  Thr  Gln  Leu  Ala  Lys  Glu  Glu  Gly  Phe  Arg  Val  Glu  Leu  Ser  Trp
        9425                    9430                    9435                    9440

Ala  Arg  Gln  Arg  Ser  Gln  Asn  Gly  Ala  Leu  Asp  Ala  Val  Phe  His  Arg
                           9445                    9450                    9455

Leu  Ala  Thr  Asp  Ala  Asn  Cys  Glu  Arg  Ser  Arg  Val  Leu  Val  His  Phe
                      9460                    9465                    9470

Pro  Thr  Asp  His  Gln  Gly  Arg  Gln  Leu  Arg  Thr  Leu  Thr  Asn  Arg  Pro
                      9475                    9480                    9485

Leu  Gln  Arg  Ala  Gln  Ser  Arg  Arg  Ile  Glu  Ser  Gln  Val  Phe  Glu  Ala
                      9490                    9495                    9500

Leu  Gln  Thr  Ala  Leu  Pro  Ala  Tyr  Met  Ile  Pro  Ser  Arg  Ile  Ile  Val
                      9505                    9510                    9515                    9520

Leu  Pro  Gln  Met  Pro  Thr  Asn  Ala  Asn  Gly  Lys  Val  Asp  Arg  Lys  Gln
                      9525                    9530                    9535
```

```
Leu Ala Arg Arg Ala Gln Val Val Ala Lys Arg Lys Ala Val Ser Ala
                9540                9545                9550

Arg Val Ala Pro Arg Asn Asp Thr Glu Ile Val Leu Cys Glu Glu Tyr
                9555                9560                9565

Ala Asp Ile Leu Gly Thr Glu Val Gly Ile Thr Asp Asn Phe Phe Asp
                9570                9575                9580

Met Gly Gly His Ser Leu Met Ala Thr Lys Leu Ala Ala Arg Leu Ser
9585                9590                9595                9600

Arg Arg Leu Asp Thr Arg Val Thr Val Lys Glu Val Phe Asp Lys Pro
                9605                9610                9615

Val Leu Ala Asp Leu Ala Ala Ser Ile Glu Gln Gly Ser Thr Pro His
                9620                9625                9630

Leu Pro Ile Ala Ser Ser Val Tyr Ser Gly Pro Val Glu Gln Ser Tyr
                9635                9640                9645

Ala Gln Gly Arg Leu Trp Phe Leu Asp Gln Phe Asn Leu Asn Ala Thr
                9650                9655                9660

Trp Tyr His Met Ser Leu Ala Met Arg Leu Leu Gly Pro Leu Asn Met
9665                9670                9675                9680

Asp Ala Leu Asp Val Ala Leu Arg Ala Leu Glu Gln Arg His Glu Thr
                9685                9690                9695

Leu Arg Thr Thr Phe Glu Ala Gln Lys Asp Ile Gly Val Gln Val Val
                9700                9705                9710

His Glu Ala Gly Met Lys Arg Leu Lys Val Leu Asp Leu Ser Asp Lys
                9715                9720                9725

Asn Glu Lys Glu His Met Ala Val Leu Glu Asn Glu Gln Met Arg Pro
                9730                9735                9740

Phe Thr Leu Ala Ser Glu Pro Gly Trp Lys Gly His Leu Ala Arg Leu
9745                9750                9755                9760

Gly Pro Thr Glu Tyr Ile Leu Ser Leu Val Met His His Met Phe Ser
                9765                9770                9775

Asp Gly Trp Ser Val Asp Ile Leu Arg Gln Glu Leu Gly Gln Phe Tyr
                9780                9785                9790

Ser Ala Ala Leu Arg Gly Arg Asp Pro Leu Ser Gln Val Lys Pro Leu
                9795                9800                9805

Pro Ile Gln Tyr Arg Asp Phe Ala Ala Trp Gln Lys Glu Ala Ala Gln
                9810                9815                9820

Val Ala Glu His Glu Arg Gln Leu Ala Tyr Trp Glu Asn Gln Leu Ala
9825                9830                9835                9840

Asp Ser Thr Pro Gly Glu Leu Leu Thr Asp Phe Pro Arg Pro Gln Phe
                9845                9850                9855

Leu Ser Gly Lys Ala Gly Val Ile Pro Val Thr Ile Glu Gly Pro Val
                9860                9865                9870

Tyr Glu Lys Leu Leu Lys Phe Ser Lys Glu Arg Gln Val Thr Leu Phe
                9875                9880                9885

Ser Val Leu Leu Thr Ala Phe Arg Ala Thr His Phe Arg Leu Thr Gly
                9890                9895                9900

Ala Glu Asp Ala Thr Ile Gly Thr Pro Ile Ala Asn Arg Asn Arg Pro
9905                9910                9915                9920

Glu Leu Glu His Ile Ile Gly Phe Phe Val Asn Thr Gln Cys Met Arg
                9925                9930                9935

Leu Leu Leu Asp Thr Gly Ser Thr Phe Glu Ser Leu Val Gln His Val
                9940                9945                9950

Arg Ser Val Ala Thr Asp Ala Tyr Ser Asn Gln Asp Ile Pro Phe Glu
                9955                9960                9965
```

```
Arg  Ile  Val  Ser  Ala  Leu  Leu  Pro  Gly  Ser  Arg  Asp  Ala  Ser  Arg  Ser
     9970                    9975                    9980

Pro  Leu  Ile  Gln  Leu  Met  Phe  Ala  Leu  His  Ser  Gln  Pro  Asp  Leu  Gly
9985                    9990                    9995                         10000

Asn  Ile  Thr  Leu  Glu  Gly  Leu  Glu  His  Glu  Arg  Leu  Pro  Thr  Ser  Val
          10005                    10010                    10015

Ala  Thr  Arg  Phe  Asp  Met  Glu  Phe  His  Leu  Phe  Gln  Glu  Pro  Asn  Lys
          10020                    10025                    10030

Leu  Ser  Gly  Ser  Ile  Leu  Phe  Ala  Asp  Glu  Leu  Phe  Gln  Pro  Glu  Thr
          10035                    10040                    10045

Ile  Asn  Ser  Val  Val  Thr  Val  Phe  Gln  Glu  Ile  Leu  Arg  Arg  Gly  Leu
     10050                    10055                    10060

Asp  Gln  Pro  Gln  Val  Ser  Ile  Ser  Thr  Met  Pro  Leu  Thr  Asp  Gly  Leu
10065                    10070                    10075                    10080

Ile  Asp  Leu  Glu  Lys  Leu  Gly  Leu  Leu  Glu  Ile  Glu  Ser  Ser  Asn  Phe
               10085                    10090                    10095

Pro  Arg  Asp  Tyr  Ser  Val  Val  Asp  Val  Phe  Arg  Gln  Gln  Val  Ala  Ala
               10100                    10105                    10110

Asn  Pro  Asn  Ala  Pro  Ala  Val  Val  Asp  Ser  Glu  Thr  Ser  Met  Ser  Tyr
          10115                    10120                    10125

Thr  Ser  Leu  Asp  Gln  Lys  Ser  Glu  Gln  Ile  Ala  Ala  Trp  Leu  His  Ala
          10130                    10135                    10140

Gln  Gly  Leu  Arg  Pro  Glu  Ser  Leu  Ile  Cys  Val  Met  Ala  Pro  Arg  Ser
10145                    10150                    10155                    10160

Phe  Glu  Thr  Ile  Val  Ser  Leu  Phe  Gly  Ile  Leu  Lys  Ala  Gly  Tyr  Ala
               10165                    10170                    10175

Tyr  Leu  Pro  Leu  Asp  Val  Asn  Ser  Pro  Ala  Ala  Arg  Ile  Gln  Pro  Ile
               10180                    10185                    10190

Leu  Ser  Glu  Val  Glu  Gly  Lys  Arg  Leu  Val  Leu  Leu  Gly  Ser  Gly  Ile
               10195                    10200                    10205

Asp  Met  Pro  Gln  Ser  Asp  Arg  Met  Asp  Val  Glu  Thr  Ala  Arg  Ile  Gln
          10210                    10215                    10220

Asp  Ile  Leu  Thr  Asn  Thr  Lys  Val  Glu  Arg  Ser  Asp  Pro  Met  Ser  Arg
10225                    10230                    10235                    10240

Pro  Ser  Ala  Thr  Ser  Leu  Ala  Tyr  Val  Ile  Phe  Thr  Ser  Gly  Ser  Thr
               10245                    10250                    10255

Gly  Arg  Pro  Lys  Gly  Val  Met  Ile  Glu  His  Arg  Asn  Ile  Leu  Arg  Leu
               10260                    10265                    10270

Val  Lys  Gln  Ser  Asn  Val  Thr  Ser  Gln  Leu  Pro  Gln  Asp  Leu  Arg  Met
          10275                    10280                    10285

Ala  His  Ile  Ser  Asn  Leu  Ala  Phe  Asp  Ala  Ser  Ile  Trp  Glu  Ile  Phe
          10290                    10295                    10300

Thr  Ala  Ile  Leu  Asn  Gly  Gly  Ala  Leu  Ile  Cys  Ile  Asp  Tyr  Phe  Thr
10305                    10310                    10315                    10320

Leu  Leu  Asp  Ser  Gln  Ala  Leu  Arg  Thr  Thr  Phe  Glu  Lys  Ala  Arg  Val
               10325                    10330                    10335

Asn  Ala  Thr  Leu  Phe  Ala  Pro  Ala  Leu  Leu  Lys  Glu  Cys  Leu  Asn  His
               10340                    10345                    10350

Ala  Pro  Thr  Leu  Phe  Glu  Asp  Leu  Lys  Val  Leu  Tyr  Ile  Gly  Gly  Asp
               10355                    10360                    10365

Arg  Leu  Asp  Ala  Thr  Asp  Ala  Ala  Lys  Ile  Gln  Ala  Leu  Val  Lys  Gly
10370                    10375                    10380

Thr  Val  Tyr  Asn  Ala  Tyr  Gly  Pro  Thr  Glu  Asn  Thr  Val  Met  Ser  Thr
```

```
       10385                  10390                 10395                    10400
Ile Tyr Arg Leu Thr Asp Gly Glu Ser Tyr Ala Asn Gly Val Pro Ile
                 10405                 10410                 10415
Gly Asn Ala Val Ser Ser Ser Gly Ala Tyr Ile Met Asp Gln Lys Gln
                 10420                 10425                 10430
Arg Leu Val Pro Pro Gly Val Met Gly Glu Leu Val Val Ser Gly Asp
                 10435                 10440                 10445
Gly Leu Ala Arg Gly Tyr Thr Asn Ser Thr Leu Asn Ala Asp Arg Phe
                 10450                 10455                 10460
Val Asp Ile Val Ile Asn Asp Gln Lys Ala Arg Ala Tyr Arg Thr Gly
10465                  10470                 10475                    10480
Asp Arg Thr Arg Tyr Arg Pro Lys Asp Gly Ser Ile Glu Phe Phe Gly
                 10485                 10490                 10495
Arg Met Asp Gln Gln Val Lys Ile Arg Gly His Arg Val Glu Pro Ala
                 10500                 10505                 10510
Glu Val Glu Gln Ala Met Leu Gly Asn Lys Ala Ile His Asp Ala Ala
                 10515                 10520                 10525
Val Val Val Gln Ala Val Asp Gly Gln Glu Thr Glu Met Ile Gly Phe
                 10530                 10535                 10540
Val Ser Met Ala Ser Asp Arg Phe Ser Glu Gly Glu Glu Ile Thr
10545                  10550                 10555                    10560
Asn Gln Val Gln Glu Trp Glu Asp His Phe Glu Ser Thr Ala Tyr Ala
                 10565                 10570                 10575
Gly Ile Glu Ala Ile Asp Gln Ala Thr Leu Gly Arg Asp Phe Thr Ser
                 10580                 10585                 10590
Trp Thr Ser Met Tyr Asn Gly Asn Leu Ile Asp Lys Ala Glu Met Glu
                 10595                 10600                 10605
Glu Trp Leu Asp Asp Thr Met Gln Ser Leu Leu Asp Lys Glu Asp Ala
                 10610                 10615                 10620
Arg Pro Cys Ala Glu Ile Gly Thr Gly Thr Gly Met Val Leu Phe Asn
10625                  10630                 10635                    10640
Leu Pro Lys Asn Asp Gly Leu Glu Ser Tyr Val Gly Ile Glu Pro Ser
                 10645                 10650                 10655
Arg Ser Ala Ala Leu Phe Val Asp Lys Ala Ala Gln Asp Phe Pro Gly
                 10660                 10665                 10670
Leu Gln Gly Lys Thr Gln Ile Leu Val Gly Thr Ala Glu Asp Ile Lys
                 10675                 10680                 10685
Leu Val Lys Asp Phe His Pro Asp Val Val Val Ile Asn Ser Val Ala
                 10690                 10695                 10700
Gln Tyr Phe Pro Ser Arg Ser Tyr Leu Val Gln Ile Ala Ser Glu Leu
10705                  10710                 10715                    10720
Ile His Met Thr Ser Val Lys Thr Ile Phe Phe Gly Asp Met Arg Ser
                 10725                 10730                 10735
Trp Ala Thr Asn Arg Asp Phe Leu Val Ser Arg Ala Leu Tyr Thr Leu
                 10740                 10745                 10750
Gly Asp Lys Ala Thr Lys Asp Gln Ile Arg Gln Glu Val Ala Arg Leu
                 10755                 10760                 10765
Glu Glu Asn Glu Asp Glu Leu Leu Val Asp Pro Ala Phe Phe Thr Ser
                 10770                 10775                 10780
Leu Thr Ser Gln Trp Pro Gly Lys Val Lys His Val Glu Ile Leu Pro
10785                  10790                 10795                    10800
Lys Arg Met Arg Thr Ser Asn Glu Leu Ser Ser Tyr Arg Tyr Ala Ala
                 10805                 10810                 10815
```

-continued

```
Val Leu His Ile Cys Arg Asp Gly Glu Gly Arg Asn Arg Tyr Gly Arg
            10820               10825                   10830

Arg Val His Ser Val Glu Glu Asn Ala Trp Ile Asp Phe Ala Ser Ser
            10835               10840                   10845

Gly Met Asp Arg His Ala Leu Val Gln Met Leu Asp Glu Arg Arg Asp
            10850               10855                   10860

Ala Lys Thr Val Ala Ile Gly Asn Ile Pro His Ser Asn Thr Ile Asn
10865               10870               10875                   10880

Glu Arg His Phe Thr Thr Ser Leu Asp Thr Glu Gly Glu Gly Ile Ala
            10885               10890                   10895

Gln Asp Ser Leu Asp Gly Ser Ala Trp Gln Ser Ala Thr Lys Ala Met
            10900               10905                   10910

Ala Ala Arg Cys Pro Cys Leu Ser Val Thr Glu Leu Val Glu Ile Gly
            10915               10920                   10925

Gln Ala Ala Gly Phe Arg Val Glu Val Ser Trp Ala Arg Gln Arg Ser
            10930               10935                   10940

Gln His Gly Ala Leu Asp Val Phe His His Leu Glu Asp Asp Arg
10945               10950               10955                   10960

Val Gly Arg Val Leu Ile Asn Phe Pro Thr Asp Phe Glu Arg Leu Pro
            10965               10970                   10975

Pro Ser Thr Gly Leu Thr Ser Arg Pro Leu Gln Arg Ile Gln Asn Arg
            10980               10985                   10990

Arg Phe Glu Ser Gln Ile Arg Glu Gln Leu Gln Thr Leu Leu Pro Pro
            10995               11000                   11005

Tyr Met Val Pro Ser Arg Ile Val Val Leu Glu Arg Met Pro Leu Asn
            11010               11015                   11020

Ala Asn Ser Lys Val Asp Arg Lys Glu Leu Ala Arg Lys Ala Arg Thr
11025               11030               11035                   11040

Leu Gln Thr Ile Lys Pro Ser Ala Thr Arg Val Ala Pro Arg Asn Asp
            11045               11050                   11055

Ile Glu Ala Val Leu Cys Asp Glu Phe Gln Ala Val Leu Gly Val Thr
            11060               11065                   11070

Val Gly Val Met Asp Asn Phe Phe Glu Leu Gly Gly His Ser Leu Met
            11075               11080                   11085

Ala Thr Lys Leu Ala Ala Arg Leu Ser Arg Arg Leu Asp Thr Arg Val
            11090               11095                   11100

Ser Val Lys Asp Ile Phe Asn Gln Pro Ile Leu Gln Asp Leu Ala Asp
11105               11110               11115                   11120

Val Val Gln Thr Gly Ser Ala Pro His Glu Ala Ile Pro Ser Thr Pro
            11125               11130                   11135

Tyr Ser Gly Pro Val Glu Gln Ser Phe Ser Gln Gly Arg Leu Trp Phe
            11140               11145                   11150

Leu Asp Gln Leu Asn Leu Asn Ala Ser Trp Tyr His Met Pro Leu Ala
            11155               11160                   11165

Ser Arg Leu Arg Gly Pro Leu Arg Ile Glu Ala Leu Gln Ser Ala Leu
            11170               11175                   11180

Ala Thr Ile Glu Ala Arg His Glu Ser Leu Arg Thr Thr Phe Glu Glu
11185               11190               11195                   11200

Gln Asp Gly Val Pro Val Gln Ile Val Arg Ala Ala Arg Asn Lys Gln
            11205               11210                   11215

Leu Arg Ile Ile Asp Val Ser Gly Thr Glu Asp Ala Tyr Leu Ala Ala
            11220               11225                   11230

Leu Lys Gln Glu Gln Asp Ala Ala Phe Asp Leu Thr Ala Glu Pro Gly
            11235               11240                   11245
```

Trp Arg Val Ala Leu Leu Arg Leu Gly Pro Asp Asp His Val Leu Ser
    11250                 11255                 11260

Ile Val Met His His Ile Ile Ser Asp Gly Trp Ser Val Asp Ile Leu
11265                 11270                 11275                 11280

Arg Gln Glu Leu Gly Gln Leu Tyr Ser Asn Ala Ser Ser Gln Pro Ala
                11285                 11290                 11295

Pro Leu Pro Ile Gln Tyr Arg Asp Phe Ala Ile Trp Gln Lys Gln Asp
        11300                 11305                 11310

Ser Gln Ile Ala Glu His Gln Lys Gln Leu Asn Tyr Trp Lys Arg Gln
        11315                 11320                 11325

Leu Val Asn Ser Lys Pro Ala Glu Leu Leu Ala Asp Phe Thr Arg Pro
        11330                 11335                 11340

Lys Ala Leu Ser Gly Asp Ala Asp Val Ile Pro Ile Glu Ile Asp Asp
11345                 11350                 11355                 11360

Gln Val Tyr Gln Asn Leu Arg Ser Phe Cys Arg Ala Arg His Val Thr
                11365                 11370                 11375

Ser Phe Val Ala Leu Leu Ala Ala Phe Arg Ala Ala His Tyr Arg Leu
                11380                 11385                 11390

Thr Gly Ala Glu Asp Ala Thr Ile Gly Ser Pro Ile Ala Asn Arg Asn
                11395                 11400                 11405

Arg Pro Glu Leu Glu Gly Leu Ile Gly Cys Phe Val Asn Thr Gln Cys
        11410                 11415                 11420

Leu Arg Ile Pro Val Lys Ser Glu Asp Thr Phe Asp Thr Leu Val Lys
11425                 11430                 11435                 11440

Gln Ala Arg Glu Thr Ala Thr Glu Ala Gln Asp Asn Gln Asp Val Pro
                11445                 11450                 11455

Phe Glu Arg Ile Val Ser Ser Met Val Ala Ser Ser Arg Asp Thr Ser
        11460                 11465                 11470

Arg Asn Pro Leu Val Gln Val Met Phe Ala Val His Ser Gln His Asp
            11475                 11480                 11485

Leu Gly Asn Ile Arg Leu Glu Gly Val Glu Gly Lys Pro Val Ser Met
        11490                 11495                 11500

Ala Ala Ser Thr Arg Phe Asp Ala Glu Met His Leu Phe Glu Asp Gln
11505                 11510                 11515                 11520

Gly Met Leu Gly Gly Asn Val Val Phe Ser Lys Asp Leu Phe Glu Ser
                11525                 11530                 11535

Glu Thr Ile Arg Ser Val Val Ala Val Phe Gln Glu Thr Leu Arg Arg
                11540                 11545                 11550

Gly Leu Ala Asn Pro His Ala Asn Leu Ala Thr Leu Pro Leu Thr Asp
            11555                 11560                 11565

Gly Leu Pro Ser Leu Arg Ser Leu Cys Leu Gln Val Asn Gln Pro Asp
        11570                 11575                 11580

Tyr Pro Arg Asp Ala Ser Val Ile Asp Val Phe Arg Glu Gln Val Ala
11585                 11590                 11595                 11600

Ser Ile Pro Lys Ser Ile Ala Val Ile Asp Ala Ser Ser Gln Leu Thr
                11605                 11610                 11615

Tyr Thr Glu Leu Asp Glu Arg Ser Ser Gln Leu Ala Thr Trp Leu Arg
                11620                 11625                 11630

Arg Gln Val Thr Val Pro Glu Glu Leu Val Gly Val Leu Ala Pro Arg
            11635                 11640                 11645

Ser Cys Glu Thr Ile Ile Ala Phe Leu Gly Ile Ile Lys Ala Asn Leu
    11650                 11655                 11660

Ala Tyr Leu Pro Leu Asp Val Asn Ala Pro Ala Gly Arg Ile Glu Thr

```
                 11665                11670                11675                11680
      Ile Leu Ser Ser Leu Pro Gly Asn Arg Leu Ile Leu Leu Gly Ser Asp
                           11685                11690                11695
      Thr Gln Ala Val Lys Leu His Ala Asn Ser Val Arg Phe Thr Arg Ile
                 11700                11705                11710
      Ser Asp Ala Leu Val Glu Ser Gly Ser Pro Pro Thr Glu Glu Leu Ser
                 11715                11720                11725
      Thr Arg Pro Thr Ala Gln Ser Leu Ala Tyr Val Met Phe Thr Ser Gly
                 11730                11735                11740
      Ser Thr Gly Val Pro Lys Gly Val Met Val Glu His Arg Gly Ile Thr
      11745                11750                11755                11760
      Arg Leu Val Lys Asn Ser Asn Val Val Ala Lys Gln Pro Ala Ala Ala
                           11765                11770                11775
      Ala Ile Ala His Leu Ser Asn Ile Ala Phe Asp Ala Ser Ser Trp Glu
                           11780                11785                11790
      Ile Tyr Ala Pro Leu Leu Asn Gly Gly Thr Val Val Cys Ile Asp Tyr
                 11795                11800                11805
      Tyr Thr Thr Ile Asp Ile Lys Ala Leu Glu Ala Val Phe Lys Gln His
                 11810                11815                11820
      His Ile Arg Gly Ala Met Leu Pro Pro Ala Leu Leu Lys Gln Cys Leu
      11825                11830                11835                11840
      Val Ser Ala Pro Thr Met Ile Ser Ser Leu Glu Ile Leu Phe Ala Ala
                           11845                11850                11855
      Gly Asp Arg Leu Ser Ser Gln Asp Ala Ile Leu Ala Arg Arg Ala Val
                 11860                11865                11870
      Gly Ser Gly Val Tyr Asn Ala Tyr Gly Pro Thr Glu Asn Thr Val Leu
                 11875                11880                11885
      Ser Thr Ile His Asn Ile Gly Glu Asn Glu Ala Phe Ser Asn Gly Val
                 11890                11895                11900
      Pro Ile Gly Asn Ala Val Ser Asn Ser Gly Ala Phe Val Met Asp Gln
      11905                11910                11915                11920
      Asn Gln Gln Leu Val Ser Ala Gly Val Ile Gly Glu Leu Val Val Thr
                           11925                11930                11935
      Gly Asp Gly Leu Ala Arg Gly Tyr Thr Asp Ser Lys Leu Arg Val Asp
                 11940                11945                11950
      Arg Phe Ile Tyr Ile Thr Leu Asp Gly Asn Arg Val Arg Ala Tyr Arg
                 11955                11960                11965
      Thr Gly Asp Arg Val Arg His Arg Pro Lys Asp Gly Gln Ile Glu Phe
                 11970                11975                11980
      Phe Gly Arg Met Asp Gln Gln Ile Lys Ile Arg Gly His Arg Ile Glu
      11985                11990                11995                12000
      Pro Ala Glu Val Glu Gln Ala Leu Ala Arg Asp Pro Ala Ile Ser Asp
                           12005                12010                12015
      Ser Ala Val Ile Thr Gln Leu Thr Asp Glu Glu Pro Glu Leu Val
                           12020                12025                12030
      Ala Phe Phe Ser Leu Lys Gly Asn Ala Asn Gly Thr Asn Gly Val Asn
                           12035                12040                12045
      Gly Val Ser Asp Gln Glu Lys Ile Asp Gly Asp Glu Gln His Ala Leu
                 12050                12055                12060
      Leu Met Glu Asn Lys Ile Arg His Asn Leu Gln Ala Leu Leu Pro Thr
      12065                12070                12075                12080
      Tyr Met Ile Pro Ser Arg Ile Ile His Val Asp Gln Leu Pro Val Asn
                           12085                12090                12095
```

```
Ala  Asn  Gly  Lys  Ile  Asp  Arg  Asn  Glu  Leu  Ala  Val  Arg  Ala  Gln  Ala
               12100                12105                    12110

Thr  Pro  Arg  Thr  Ser  Ser  Val  Ser  Thr  Tyr  Val  Ala  Pro  Arg  Asn  Asp
               12115                12120                    12125

Ile  Glu  Thr  Ile  Ile  Cys  Lys  Glu  Phe  Ala  Asp  Ile  Leu  Ser  Val  Arg
          12130                12135                    12140

Val  Gly  Ile  Thr  Asp  Asn  Phe  Phe  Asp  Leu  Gly  Gly  His  Ser  Leu  Ile
12145               12150                    12155                         12160

Ala  Thr  Lys  Leu  Ala  Ala  Arg  Leu  Ser  Arg  Arg  Leu  Asp  Thr  Arg  Val
               12165                12170                         12175

Ser  Val  Arg  Asp  Val  Phe  Asp  Thr  Pro  Val  Val  Gly  Gln  Leu  Ala  Ala
               12180                12185                    12190

Ser  Ile  Gln  Gln  Gly  Ser  Thr  Pro  His  Glu  Ala  Ile  Pro  Ala  Leu  Ser
          12195                12200                    12205

His  Ser  Gly  Pro  Val  Gln  Gln  Ser  Phe  Ala  Gln  Gly  Arg  Leu  Trp  Phe
          12210                12215                    12220

Leu  Asp  Arg  Phe  Asn  Leu  Asn  Ala  Ala  Trp  Tyr  Ile  Met  Pro  Phe  Gly
12225               12230                    12235                         12240

Val  Arg  Leu  Arg  Gly  Pro  Leu  Arg  Val  Asp  Ala  Leu  Gln  Thr  Ala  Leu
               12245                12250                         12255

Arg  Ala  Leu  Glu  Glu  Arg  His  Glu  Leu  Leu  Arg  Thr  Thr  Phe  Glu  Glu
               12260                12265                    12270

Gln  Asp  Gly  Val  Gly  Met  Gln  Ile  Val  His  Ser  Pro  Arg  Met  Arg  Asp
               12275                12280                    12285

Ile  Cys  Val  Val  Asp  Ile  Ser  Gly  Ala  Asn  Glu  Asp  Leu  Ala  Lys  Leu
               12290                12295                    12300

Lys  Glu  Glu  Gln  Gln  Ala  Pro  Phe  Asn  Leu  Ser  Thr  Glu  Val  Ala  Trp
12305               12310                    12315                         12320

Arg  Val  Ala  Leu  Phe  Lys  Ala  Gly  Glu  Asn  His  His  Ile  Leu  Ser  Ile
               12325                12330                         12335

Val  Met  His  His  Ile  Ile  Ser  Asp  Gly  Trp  Ser  Val  Asp  Ile  Phe  Gln
               12340                12345                    12350

Gln  Glu  Leu  Ala  Gln  Phe  Tyr  Ser  Val  Ala  Val  Arg  Gly  His  Asp  Pro
               12355                12360                    12365

Leu  Ser  Gln  Val  Lys  Pro  Leu  Pro  Ile  His  Tyr  Arg  Asp  Phe  Ala  Val
12370                    12375                    12380

Trp  Gln  Arg  Gln  Asp  Lys  Gln  Val  Ala  Val  His  Glu  Ser  Gln  Leu  Gln
12385               12390                    12395                         12400

Tyr  Trp  Ile  Glu  Gln  Leu  Ala  Asp  Ser  Thr  Pro  Ala  Glu  Ile  Leu  Ser
               12405                12410                         12415

Asp  Phe  Asn  Arg  Pro  Glu  Val  Leu  Ser  Gly  Glu  Ala  Gly  Thr  Val  Pro
               12420                12425                    12430

Ile  Val  Ile  Glu  Asp  Glu  Val  Tyr  Glu  Lys  Leu  Ser  Leu  Phe  Cys  Arg
               12435                12440                    12445

Asn  His  Gln  Val  Thr  Ser  Phe  Val  Val  Leu  Leu  Ala  Ala  Phe  Arg  Val
               12450                12455                    12460

Ala  His  Tyr  Arg  Leu  Thr  Gly  Ala  Glu  Asp  Ala  Thr  Ile  Gly  Thr  Pro
12465                    12470                    12475                    12480

Ile  Ala  Asn  Arg  Asn  Arg  Pro  Glu  Leu  Glu  Asp  Leu  Ile  Gly  Phe  Phe
                    12485                    12490                         12495

Val  Asn  Thr  Gln  Cys  Met  Arg  Ile  Ala  Leu  Glu  Glu  His  Asp  Asn  Phe
                    12500                    12505                         12510

Leu  Ser  Val  Val  Arg  Arg  Val  Arg  Ser  Thr  Ala  Ala  Ser  Ala  Phe  Glu
               12515                12520                    12525
```

-continued

```
Asn Gln Asp Val Pro Phe Glu Arg Leu Val Ser Ala Leu Leu Pro Gly
         12530               12535               12540

Ser Arg Asp Ala Ser Arg Asn Pro Leu Val Gln Leu Met Phe Val Val
12545               12550               12555               12560

His Ser Gln Arg Asn Leu Gly Lys Leu Gln Leu Glu Gly Leu Glu Gly
             12565               12570               12575

Glu Pro Thr Pro Tyr Thr Ala Thr Thr Arg Phe Asp Val Glu Phe His
         12580               12585               12590

Leu Phe Glu Gln Asp Lys Gly Leu Ala Gly Asn Val Val Phe Ala Ala
         12595               12600               12605

Asp Leu Phe Glu Ala Ala Thr Ile Arg Ser Val Val Glu Val Phe His
    12610               12615               12620

Glu Ile Leu Arg Arg Gly Leu Asp Gln Pro Asp Ile Ala Ile Ser Thr
12625               12630               12635               12640

Met Pro Leu Val Asp Gly Leu Ala Ala Leu Asn Ser Arg Asn Leu Pro
             12645               12650               12655

Ala Val Glu Asp Ile Glu Pro Asp Phe Ala Thr Glu Ala Ser Val Val
             12660               12665               12670

Asp Val Phe Gln Thr Gln Val Val Ala Asn Pro Asp Ala Leu Ala Val
             12675               12680               12685

Thr Asp Thr Ser Thr Lys Leu Thr Tyr Ala Glu Leu Asp Gln Gln Ser
    12690               12695               12700

Asp His Val Ala Ala Trp Leu Ser Lys Gln Lys Leu Pro Ala Glu Ser
12705               12710               12715               12720

Ile Val Val Val Leu Ala Pro Arg Ser Ser Glu Thr Ile Val Ala Cys
             12725               12730               12735

Ile Gly Ile Leu Lys Ala Asn Leu Ala Tyr Leu Pro Met Asp Ser Asn
             12740               12745               12750

Val Pro Glu Ala Arg Arg Gln Ala Ile Leu Ser Glu Ile Pro Gly Glu
             12755               12760               12765

Lys Phe Val Leu Leu Gly Ala Gly Val Pro Ile Pro Asp Asn Lys Thr
    12770               12775               12780

Ala Asp Val Arg Met Val Phe Ile Ser Asp Ile Val Ala Ser Lys Thr
12785               12790               12795               12800

Asp Lys Ser Tyr Ser Pro Gly Thr Arg Pro Ser Ala Ser Ser Leu Ala
             12805               12810               12815

Tyr Val Ile Phe Thr Ser Gly Ser Thr Gly Arg Pro Lys Gly Val Met
             12820               12825               12830

Val Glu His Arg Gly Val Ile Ser Leu Val Lys Gln Asn Ala Ser Arg
             12835               12840               12845

Ile Pro Gln Ser Leu Arg Met Ala His Val Ser Asn Leu Ala Phe Asp
    12850               12855               12860

Ala Ser Val Trp Glu Ile Phe Thr Thr Leu Leu Asn Gly Gly Thr Leu
12865               12870               12875               12880

Phe Cys Ile Ser Tyr Phe Thr Val Leu Asp Ser Lys Ala Leu Ser Ala
             12885               12890               12895

Ala Phe Ser Asp His Arg Ile Asn Ile Thr Leu Leu Pro Pro Ala Leu
             12900               12905               12910

Leu Lys Gln Cys Leu Ala Asp Ala Pro Ser Val Leu Ser Ser Leu Glu
         12915               12920               12925

Ser Leu Tyr Ile Gly Gly Asp Arg Leu Asp Gly Ala Asp Ala Thr Lys
    12930               12935               12940

Val Lys Asp Leu Val Lys Gly Lys Ala Tyr Asn Ala Tyr Gly Pro Thr
```

```
12945                     12950                    12955                    12960

Glu Asn Ser Val Met Ser Thr Ile Tyr Thr Ile Glu His Glu Thr Phe
                12965                 12970               12975

Ala Asn Gly Val Pro Ile Gly Thr Ser Leu Gly Pro Lys Ser Lys Ala
            12980                 12985             12990

Tyr Ile Met Asp Gln Asp Gln Gln Leu Val Pro Ala Gly Val Met Gly
           12995                 13000             13005

Glu Leu Val Val Ala Gly Asp Gly Leu Ala Arg Gly Tyr Thr Asp Pro
        13010                 13015             13020

Ser Leu Asn Thr Gly Arg Phe Ile His Ile Thr Ile Asp Gly Lys Gln
13025               13030              13035              13040

Val Gln Ala Tyr Arg Thr Gly Asp Arg Val Arg Tyr Arg Pro Arg Asp
              13045                 13050             13055

Tyr Gln Ile Glu Phe Phe Gly Arg Leu Asp Gln Gln Ile Lys Ile Arg
             13060                13065              13070

Gly His Arg Ile Glu Pro Ala Glu Val Glu Gln Ala Leu Leu Ser Asp
          13075               13080              13085

Ser Ser Ile Asn Asp Ala Val Val Ser Ala Gln Asn Lys Glu Gly
         13090              13095              13100

Leu Glu Met Val Gly Tyr Ile Thr Thr Gln Ala Ala Gln Ser Val Asp
13105                13110              13115                  13120

Lys Glu Glu Ala Ser Asn Lys Val Gln Glu Trp Glu Ala His Phe Asp
              13125                13130              13135

Ser Thr Ala Tyr Ala Asn Ile Gly Gly Ile Asp Arg Asp Ala Leu Gly
            13140                13145              13150

Gln Asp Phe Leu Ser Trp Thr Ser Met Tyr Asp Gly Ser Leu Ile Pro
         13155                  13160             13165

Arg Glu Glu Met Gln Glu Trp Leu Asn Asp Thr Met Arg Ser Leu Leu
            13170                 13175             13180

Asp Asn Gln Pro Pro Gly Lys Val Leu Glu Ile Gly Thr Gly Thr Gly
13185                13190              13195                  13200

Met Val Leu Phe Asn Leu Gly Lys Val Glu Gly Leu Gln Ser Tyr Ala
              13205                13210             13215

Gly Leu Glu Pro Ser Arg Ser Val Thr Ala Trp Val Asn Lys Ala Ile
           13220                13225              13230

Glu Thr Phe Pro Ser Leu Ala Gly Ser Ala Arg Val His Val Gly Thr
           13235                13240              13245

Ala Glu Asp Ile Ser Ser Ile Asp Gly Leu Arg Ser Asp Leu Val Val
             13250                13255             13260

Ile Asn Ser Val Ala Gln Tyr Phe Pro Ser Arg Glu Tyr Leu Ala Glu
13265                13270              13275                 13280

Leu Thr Ala Asn Leu Ile Arg Leu Pro Gly Val Lys Arg Ile Phe Phe
              13285                13290             13295

Gly Asp Met Arg Thr Tyr Ala Thr Asn Lys Asp Phe Leu Val Ala Arg
             13300                13305             13310

Ala Val His Thr Leu Gly Ser Asn Ala Ser Lys Ala Met Val Arg Gln
           13315                13320              13325

Gln Val Ala Lys Leu Glu Asp Asp Glu Glu Glu Leu Leu Val Asp Pro
13330                13335              13340

Ala Phe Phe Thr Ser Leu Ser Asp Gln Phe Pro Asp Glu Ile Lys His
13345              13350               13355               13360

Val Glu Ile Leu Pro Lys Arg Met Ala Ala Thr Asn Glu Leu Ser Ser
                13365               13370              13375
```

```
Tyr Arg Tyr Ala Ala Val Ile His Val Gly Gly His Gln Met Pro Asn
        13380                13385                  13390
Gly Glu Asp Glu Asp Lys Gln Trp Ala Val Lys Asp Ile Asn Pro Lys
        13395                13400                  13405
Ala Trp Val Asp Phe Ala Gly Thr Arg Met Asp Arg Gln Ala Leu Leu
        13410                13415                  13420
Gln Leu Leu Gln Asp Arg Gln Arg Gly Asp Asp Val Val Ala Val Ser
13425           13430                13435                  13440
Asn Ile Pro Tyr Ser Lys Thr Ile Met Glu Arg His Leu Ser Gln Ser
        13445                13450                  13455
Leu Asp Asp Asp Glu Asp Gly Thr Ser Ala Val Asp Gly Thr Ala Trp
        13460                13465                  13470
Ile Ser Arg Thr Gln Ser Arg Ala Lys Glu Cys Pro Ala Leu Ser Val
        13475                13480                  13485
Ala Asp Leu Ile Glu Ile Gly Lys Gly Ile Gly Phe Glu Val Glu Ala
        13490                13495                  13500
Ser Trp Ala Arg Gln His Ser Gln Arg Gly Gly Leu Asp Ala Val Phe
13505           13510                13515                  13520
His Arg Phe Glu Pro Pro Arg His Ser Gly His Val Met Phe Arg Phe
        13525                13530                  13535
Pro Thr Glu His Lys Gly Arg Ser Ser Ser Ser Leu Thr Asn Arg Pro
        13540                13545                  13550
Leu His Leu Leu Gln Ser Arg Arg Leu Glu Ala Lys Val Arg Glu Arg
        13555                13560                  13565
Leu Gln Ser Leu Leu Pro Pro Tyr Met Ile Pro Ser Arg Ile Thr Leu
        13570                13575                  13580
Leu Asp Gln Met Pro Leu Thr Ser Asn Gly Lys Val Asp Arg Lys Lys
13585           13590                13595                  13600
Leu Ala Arg Gln Ala Arg Val Ile Pro Arg Ser Ala Ala Ser Thr Leu
        13605                13610                  13615
Asp Phe Val Ala Pro Arg Thr Glu Ile Glu Val Val Leu Cys Glu Glu
        13620                13625                  13630
Phe Thr Asp Leu Leu Gly Val Lys Val Gly Ile Thr Asp Asn Phe Phe
        13635                13640                  13645
Glu Leu Gly Gly His Ser Leu Leu Ala Thr Lys Leu Ser Ala Arg Leu
        13650                13655                  13660
Ser Arg Arg Leu Asp Ala Gly Ile Thr Val Lys Gln Val Phe Asp Gln
13665           13670                13675                  13680
Pro Val Leu Ala Asp Leu Ala Ala Ser Ile Leu Gln Gly Ser Ser Arg
        13685                13690                  13695
His Arg Ser Ile Pro Ser Leu Pro Tyr Glu Gly Pro Val Glu Gln Ser
        13700                13705                  13710
Phe Ala Gln Gly Arg Leu Trp Phe Leu Asp Gln Phe Asn Ile Asp Ala
        13715                13720                  13725
Leu Trp Tyr Leu Ile Pro Phe Ala Leu Arg Met Arg Gly Pro Leu Gln
        13730                13735                  13740
Val Asp Ala Leu Ala Ala Ala Leu Val Ala Leu Glu Glu Arg His Glu
13745           13750                13755                  13760
Ser Leu Arg Thr Thr Phe Glu Glu Arg Asp Gly Val Gly Ile Gln Val
        13765                13770                  13775
Val Gln Pro Leu Arg Thr Thr Lys Asp Ile Arg Ile Ile Asp Val Ser
        13780                13785                  13790
Gly Met Arg Asp Asp Asp Ala Tyr Leu Glu Pro Leu Gln Lys Glu Gln
        13795                13800                  13805
```

```
Gln Thr Pro Phe Asp Leu Ala Ser Glu Pro Gly Trp Arg Val Ala Leu
    13810               13815               13820

Leu Lys Leu Gly Lys Asp Asp His Ile Leu Ser Ile Val Met His His
13825               13830               13835               13840

Ile Ile Ser Asp Gly Trp Ser Thr Glu Val Leu Gln Arg Glu Leu Gly
                13845               13850               13855

Gln Phe Tyr Leu Ala Ala Lys Ser Gly Lys Ala Pro Leu Ser Gln Val
            13860               13865               13870

Ala Pro Leu Pro Ile Gln Tyr Arg Asp Phe Ala Val Trp Gln Arg Gln
            13875               13880               13885

Glu Glu Gln Val Ala Glu Ser Gln Arg Gln Leu Asp Tyr Trp Lys Lys
            13890               13895               13900

Gln Leu Ala Asp Ser Ser Pro Ala Glu Leu Leu Ala Asp Tyr Thr Arg
13905               13910               13915               13920

Pro Asn Val Leu Ser Gly Glu Ala Gly Ser Val Ser Phe Val Ile Asn
                13925               13930               13935

Asp Ser Val Tyr Lys Ser Leu Val Ser Phe Cys Arg Ser Arg Gln Val
                13940               13945               13950

Thr Thr Phe Thr Thr Leu Leu Ala Ala Phe Arg Ala Ala His Tyr Arg
            13955               13960               13965

Met Thr Gly Ser Asp Asp Ala Thr Ile Gly Thr Pro Ile Ala Asn Arg
    13970               13975               13980

Asn Arg Pro Glu Leu Glu Asn Leu Ile Gly Cys Phe Val Asn Thr Gln
13985               13990               13995               14000

Cys Met Arg Ile Thr Ile Gly Asp Asp Glu Thr Phe Glu Ser Leu Val
                14005               14010               14015

Gln Gln Val Arg Ser Thr Thr Ala Thr Ala Phe Glu Asn Gln Asp Val
            14020               14025               14030

Pro Phe Glu Arg Ile Val Ser Thr Leu Ser Ala Gly Ser Arg Asp Thr
            14035               14040               14045

Ser Arg Asn Pro Leu Val Gln Leu Leu Phe Ala Val His Ser Gln Gln
        14050               14055               14060

Gly Leu Gly Arg Ile Gln Leu Asp Gly Val Val Asp Glu Pro Val Leu
14065               14070               14075               14080

Ser Thr Val Ser Thr Arg Phe Asp Leu Glu Phe His Ala Phe Gln Glu
            14085               14090               14095

Ala Asp Arg Leu Asn Gly Ser Val Met Phe Ala Thr Asp Leu Phe Gln
            14100               14105               14110

Pro Glu Thr Ile Gln Gly Phe Val Ala Val Val Glu Glu Val Leu Gln
            14115               14120               14125

Arg Gly Leu Glu Gln Pro Gln Ser Pro Ile Ala Thr Met Pro Leu Ala
            14130               14135               14140

Glu Gly Ile Ala Gln Leu Arg Asp Ala Gly Ala Leu Gln Met Pro Lys
14145               14150               14155               14160

Ser Asp Tyr Pro Arg Asn Ala Ser Leu Val Asp Val Phe Gln Gln Gln
                14165               14170               14175

Ala Met Ala Ser Pro Ser Thr Val Ala Val Thr Asp Ser Thr Ser Lys
            14180               14185               14190

Leu Thr Tyr Ala Glu Leu Asp Arg Leu Ser Asp Gln Ala Ala Ser Tyr
            14195               14200               14205

Leu Arg Arg Gln Gln Leu Pro Ala Glu Thr Met Val Ala Val Leu Ala
14210               14215               14220

Pro Arg Ser Cys Glu Thr Ile Ile Ala Phe Leu Ala Ile Leu Lys Ala
```

-continued

```
           14225                    14230                    14235                    14240
       Asn  Leu  Ala  Tyr  Met  Pro  Leu  Asp  Val  Asn  Thr  Pro  Ser  Ala  Arg  Met
                             14245                    14250                    14255
       Glu  Ala  Ile  Ile  Ser  Ser  Val  Pro  Gly  Arg  Arg  Leu  Ile  Leu  Val  Gly
                             14260                    14265                    14270
       Ser  Gly  Val  Arg  His  Ala  Asp  Ile  Asn  Val  Pro  Asn  Ala  Lys  Thr  Met
                             14275                    14280                    14285
       Leu  Ile  Ser  Asp  Thr  Val  Thr  Gly  Thr  Asp  Ala  Ile  Gly  Thr  Pro  Glu
                             14290                    14295                    14300
       Pro  Leu  Val  Val  Arg  Pro  Ser  Ala  Thr  Ser  Leu  Ala  Tyr  Val  Ile  Phe
       14305                    14310                    14315                    14320
       Thr  Ser  Gly  Ser  Thr  Gly  Lys  Pro  Lys  Gly  Val  Met  Val  Glu  His  Arg
                             14325                    14330                    14335
       Ala  Ile  Met  Arg  Leu  Val  Lys  Asp  Ser  Asn  Val  Val  Thr  His  Met  Pro
                             14340                    14345                    14350
       Pro  Ala  Thr  Arg  Met  Ala  His  Val  Thr  Asn  Ile  Ala  Phe  Asp  Val  Ser
                             14355                    14360                    14365
       Leu  Phe  Glu  Met  Cys  Ala  Thr  Leu  Leu  Asn  Gly  Gly  Thr  Leu  Val  Cys
       14370                    14375                    14380
       Ile  Asp  Tyr  Leu  Thr  Leu  Leu  Asp  Ser  Thr  Met  Leu  Arg  Glu  Thr  Phe
       14385                    14390                    14395                    14400
       Glu  Arg  Glu  Gln  Val  Arg  Ala  Ala  Ile  Phe  Pro  Pro  Ala  Leu  Leu  Arg
                             14405                    14410                    14415
       Gln  Cys  Leu  Val  Asn  Met  Pro  Asp  Ala  Ile  Gly  Met  Leu  Glu  Ala  Val
                             14420                    14425                    14430
       Tyr  Val  Ala  Gly  Asp  Arg  Phe  His  Ser  Arg  Asp  Ala  Arg  Ala  Thr  Gln
                             14435                    14440                    14445
       Ala  Leu  Ala  Gly  Pro  Arg  Val  Tyr  Asn  Ala  Tyr  Gly  Pro  Thr  Glu  Asn
                             14450                    14455                    14460
       Ala  Ile  Leu  Ser  Thr  Ile  Tyr  Asn  Ile  Asp  Lys  His  Asp  Pro  Tyr  Val
       14465                    14470                    14475                    14480
       Asn  Gly  Val  Pro  Ile  Gly  Ser  Ala  Val  Ser  Asn  Ser  Gly  Ala  Tyr  Val
                             14485                    14490                    14495
       Met  Asp  Arg  Asn  Gln  Gln  Leu  Leu  Pro  Pro  Gly  Val  Met  Gly  Glu  Leu
                             14500                    14505                    14510
       Val  Val  Thr  Gly  Glu  Gly  Val  Ala  Arg  Gly  Tyr  Thr  Asp  Ala  Ser  Leu
                             14515                    14520                    14525
       Asp  Thr  Asp  Arg  Phe  Val  Thr  Val  Thr  Ile  Asp  Gly  Gln  Arg  Gln  Arg
                             14530                    14535                    14540
       Ala  Tyr  Arg  Thr  Gly  Asp  Arg  Val  Arg  Tyr  Arg  Pro  Lys  Gly  Phe  Gln
       14545                    14550                    14555                    14560
       Ile  Glu  Phe  Phe  Gly  Arg  Leu  Asp  Gln  Gln  Ala  Lys  Ile  Arg  Gly  His
                             14565                    14570                    14575
       Arg  Val  Glu  Leu  Gly  Glu  Val  Glu  His  Ala  Leu  Leu  Ser  Glu  Asn  Ser
                             14580                    14585                    14590
       Val  Thr  Asp  Ala  Ala  Val  Val  Leu  Arg  Thr  Met  Glu  Glu  Glu  Asp  Pro
                             14595                    14600                    14605
       Gln  Leu  Val  Ala  Phe  Val  Thr  Thr  Asp  His  Glu  Tyr  Arg  Ser  Gly  Ser
                             14610                    14615                    14620
       Ser  Asn  Glu  Glu  Glu  Asp  Pro  Tyr  Ala  Thr  Gln  Ala  Ala  Gly  Asp  Met
       14625                    14630                    14635                    14640
       Arg  Lys  Arg  Leu  Arg  Ser  Leu  Leu  Pro  Tyr  Tyr  Met  Val  Pro  Ser  Arg
                             14645                    14650                    14655
```

Val Thr Ile Leu Arg Gln Met Pro Leu Asn Ala Asn Gly Lys Val Asp
14660                    14665                    14670

Arg Lys Asp Leu Ala Arg Arg Ala Gln Met Thr Pro Thr Ala Ser Ser
         14675                    14680                    14685

Ser Gly Pro Val His Val Ala Pro Arg Asn Glu Thr Glu Ala Ala Ile
    14690                    14695                    14700

Cys Asp Glu Phe Glu Thr Ile Leu Gly Val Lys Val Gly Ile Thr Asp
14705                    14710                    14715                    14720

Asn Phe Phe Glu Leu Gly Gly His Ser Leu Leu Ala Thr Lys Leu Ala
             14725                    14730                    14735

Ala Arg Leu Ser Arg Arg Met Gly Leu Arg Ile Ser Val Lys Asp Leu
         14740                    14745                    14750

Phe Asp Asp Pro Val Pro Val Ser Leu Ala Gly Lys Leu Glu Gln Gln
         14755                    14760                    14765

Gln Gly Phe Ser Gly Glu Asp Glu Ser Ser Thr Val Gly Ile Val Pro
         14770                    14775                    14780

Phe Gln Leu Leu Pro Ala Glu Met Ser Arg Glu Ile Ile Gln Arg Asp
14785                    14790                    14795                    14800

Val Val Pro Gln Ile Glu Asn Gly His Ser Thr Pro Leu Asp Met Tyr
                 14805                    14810                    14815

Pro Ala Thr Gln Thr Gln Ile Phe Phe Leu His Asp Lys Ala Thr Gly
             14820                    14825                    14830

His Pro Ala Thr Pro Pro Leu Phe Ser Leu Asp Phe Pro Glu Thr Ala
         14835                    14840                    14845

Asp Cys Arg Arg Leu Ala Ser Ala Cys Ala Ala Leu Val Gln His Phe
         14850                    14855                    14860

Asp Ile Phe Arg Thr Val Phe Val Ser Arg Gly Gly Arg Phe Tyr Gln
14865                    14870                    14875                    14880

Val Val Leu Ala His Leu Asp Val Pro Val Glu Val Ile Glu Thr Glu
                 14885                    14890                    14895

Gln Glu Leu Asp Glu Val Ala Leu Ala Leu His Glu Ala Asp Lys Gln
             14900                    14905                    14910

Gln Pro Leu Arg Leu Gly Arg Ala Met Leu Arg Ile Ala Ile Leu Lys
         14915                    14920                    14925

Arg Pro Gly Ala Lys Met Arg Leu Val Leu Arg Met Ser His Ser Leu
         14930                    14935                    14940

Tyr Asp Gly Leu Ser Leu Glu His Ile Val Asn Ala Leu His Ala Leu
14945                    14950                    14955                    14960

Tyr Ser Asp Lys His Leu Ala Gln Ala Pro Lys Phe Gly Leu Tyr Met
             14965                    14970                    14975

His His Met Ala Ser Arg Arg Ala Glu Gly Tyr Asn Phe Trp Arg Ser
         14980                    14985                    14990

Ile Leu Gln Gly Ser Ser Met Thr Ser Leu Lys Arg Ser Val Gly Ala
         14995                    15000                    15005

Leu Glu Ala Met Thr Pro Ser Ala Gly Thr Trp Gln Thr Ser Lys Ser
         15010                    15015                    15020

Ile Arg Ile Pro Pro Ala Ala Leu Lys Asn Gly Ile Thr Gln Ala Thr
15025                    15030                    15035                    15040

Leu Phe Thr Ala Ala Val Ser Leu Leu Leu Ala Lys His Thr Lys Ser
             15045                    15050                    15055

Thr Asp Val Val Phe Gly Arg Val Val Ser Gly Arg Gln Asp Leu Ser
             15060                    15065                    15070

Ile Asn Cys Gln Asp Ile Val Gly Pro Cys Ile Asn Glu Val Pro Val
             15075                    15080                    15085

Arg   Val   Arg   Ile   Asp   Glu   Gly   Asp   Asp   Met   Gly   Gly   Leu   Leu   Arg   Ala
              15090                   15095                     15100

Ile   Gln   Asp   Gln   Tyr   Thr   Ser   Ser   Phe   Arg   His   Glu   Thr   Leu   Gly   Leu
        15105                         15110                     15115                           15120

Gln   Glu   Val   Lys   Glu   Asn   Cys   Thr   Asp   Trp   Thr   Asp   Ala   Thr   Lys   Glu
                                15125                     15130                           15135

Phe   Ser   Cys   Cys   Ile   Ala   Phe   Gln   Asn   Leu   Asn   Leu   His   Pro   Glu   Ala
                          15140                   15145                           15150

Glu   Ile   Glu   Gly   Gln   Gln   Ile   Arg   Leu   Glu   Gly   Leu   Pro   Ala   Lys   Asp
                          15155                         15160                     15165

Gln   Ala   Arg   Gln   Ala   Asn   Gly   His   Ala   Pro   Asn   Gly   Thr   Asn   Gly   Thr
                          15170                   15175                           15180

Asn   Gly   Thr   Asn   Gly   Thr   Asn   Gly   Ala   Asn   Gly   Thr   Asn   Gly   Thr   Asn
        15185                         15190                     15195                           15200

Gly   Thr   Asn   Gly   Thr   His   Ala   Asn   Gly   Ile   Asn   Gly   Ser   Asn   Gly   Val
                                15205                     15210                           15215

Asn   Gly   Arg   Asp   Ser   Asn   Val   Val   Ser   Ala   Ala   Gly   Asp   Gln   Ala   Pro
                          15220                         15225                     15230

Val   His   Asp   Leu   Asp   Ile   Val   Gly   Ile   Pro   Glu   Pro   Asp   Gly   Ser   Val
                          15235                         15240                     15245

Lys   Ile   Gly   Ile   Gly   Ala   Ser   Arg   Gln   Ile   Leu   Gly   Glu   Lys   Val   Val
              15250                         15255                     15260

Gly   Ser   Met   Leu   Asn   Glu   Leu   Cys   Glu   Thr   Met   Leu   Ala   Leu   Ser   Arg
        15265                         15270                           15275                     15280

Thr ( 2 ) INFORMATION FOR SEQ ID NO:3:

( i ) SEQUENCE CHARACTERISTICS:
        ( A ) LENGTH: 178 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Tolypocladium geodes ( x i ) SEQUENCE DESCRIPTION: SEQ ID NO:3:

ATGCAACTAT　　CGGCTCTCCA　　ATTGCGAACA　　GAAATCGAGC　　AGAGCTTGAG　　GGCCTTATTG　　　　60

GCTGTTTTGT　　GAATACTCAG　　TGTATGAGAC　　TGCCAGTTAC　　CGATGAAGAT　　ACATTCGCCA　　　120

ATTTGATTGA　　CTGTGTACGA　　GAGACGTCAA　　CCGAGGCCTT　　GAGCACCAAG　　ATATCCTT　　　　178

( 2 ) INFORMATION FOR SEQ ID NO:4:

( i ) SEQUENCE CHARACTERISTICS:
        ( A ) LENGTH: 1713 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO (v i) ORIGINAL SOURCE:
    (A) ORGANISM: Necosmospora vasinfecta (x i) SEQUENCE DESCRIPTION: SEQ ID NO:4:

| | | | | | | |
|---|---|---|---|---|---|---|
| ACATCGGGGG | TATTGATCGC | GATGCCCTCG | GACAGGACTT | CTTATCCTGG | ACATCCATGT | 60 |
| ACGACGGCTC | ATTGATTCCC | CGGGAAGAGA | TGCAGGAATG | GCTCAGCGAC | ACTATGCACT | 120 |
| CACTCCTCGA | CAACCAGCCA | CCCGGAAGAG | TGCTCGAGAT | CGGAACTGGT | ACCGGTATGG | 180 |
| TGCTTTTCAA | TCTCGGCAAG | GTTGAGGGAC | TACAGAGCTA | TGCCGGTCTT | GAGCCCTCGC | 240 |
| GCTCCGTCAC | TGCCTGGGTT | AACAAGGCAA | TCGAAACTTT | CCCAAGCCTG | GCAGGAAGCG | 300 |
| CCCGAGTCCA | CGTTGGAACC | GCCGAGGATG | TCAGCTCCAT | CAATGGACTG | CGTGCCGATC | 360 |
| TCGTTGTGAT | CAACTCGGTC | GCCCAATACT | TCCCAAGTCG | AGAATATCTC | GCTGAGCTGA | 420 |
| CGGCCAACTT | GATTCGACTG | CCCGGCGTCA | AGCGTATTTT | CTTCGGCGAC | ATGAGAACCT | 480 |
| ATGCCACCAA | TAAGGACTTC | TTGGTGGCAC | GAGCAGTCCA | TACCCTAGGG | TCCAATGCAT | 540 |
| CTAAGGCCAT | GGTTCGACAA | CAGGTGGCCA | AGCTTGAAGA | TGACGAGGAA | GAGTTGCTTG | 600 |
| TTGACCCTGC | CTTCTTCACC | AGCCTGAGCG | ACCAGTTCCC | TGACGAAATC | AAGCACGTCG | 660 |
| AGATTCTGCC | AAAGAGGATG | GCCGCGACCA | ACGAACTCAG | CTCTTACCGA | TATGCTGCTG | 720 |
| TTATTCATGT | GGGAGGCCAC | GAGATGCCGA | ATGGGGAGGA | TGAGGATAAG | CAATGGGCTG | 780 |
| TCAAGGATAT | CGATCCGAAG | GCCTGGGTGG | ACTTCGCCGG | CACGAGGATG | GACCGTCAGG | 840 |
| CTCTCTTGCA | GCTCCTCCAG | GACCGCCAAC | GTGGCGATGA | CGTTGTTGCC | GTCAGTAACA | 900 |
| TCCCATACAG | CAAGACCATC | ATGGAGCGCC | ATCTGTCTCA | GTCACTTGAC | GATGACGAGG | 960 |
| ACGGCACTTC | AGATGCAGAC | GGAACGGCCT | GGATATCGGC | CACTCAATCA | CGGGCGAAGG | 1020 |
| AATGCCCTGC | TCTCTCAGTG | GCCGACCTGA | TTGAGATTGG | TAAGGGGATC | GGCTTCCAAG | 1080 |
| TTGAGACCAG | CTGGGCTCGA | CAACACTCCC | AGCGCGGCGG | ACTCGATGCT | GTTTTCCACC | 1140 |
| GATTCGAAAA | ACCAAGACAC | TCGGGTCATG | TCATGTTCAG | GTTCCCAACT | GAACACAAGG | 1200 |
| GGCCGGTCTT | CGAGCAGTCT | CACGAATCGC | CCGCTACACC | TGGTTCAGAG | CCGCCGGCTG | 1260 |
| GAGGCAAAGG | TCCGCGAGCG | GCTGCAATCG | CTGCTTCCAT | CGTACATGAT | TCCCTCTCGG | 1320 |
| ATCATGTTGC | TCGATCAGAT | GCCTCTCACG | TCCAACGGCA | AGGTGGATCG | CAAGAAGCTC | 1380 |
| GCTCGACAAG | CCCGGGTCAT | CCCAACAATT | GCCGCAAGCA | CGTTGGACTT | TGTGGCGCGC | 1440 |
| ACGCACGGAA | ATCGAGGTCG | GTTCTCTGCG | AAGAATTTAC | CGATCTACTA | GGCGTCAAGG | 1500 |
| TCGGCATTAC | AGACAACTTC | TTCGAGTTGG | GCGGCCATTC | GCTGCTGGCC | ACGAAACTGA | 1560 |
| GCGCACGTCT | AAGTCGCAGA | CTGGACGCCG | GTGTCACTGT | GAAGCAGATC | TTTGACCAGC | 1620 |
| CAGTACTTGC | TGATCTTGCT | GCTTCTATTC | GTCAAGGCTC | GTCCCGTCAC | AGGTCTATCC | 1680 |
| CGTCTTTACC | CTACGAAGGA | CCCGTGGAGC | AGT | | | 1713 |

(2) INFORMATION FOR SEQ ID NO:5:

(i) SEQUENCE CHARACTERISTICS:
        (A) LENGTH: 655 base pairs
        (B) TYPE: nucleic acid
        (C) STRANDEDNESS: single
        (D) TOPOLOGY: unknown (i i) MOLECULE TYPE: cDNA (i i i) HYPOTHETICAL: NO (i v) ANTI-SENSE: NO (v i) ORIGINAL SOURCE:
        (A) ORGANISM: Tolypocladium niveum (B) STRAIN: ATCC 34921

(x i) SEQUENCE DESCRIPTION: SEQ ID NO:5:

| | | | | | | |
|---|---|---|---|---|---|---|
| CATCAGCAAT | CATGGGCAAC | AAAGTCTTCT | TCGACATTGA | GTGGGAGGGC | CCCGTCATGC | 60 |
| AGGGTTGCAA | GCCTACCTCT | ACCGTCAAAG | AGCAGTCTGG | TCGCATCAAC | TTCAAGCTGT | 120 |
| ACGATGACGT | CGTCCCCAAG | ACCGCCGAGA | ACTTCCGCGC | TCTCTGCACC | GGCGAGAAGG | 180 |
| GCTTCGGCTA | CGAGGGCTCG | TCCTTCCACC | GTATCATCCC | CGAGTTCATG | CTCCAGGGCG | 240 |
| GCGACTTCAC | CCGCGGTAAC | GGCACTGGCG | GCAAGTCCAT | CTACGGCGAG | AAGTTTGCCG | 300 |
| ATGAGAACTT | CCAGCTGAAG | CACGACCGCC | CCGGTCTGCT | GTCCATGGCT | AACGCTGGCC | 360 |
| CCAACACCAA | CGGCTCCCAG | TTCTTCGTCA | CCACCGTCGT | CACCTCGTGG | CTCAACGGCC | 420 |
| ACCACGTCGT | CTTCGGCGAG | GTCGCTGACC | AGGAGTCCCT | GGACGTCGTC | AAGGCCCTTG | 480 |
| AGGCCACTGG | CTCTGGTAGC | GGCGCTGTCA | AGTACAACAA | GCGCGCCACC | ATTGTCAAGT | 540 |
| CTGGCGAGCT | GTAAGCTATG | GCATCTGTGT | ATCTTGCGAT | TTCCTGCACC | CAATTCGGAC | 600 |
| GGACAAAAGA | GGCGCTGCCC | ACAGCAAGGA | CCTTTGGTTC | ACGGGACGGC | TTGAA | 655 |

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (i i) MOLECULE TYPE: cDNA (i i i) HYPOTHETICAL: NO (i v) ANTI-SENSE: NO (x i) SEQUENCE DESCRIPTION: SEQ ID NO:6:

| | | | |
|---|---|---|---|
| GGGATATCGT | GAATTGTAAT | ACGACTCACT | ATA | 33 |

(2) INFORMATION FOR SEQ ID NO:7:

(i) SEQUENCE CHARACTERISTICS:
        (A) LENGTH: 2157 base pairs
        (B) TYPE: nucleic acid
        (C) STRANDEDNESS: single
        (D) TOPOLOGY: unknown (i i) MOLECULE TYPE: cDNA (i i i) HYPOTHETICAL: NO (i v) ANTI-SENSE: NO (x i) SEQUENCE DESCRIPTION: SEQ ID NO:7:

| | | | | | | |
|---|---|---|---|---|---|---|
| GGATCCGTGA | ATTGTAATAC | GACTCACTAT | AGGGCGAATT | CGCTCGACGT | CACCTAGGAG | 60 |
| ATCAGCCAGC | TCCTTGGCCC | TGTTCCGCAC | GTTGATGCCC | TGGTCTTTGC | CGTTTGGATC | 120 |
| GATGAAGTGG | AACTGGCGCA | GCATCTTCAA | AAGTGTGATG | TGTCCCCGAG | CGTCATCAAT | 180 |
| CACACGCTCA | GAGCCATGCT | TGACGAGGAA | CTCGAGCAGT | TGCAGAGCCT | TGTAGATCTG | 240 |
| GCGCCACTCC | TCGGCCGACT | TCTCCGTGAA | CCGTCGATAT | ATCATCGGCA | TGATCTCGTT | 300 |
| GAGGGTTTGG | CTGGTTCTGT | TAGCTGAAGC | CGGGCTGTTC | AGTCGTCGAA | CCGCGTACTA | 360 |
| GTTGAAGGTG | CCATTGGCAA | TCTCCTGCAT | AATACTGGAC | GATGCTCCCC | ATGGCTCGTT | 420 |
| GTTCGTTGCC | TCTCGGACCT | AGTACACGGA | GTTAGCCACC | GTGTTAACAA | ACCGTCGCGG | 480 |
| CCGCAGACTA | ACCTTGGACT | CCATCTCGGT | ATAGTTCATA | ACAGCTACAT | GCCAGGTCAG | 540 |

-continued

```
CATTGGACGC GCCAGGGCTG AGGTCAGGCC TGGTACCATT TTGCGCCTTT CGGAACCCAG   600
CCTTGAGGTC GTACAAGGTC AGGTTGGAGA CTGTGTTCTT GATGTCGTTC AAGTCCATTT   660
TGGCAGATTC GACTTAGCGA GACCGGCCGG GAGCGGCAGA GGAGTTGTCG ATTCAGCACG   720
AGTCGCTGAT GAGCGATGGT TGTGGTGCAA GTCGATGGTC CGAGGGCGGG TGGTAGAGGT   780
GCTTGTCGCG ATGGACAGCT GGACTTTCGG GCCGCCAGCG ACACCTACCC GGCCTTGATG   840
GGTCAGAGGG ATGATCACGT GATATGGGTC GGAGTCGCAT CGTACTTCGT ACCAGCATCA   900
TCTCCAAGCC AGAGGCAGCA GAGATTATAT GACTGCAAAT GTGAAACGAA ATAAACCGTC   960
AATATGGTAT TTATGTTGGC AATTGCATGA TGCATCCCGG TGGAATTGAA CTAGAACGTC  1020
GAGGGCTTGC ATACCAGAGG CTGCGGGTGC ATCGTGGGCA GCGGTACCTG AGACTTCAGG  1080
CCAGAACGAC TGCTAATAAG CCGCGACGGA GCCAAAACTT TTCCCCTTTC CAGAGGCTCT  1140
CAGCTTTCGA CTCAGCCATT TGAACTTGCG ACTCAAGCCC GTTCATAACA CTTCATCTCT  1200
TGTACTTCTA CCGCATTACC TCCTGTACGA ATTGTAATCC CAGGTATGTC TATTTTCCTG  1260
TTGTTCTCGT CACATGCCCT CCCCAGCATG CGCAATGTCT TTGGACAACG CAGCTCCTCT  1320
CGACACATCA CAAAGGCTTC ACCCAGCAGA GCACGCGAGA GCCTGCGCGC GACAGCCTGC  1380
GAGCGACATG CAGCGCTTCC CTGGAAGCCA ACTGCACCAG CCTGGAAAGT TGCGCAGTTT  1440
GCCAGGGGGC CTCCGTCCCC CAGAATGGAT GGCACTCCTC GGCTTGACCT GGAGCGCTGC  1500
TCCCGATCAA GCCAGAGCCC GCCGGCGATG GGGACTGGCC GCGCCAGCCT CTGCACATGA  1560
GTGTGCTGGT TGGCTGGAGG TGGGTGGCCT TTGGCCTCCC AACCAGTCCC CACCATTTGC  1620
TGGAAGCTGC TGCAGCTGGT CGGAACGCAC CCAAGCCGTT GAGCTCAGCG CTCTGTCGGG  1680
TCGAGCGCCC ATTGGGGTTC CCGCGAAGGT CCTTTGACTG GGCCGGGGCC ACTCGTCTTG  1740
CCGGCCAGAG CTGAGCTCGC TGGTCTGGCA GCGACAGCAG CCGGGAGCTC CGTTGTCTAG  1800
GCGATGAGCG CAGCGGCCAG AGCTCCGGGC CGGATCGGTG ACCTCACAGC CGTGGAAGCT  1860
CCTGGGCCCC CGAATCAAGG ACCGCAATTC CACGTGACTG GCCGGTTGCT CCCCTTCCGG  1920
CATTGCCCGC CCCGCTATTA CACCCCTTTG CGCGCCCTGG TTGGTTCAAA GTCCCACCGC  1980
TAACTTTTAA CCCCTCCAGC AGCCTTCAAA ATGAAGTCAA CGCTCCTTCG ACCCCTCCTA  2040
CCCCGCTATA AGCTCTGCTC CCCCGGGTCA AGATCTTTCC CTCTTCCACA ACTTGCATCA  2100
GCTTCCAACA CATTCCGAGC TGCTCGATTC TTCTCCGCAA CATCAGCAAT CATCGAT     2157
```

( 2 ) INFORMATION FOR SEQ ID NO:8:

( i ) SEQUENCE CHARACTERISTICS:
( A ) LENGTH: 20 base pairs
( B ) TYPE: nucleic acid
( C ) STRANDEDNESS: single
( D ) TOPOLOGY: unknown ( i i ) MOLECULE TYPE: cDNA ( i i i ) HYPOTHETICAL: YES ( i v ) ANTI-SENSE: NO ( v i ) ORIGINAL SOURCE:
( A ) ORGANISM: Tolypocladium niveum ( x i ) SEQUENCE DESCRIPTION: SEQ ID NO:8:

```
GCVTCDATVT TVAAYTGVTC   20
```

CYCLOSPORIN SYNTHETASE

This is a continuation of application Ser. No. 08/263,960, filed Jun. 20, 1994 and now abandoned, which is a continuation of application Ser. No. 08/090,552, filed Jul. 9, 1993 and now abandoned.

This invention relates to nucleotide sequences which code for enzymes possessing cyclosporin synthetase-like activity and to methods for the production of cyclosporin and cyclosporin derivatives using these sequences.

The fungus *Tolypocladium niveum* (previously known as *Tolypocladium inflatum* GAMS) produces cyclosporins, a group of neutral cyclic peptides composed of eleven amino acids. Other fungi have been found which may form cyclosporins (Dreyfuss, 1986; Nakajima et al., 1989) but *Tolypocladium niveum* is the most important organism for the production of cyclosporins by fermentation. Cyclosporins exhibit remarkable biological effects: for example cyclosporin A, the main metabolite, is a potent immunosuppressant (Borel et al., 1976). An enzyme has been identified which catalyses the entire peptide biosynthesis of cyclosporin and is therefore called cyclosporin synthetase (Zocher et al., 1986, Billich and Zocher 1987). The biosynthesis proceeds non-ribosomally by a thiotemplate process, as has also been described for other peptide synthetases (Kleinkauf and von Döhren 1990). Each amino acid is first activated in the form of an adenylate, then bound in the form of a thioester and linked with the following amino acid to the peptide. In the case of cyclosporin A, seven of the amino acids, bound as thioesters, are methylated before they are linked to the preceding amino acid in a peptide bond. This methylation function is an integral constituent of the enzyme polypeptide (Lawen and Zocher 1990). Including the cyclisation reaction, cyclosporin synthetase performs at least 40 reactions.

Cyclosporin A contains three non-proteinogenic amino acids: D-alanine in position 8, α-aminobutyric acid in position 2 and, in position 1, the unusual amino acid (4R)-4-[(E)-2-butenyl]-4-methyl-L-threonine (Bmt or C9 amino acid). All three amino acids must be each prepared by a biosynthetic pathway which is independent of the primary biosynthetic pathway. Cyclosporin synthetase does not possess an alanine-racemase function (Kleinkauf and von Döhren 1990) and thus, D-alanine cannot be produced by cyclosporin synthetase by epimerisation of enzyme-bound L-alanine, as is the case for other peptide antibiotics whose biosynthesis mechanism is known.

Although attempts have been made to isolate and characterize cyclosporin synthetase in terms of its amino acid sequence, because of the complexity and size of the enzyme this has not to date been possible. Hence it has not been possible to characterize the DNA coding for cyclosporin synthetase.

This invention provides a nucleotide sequence which codes for an enzyme possessing cyclosporin synthetase-like activity. In the present specification, an enzyme possessing cyclosporin synthetase-like activity is an enzyme which catalyses the peptide biosynthesis of cyclosporins and structurally related peptides and derivatives.

Preferably, the nucleotide sequence codes for cyclosporin synthetase or an enzyme which is at least 70% (for example, at least 80, 90 or 95%) homologous to it and which possesses cyclosporin synthetase-like activity.

Preferably, the nucleotide sequence codes for an enzyme which possesses cyclosporin synthetase-like activity and in which at least one amino acid recognition unit is different from that of cyclosporin synthetase.

Preferably, the nucleotide sequence comprises the sequence represented in SEQ ID NO:1 or a sequence which hybridises to it under conditions of reduced stringency or, more preferably, stringent conditions. Stringent conditions include hybridisation at 42° C. in 6×SSPE, 50% formamide, 5×Denhardt's solution, and 0.1% SDS and washing three times for 10 minutes in 2×SSC, 0.1% SDS and twice for 30 minutes in 0.2×SSC, 0.1% SDS at 65° C. Reduced stringency conditions include a washing temperature of 60° C. Even more preferably the nucleotide sequence codes for an enzyme having the amino acid sequence of SEQ ID NO:2. The nucleotide sequence may have a restriction map as represented in FIG. 1.

In another aspect, the invention provides a recombinant vector containing a nucleotide sequence as defined above. The vector may include the endogenous promoter for cyclosporin synthetase or may include some other suitable promoter. A suitable promoter region is illustrated in SEQ ID NO:7. The recombinant vector may be in the form of a plasmid, a cosmid, a P1-vector or a YAC-vector. The invention also extends to host cells carrying the vector. Preferably the host cell is a *Tolypocladium niveum* cell.

The invention also provides a process for the production of cyclosporin or a cyclosporin derivative, comprising cultivating a host cell as defined above and causing the host cell to produce the cyclosporin or cyclosporin derivative.

The invention also provides a method for the production of a cyclosporin derivative comprising altering the DNA sequence coding for cyclosporin synthetase so that the enzyme causes the production of the cyclosporin derivative, placing the altered DNA sequence in a vector, transforming a host cell with the vector, and causing the host cell to produce the cyclosporin derivative. Preferably the DNA sequence coding for cyclosporin synthetase is altered by changing the fragments that code for amino acid recognition units. Alterations may be made using standard techniques such as those based on PCR procedures. Point deletions, mutations and insertions, as well as larger alterations are possible.

This specification describes the isolation and characterisation of the gene for cyclosporin synthetase from *Tolypocladium niveum* and the use of the gene in genetically engineering cells, including *Tolypocladium niveum* cells. While a protocol for the isolation of cyclosporin synthetase from *Tolypocladium niveum* was published in 1990 (Lawen and Zocher 1990), it is however not suitable for extracting large quantities of homogeneous enzyme in a short period of time. Also, in the publication, the synthetase was attributed an $M_r$ of approximately 650,000 Dalton. It may, however, justifiably be assumed from sedimentation analyses with fluorescence-labelled protein (Lawen et al., 1992) and by extrapolation from the protein size of comparable enzymes that cyclosporin synthetase has an $M_r$ of approximately 1,500 kDa. The enzyme occurs as a single polypeptide chain and cannot be decomposed into subunits by either denaturing or reducing agents (Lawen and Zocher 1990).

The enormous size of the enzyme means that a strategy for amino acid sequencing which differs from the customarily used route must be used. Substantially more homogeneous material is required than is generally used to perform fragmentation tests. It is for this reason that a protocol was developed for cyclosporin synthetase which may, in principle, also be applied to analogous enzymes from other microorganisms and, in the practical example of the purification of the enzyme from *Tolypocladium niveum* (example 1), gave rise to a substantial improvement in terms of yield and the amount of time required.

Purification may initially proceed according to customary processes. Cell disruption may be performed, for example, with a high pressure homogeniser or a glass bead mill; the cells being present in moist or lyophilised state. If the cells are moist, pressure disruption is conveniently performed, for example with a Maunton Gaulin apparatus. Lyophilised cells are conveniently broken up by grinding in a mortar under liquid nitrogen.

The crude extract so obtained is clarified by centrifugation. The nucleic acids are removed by precipitating them from the extract using customary reagents for this purpose; polyethyleneimine or protamine sulphate are, for example, used. The nucleic acid precipitation also removes fine suspended particles, which can disturb subsequent purification stages. Then the proteins may be precipitated out of the clarified crude extract to provide the enzyme in a more concentrated form. The protein precipitation is customarily performed with ammonium sulphate. For cyclosporin synthetase, saturation to 50% is sufficient to achieve almost complete precipitation. After this step, the enzyme is in an enriched and highly concentrated state.

In principle, all chromatographic methods are suitable for further purification of the enzyme, such as ion-exchange chromatography and gel permeation chromatography. With very large proteins, gel permeation chromatography is particularly suitable as a very selective purification step. If the correct molecular sieve is chosen, an approximately 90% homogeneous protein preparation may be obtained in a single step. Analysis of purity is performed in SDS polyacrylamide gels (preferably gradient gels 4–15%).

The purification process used produces stable, at least 90% homogeneous, active enzyme preparations, as is necessary for characterisation of enzyme kinetics or protein chemistry. In Example 1, the protocol described in detail for *Tolypocladium niveum*, in comparison with the published method, reduces the time required from 4 days to 10 hours and increases the yield by approximately a factor of 4.

With a protein of this exceptional size, the requirement for amino acid sequences to identify the gene or gene product correctly is naturally greater than for an average-sized protein. Apart from the possibility of N-terminal blocking, it is also not possible to prepare a protein of this size in such a way that it is suitable for N-terminal sequencing. For these reasons, it is necessary to obtain a sufficient number of internal amino acid sequences.

However, when a protein of this size is fragmented, so many fragments are produced (theoretically approximately 700, assuming one cleavage every 20 amino acids) that the standard method of completely fragmenting the, protein and purifying the fragments by high-pressure reversed-phase chromatography (HP-RPC) is not practicable. For this reason, fragmentation is performed under conditions which are sub-optimal for the relevant endoproteinases to give substantially larger fragments.

Cyclosporin synthetase is cleaved by adjusting the pH. In particular, cleavage into large fragments of up to 200 kDa is achieved by adjusting the pH to approximately 7.5 in a HEPES buffer with the addition of EDTA and DTT. The fragments obtained in this manner may be isolated and enriched as is conventional, for example by using chromatography and electrophoresis, such as the combination of anion exchange chromatography on MonoQ with HP-RPC or the combination of MonoQ with SDS-polyacrylamide gel electrophoresis/electroblot.

The sub-optimal conditions are principally obtained by altering the buffer conditions, and possibly also altering the cleavage temperature (see Example 3 as a possible variant). The nonetheless numerous fragments must each be isolated or enriched by 2 purification steps, it being in principle possible to use any chromatographic and electrophoretic separation techniques. In the case of cyclosporin synthetase fragments from *Tolypocladium niveum*, the combinations of anion exchange chromatography on MonoQ with HP-RPC (Examples 4 and 5) and MonoQ with SDS-polyacrylamide gel electrophoresis/electroblot (Examples 4 and 6) prove particularly advantageous.

The non-ribosomal biosynthetic pathway implies that the sequence of the cyclic peptide is determined by the corresponding arrangement of the amino acid activating domains. Each of these domains must perform analogous reactions, namely the activation of the amino acid by adenylation and binding in the form of a thioester. Hence it may be expected that recurrent, preserved moieties will be found in the protein sequence.

In fact, in previously analysed peptide synthetases, preserved regions within the sequences have been discovered, the number of which coincides with the number of amino acids to be activated: three for ACV synthetase (activates aminoadipic acid, cysteine and valine; Smith et al., 1990, MacCabe et al., 1991, Gutierrez et al., 1991); one each for gramicidine synthetase I (Kraetzschmar et al., 1989) and tyrocidine synthetase I (Weckermann et al., 1988); and four preserved regions in gramicidine synthetase 2, which activates the amino acids proline, valine, ornithine and leucine (Turgay et al., 1992).

Maximally accurate identification and characterisation of such preserved regions of cyclosporin synthetase at both the enzymatic and genetic levels constitutes the basis for well-directed genetic engineering in terms of altering enzyme specificity for the in vivo production of cyclosporin variants. It is therefore useful to identify proteolytic fragments of cyclosporin synthetase which may be correlated with a partial function of the synthetase. The following correlations were made:

(1) a protein fragment with a methyl transferase function (the method on which this work is based is, in principle, applicable to all methyl transferases and is published in Yu et al., 1983; a first application to cyclosporin synthetase is published in Lawen and Zocher 1990); see Example 7;

(2) a protein fragment capable of activating L-alanine (Example 8).

The method used in Example 8 exploits the fact that when proteins are subjected to limited proteolytic cleavage, inter alia intact domains are cleaved which, due to their correct spatial folding, are still capable of exercising their enzyme function to a limited extent. Theoretically, therefore, each amino acid activating domain may be identified with this method. The optimal conditions (for proteolytic cleavage and its timing in relation to amino acid activation) must, however, be determined by testing in each individual case. Moreover, unambiguous identification of a domain may be achieved only if the amino acid it activates occurs only once in the product.

The gene is isolated by DNA hybridisation with oligonucleotides specific to cyclosporin synthetase (Example 10). Whether a specific DNA fragment actually belongs to the cyclosporin synthetase gene is established by Northern hybridisation, since a non-transcribed neighbouring fragment does not hybridise with the corresponding RNA (Example 15). The DNA sequence of the cloned DNA of the cyclosporin synthetase gene is determined and compared with the amino acid partial fragments of cyclosporin synthetase (Examples 13 and 14).

Hence it is possible to transform *Tolypocladium niveum* with the complete gene for cyclosporin synthetase. Among the transformants, strains may be found which contain several copies of this gene or copies with altered regulation. Those strains are selected which, in fermentation tests, display increased cyclosporin formation or can form the same quantity of cyclosporin over a shorter fermentation period.

It is also possible to select the transformed strains by the activity of the cyclosporin synthetase, independently of whether cyclosporin is formed in greater quantities or faster. The isolated cyclosporin synthetase gene can act as an analytical aid in order to determine whether a specific strain of *Tolypocladium niveum* has a high concentration of the mRNA or not (Example 15). Such strains may then be subjected to conventional mutagenesis and strain selection. Even if the initial strain used for transformation is not limited in its cyclosporin synthetase activity, a strain is provided in this way which potentially allows greater cyclosporin formation. The combination of classical genetics (mutation and strain selection) with molecular genetics (transformation with isolated genes) allows the isolation of improved strains which could not be achieved by either of the two methods alone: not by classical genetics because a double mutation is extremely rare in a single selection stage; not by molecular genetics because in some circumstances an unknown factor has a limiting effect.

A further use of the isolated gene is gene-specific mutagenesis. Instead of producing mutations in the entire genome—and therefore also altering many uninvolved genes—the isolated gene alone is mutated using suitable methods (Sambrook et al., 1989) and then transformed to *Tolypocladium niveum* (Example 17). Among the transformants, the proportion of mutants in the cyclosporin synthetase gene is higher than with mutagenesis of the fungus. Mutants, which form specific cyclosporins in greater or reduced quantities, may more frequently be found than with conventional mutagenesis.

By internal sequence comparisons of the derived amino acid sequences (Example 14c) and the correlation of specific partial sequences (Example 8 and Example 9 or Example 14ab), domains of the cyclosporin synthetase for the activation of the individual amino acids may be localised (as performed above for non-ribosomal peptide synthetases). By this means, well-directed mutagenesis of cyclosporin synthetase gene may be performed, by interchanging the gene region of individual domains, by deliberately removing a corresponding region or the cyclosporin synthetase gene may also be extended by individual domains. After transformation of such mutated genes into *Tolypocladium niveum*, new cyclosporin variants may become accessible. The cloned gene may be used to produce strains of *Tolypocladium niveum* which no longer have an active cyclosporin synthetase gene. Such strains may be used for the production of D-alanine or Bmt by fermentation or act as recipient strains for in vitro modified cyclosporin synthetase genes. To this end, an inactive version produced in vitro is constructed for the transformation (Example 18).

When screening for microorganisms which can synthesise cyclosporins, it is necessary that the active metabolites under test conditions are also actually formed in sufficient quantity. Such substances may moreover have slightly changed characteristics and may for this reason alone be overlooked. Example 16 describes the use of the isolated cyclosporin synthetase gene to find microorganisms which contain the cyclosporin synthetase gene in their genome. These genes do not have to be active for this purpose. On the basis of these hybridisations, the corresponding genes may be isolated in a manner analogous to Examples 10, 11 and 12 and transformed into *Tolypocladium niveum*. A strain may be used to this end which no longer contains any active cyclosporin synthetase. This interspecific recombination cannot be achieved with other methods. As described in the preceding paragraph, such strains may be subjected to a screening programme. In this case, genetic variability is based on the introduced gene which hybridises with the cyclosporin synthetase gene.

The control sequences of the cyclosporin synthetase gene may also be used for the construction of plasmids. An example of a control sequence is that which occurs in synp4 (Example 12). The promoter may be fused with a readily detectable reporter gene, such as for example the β-glucuronidase gene (Tada et al., 1991). Strains of *Tolypocladium niveum* which are transformed with these plasmids permit, not only the selection of regulatory mutants, but moreover make it possible to measure and optimise promoter activity independently of other functions.

The following examples and figures illustrate the invention without, however, limiting it.

| Start | End | Fragment Name |
|---|---|---|
| 1 | 2500 | S5 |
| 1300 | 3300 | H2 |
| 2000 | 5400 | E3 |
| 2500 | 5300 | S3 |
| 4700 | 11750 | H3 |
| 5300 | 8400 | S4 |
| 5400 | 7000 | E1 |
| 7000 | 9200 | E2 |
| 9200 | 12100 | E4 |
| 10250 | 13850 | S2 |

Enzyme Restriction sites:

| SalI | 1, | HindIII | 1300, | EcoRI | 2000, |
|---|---|---|---|---|---|
| SalI | 2500, | HindIII | 3300, | HindIII | 3800, |
| HindIII | 4700, | SalI | 5300, | EcoRI | 5400, |
| Ec6RI | 7000, | SalI | 8400, | EcoRI | 9200, |
| SalI | 10250, | HindIII | 11750, | EcoRI | 12100, |
| SalI | 13850. | | | | |

Figure 2:
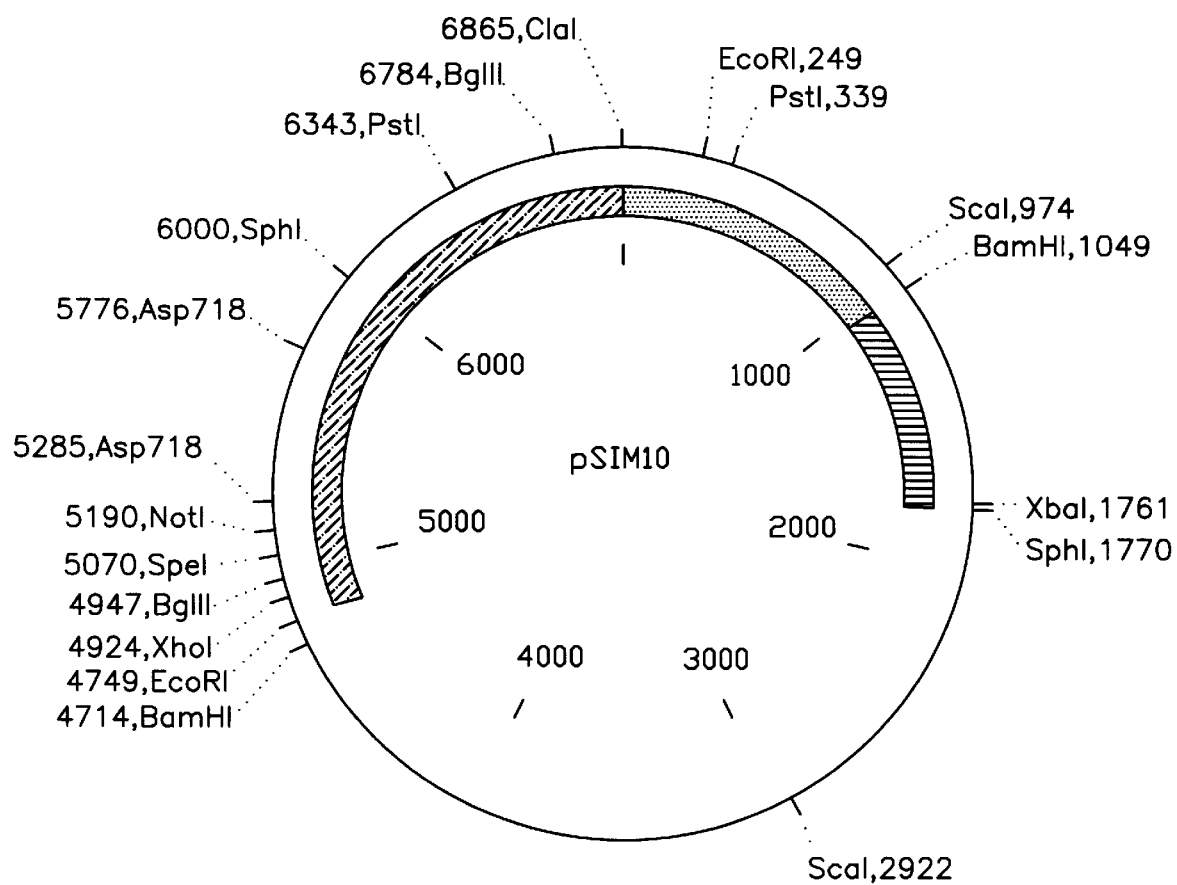

FIG. 2: Restriction map of plasmid pSIM10. The construction and structure of the plasmid is described in Example 18. The positions are stated in bp. Nucleotides 4749–6865 are DNA from *Tolypocladium niveum* containing the promoter of the cyclophilin gene. Nucleotides 1–1761 contain the hygromycin phosphotransferase gene from plasmid pCSN44 (Staben et al., 1989). Nucleotides 1761–4714 are from plasmid pGEM7Zf (Promega Inc.).

Figure 3:
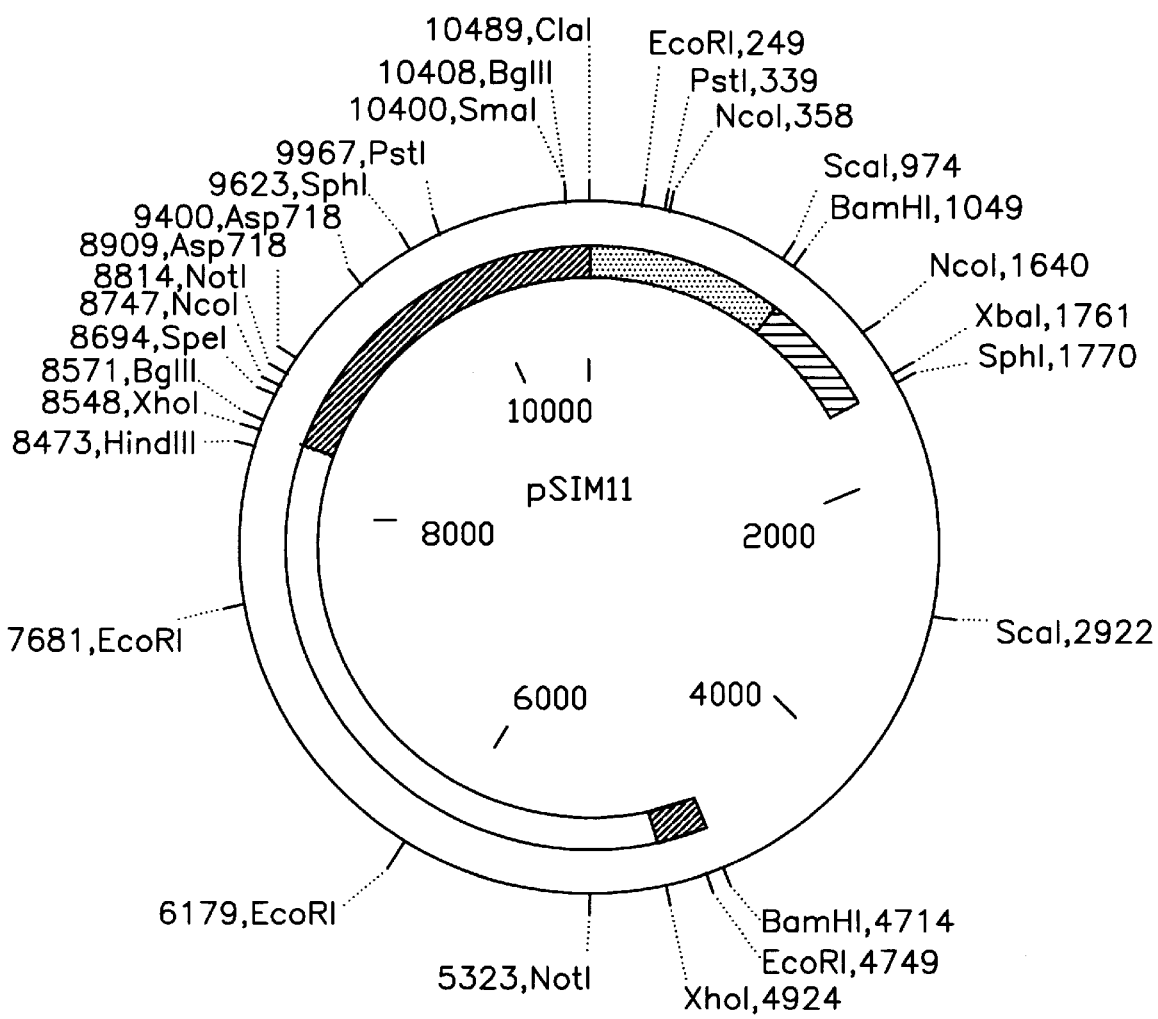

FIG. 3: Restriction map of plasmid pSIM11. Construction of the plasmid is described in Example 18. Nucleotides 4924 to 8553 are the 3.6 kb XhoI restriction fragment from the cyclosporin synthetase gene. Nucleotides 8548–10489 and 1–4929 are plasmid pSIM10 (FIG. 2).

Figure 4:
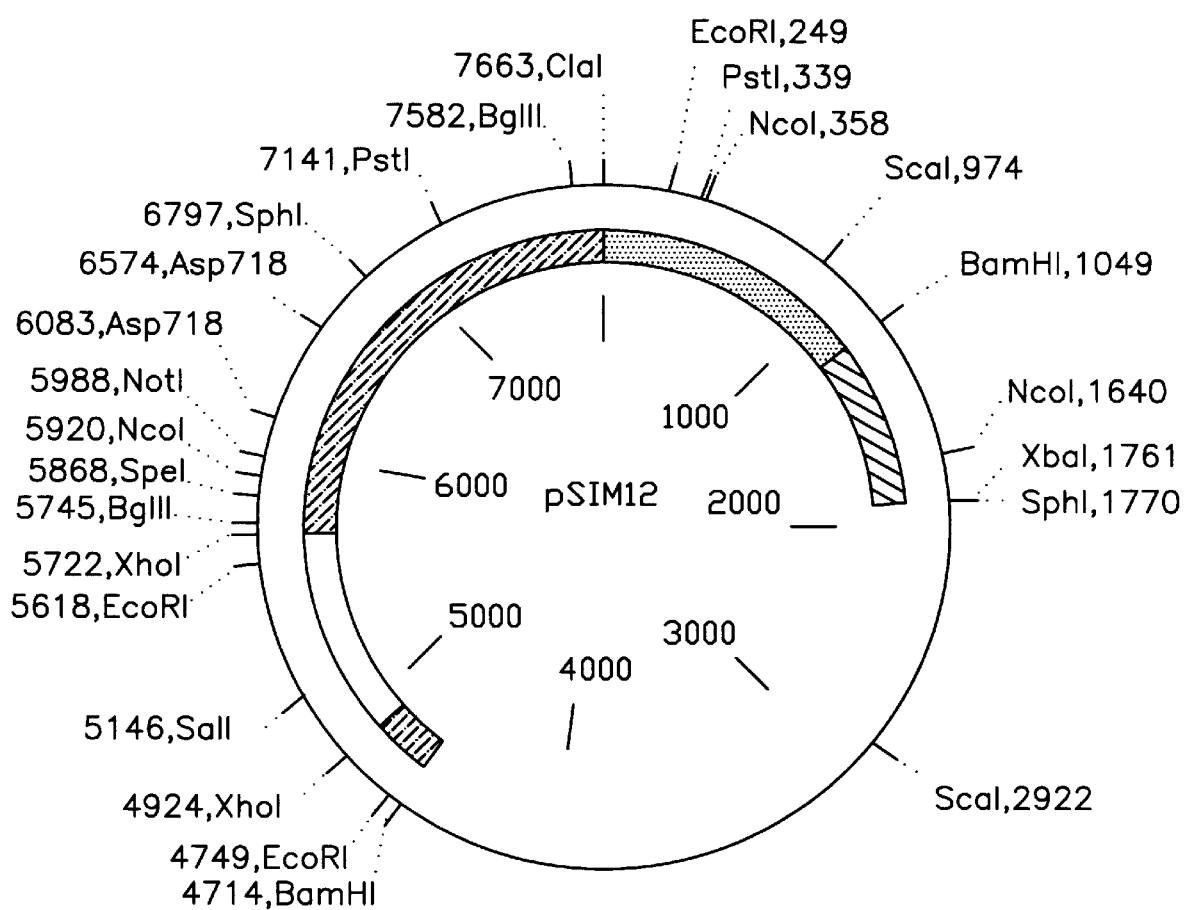

FIG. 4: Restriction map of plasmid pSIM12. Construction of the plasmid is described in Example 18. Nucleotides 4924 to 5727 are the 0.8 kb XhoI restriction fragment from the cyclosporin synthetase gene. Nucleotides 5722–7663 and 1–4929 are plasmid pSIM10 (FIG. 2).

Figure 5:
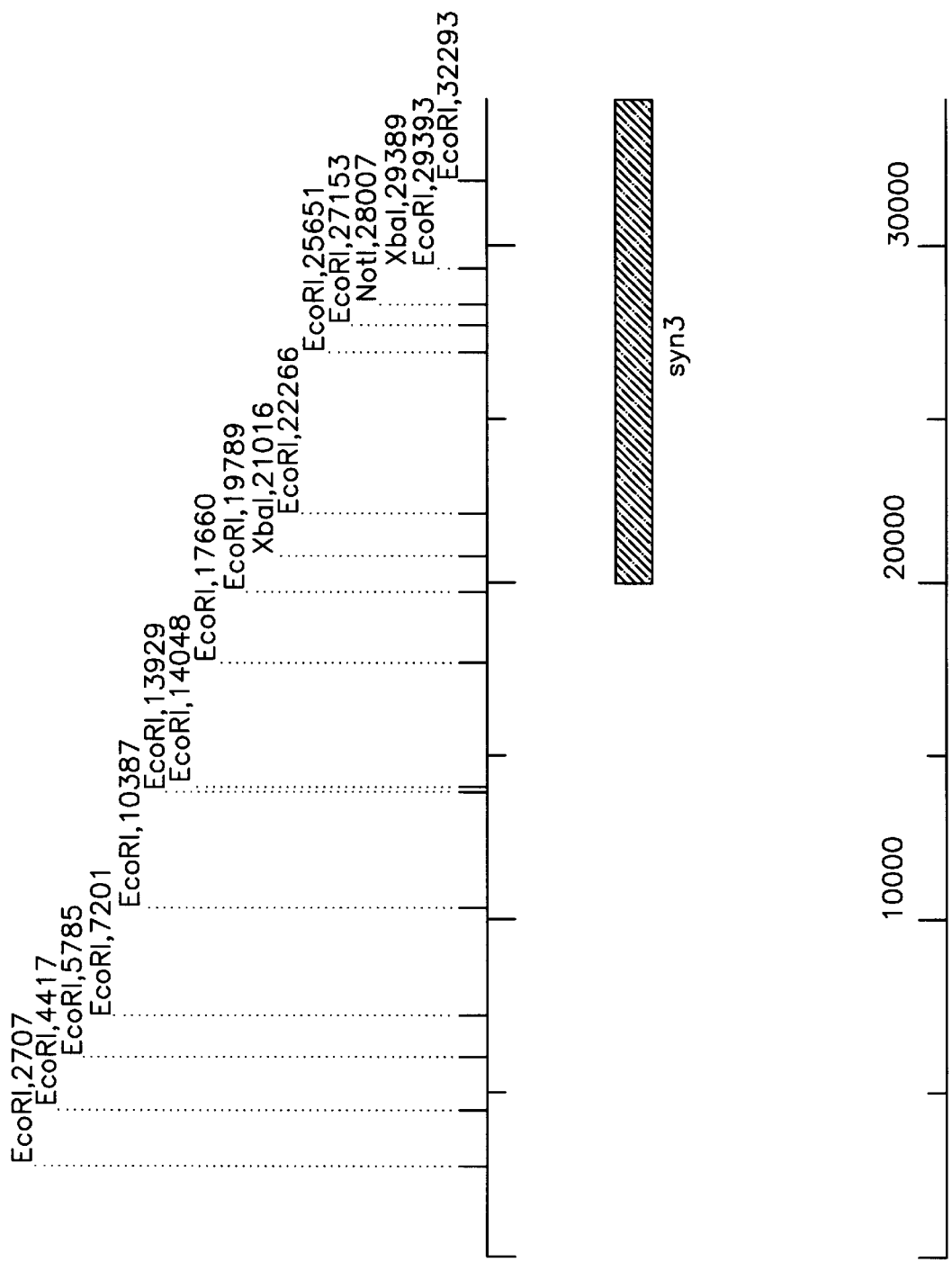

FIG. 5: Restriction map of cyclosporin synthetase gene from *Tolypocladium niveum* cloned in syncos13. The position of some restriction cleavage points is shown. The position of the part cloned in λsyn3 is marked with the crosshatched bar.

All the restriction maps shown in FIGS. 1, 2, 3, 4 and 5 are only approximate reproductions of restriction cleavage points in DNA molecules. The distances as drawn are proportional to the actual distances, but the actual distances may be different. Not all restriction cleavage point are shown, and it is possible for further cleavage points to be present.

EXAMPLE 1

Isolation of Active Cyclosporin Synthetase in Electrophoretically Homogeneous Form The starting material used for the protein purification is *Tolypocladium niveum*, strain 7939/45 (Lawen et al., 1989). All steps are performed at a temperature between 0° and 4° C. 10 g of lyophilised mycelium is finely ground in a mortar with addition of liquid nitrogen and then suspended in buffer A (buffer A: 0.2M HEPES pH 7.8, 0.3M KCl, 4 mM EDTA, 40 (v/v)% glycerol, 10 mM DTT). The suspension is carefully stirred over ice for 1 hour and then centrifuged for 10 min at 10,000 g to remove cell debris.

The supernatant is collected and nucleic acids are precipitated with polyethyleneimine (final concentration 0.1%). The precipitate is removed by centrifugation for 10 min at 10,000 g.

The supernatant is again collected and proteins are precipitated using a solution of ammonium sulphate (saturated) in buffer B (0.1M HEPES pH 7.8, 4 mM EDTA, 15 (v/v)% glycerol, 4 mM DTT) at room temperature. The solution is added dropwise to the supernatant up to a final concentration of 50% of saturation. The mixture is left to stand for a further 30 minutes to reach equilibrium. The precipitated proteins are collected by centrifugation for 30 minutes at 30,000 g. The pellet obtained is resolubilised to 10 ml in buffer B.

The resolubilised pellet is then subjected to molecular sieve chromatography. The molecular sieve is a HW65-F Fractogel obtained from Merck; the column dimensions are 2.6 cm×93 cm, and the volume is 494 ml. The column is operated under fast performance liquid chromatography (FPLC) conditions. The flow rate is 2 ml/min, continuous under buffer B. The cyclosporin synthetase elutes under these conditions at an elution volume of 260 to 310 ml. Processing 10 g of lyophilised mycelium produces 50 mg of cyclosporin synthetase in electrophoretically homogeneous form within 10 hours.

EXAMPLE 2

Detection of Enzymatic Activity of Cyclosporin Synthetase

80 µl of an enzyme sample in buffer B are incubated, in a total volume of 130 µl, with 3.5 mM ATP, 8 mM MgCl$_2$, 10 mM DTT, 10 µM C9 acid, 690 µM of any other constituent amino acid and 100 µM S-adenosyl-methionine+2 µCi of adenosyl-L-methionine-S-[methyl-$^3$H] (75 Ci/mmol) for 1 hour at 22° C. Extraction and detection of the cyclosporin A formed are performed as described in Billich and Zocher 1987.

EXAMPLE 3

Endoproteinase Cleavages

The following endoproteinases (Boehringer Mannheim, sequencing grade) are used: trypsin from bovine pancreas (cleaves after arginine and lysine); LysC from *Lysobacter enzymogenes* (cleaves after lysine); GluC=V8 from *Staphylococcus aureus* (cleaves after glutamic acid and aspartic acid).

The cleavages are not performed under the conditions recommended by the manufacturer; but rather under 'sub-optimal' conditions. The cyclosporin synthetase is incubated in its storage buffer (0.1M HEPES pH 7.5, 4 mM EDTA, 4 mM DTT, 15 (w/v)% glycerol) with protease in a ratio of 100 µg: 1 µg for 2 to 3 hours at 25° C. In this way, fragments of a size up to approximately 200 kDa are produced.

EXAMPLE 4

MonoQ Purification of Fragments

Purification is performed using a commercially available MonoQ column (HR 5/5) obtained from PHARMACIA, at 4° C. The protease digested protein sample is diluted (1:5) in buffer 1 (20 mM HEPES pH 7.5, 2 mM EDTA, 2 mM DTT, 5 w/v % glycerol) and applied to the column. The gradient elution of fragments is carried out in 20 ml of 0% to 100% buffer 2 (buffer 1+500 mM NaCl).

EXAMPLE 5

HP-RPC Purification of MonoQ Fractions

Purification is performed using a commercially available Nucleosil 300A-C4-5 µ column of dimensions 85×4.5 mm. The MonoQ fraction sample is diluted (1:5) in buffer 1 (5% acetonitrile, 0.1% TFA) and applied at a flow rate of 1 ml/min and room temperature. Gradient elution is carried out in 85 minutes from 0% to 100% buffer 2 (90% acetonitrile, 0.1% TFA).

EXAMPLE 6

SDS-PAGE/Blot Purification of MonoQ Fractions

SDS-PAGE is performed according to Lämmli (1970). Thioglycolic acid (2 mM) is added to the electrophoresis buffer in order to prevent the N termini being blocked by residual radicals from the polymerisation reaction. The MonoQ fractions are used after denaturation with SDS for the electrophoresis. For sequencing, the proteins are blotted out of the gel onto glass fibre membranes ("Glassybond" from Biometra) using the semi-dry method.

EXAMPLE 7

Protein Fragment with Methyl Transferase Activity: Identification and Purification The active centre of methyl transferases may be crosslinked with its substrate S-adenosyl-methionine by UV irradiation. This may be exploited by providing a radioactive substrate and so achieving radioactive labelling of the enzyme (Yu et al., 1983). This method, which is also known as "photoaffinity labelling", has been used on cyclosporin synthetase (Lawen and Zocher 1990) and it is possible to show that several labelled protein fragments are produced upon subsequent protease digestion. A labelled fragment is enriched by a combination of the methods described in Examples 4 and 6 and so made accessible to sequencing (see Example 9: aa4). This fragment has a size of approximately 47,000 Dalton.

EXAMPLE 8

Amino Acid Activating Protein Fragments: Identification and Purification

Protein fragments that have the capacity to activate an amino acid are identified by loading the synthetase with radioactively labelled amino acid in the simultaneous presence of an endoproteinase. Approximately 500 µg of purified cyclosporin synthetase are incubated with 25 mM of ATP, 30 mM $MgCl_2$ and 5 µCi of $^{14}$C-L-alanine and are simultaneously treated with, for example, endoproteinase LysC. The reaction is arrested after 3 hours by precipitation of the proteins with TCA. The fragments are resolubilised in a sample buffer for SDS-PAGE, omitting reducing agents. Half of the batch is subjected to SDS-PAGE and the labelled protein fragment is detected by autoradiography of the gel after amplification in "amplify solution" (from NEN) and drying. A fragment with a $M_r$ of approximately 140,000 Dalton is identified and enriched by a combination of the methods described in Examples 4 and 6. The amino acid sequence is given in Example 9: aa13.

EXAMPLE 9

Amino Acid Partial Sequences of Cyclosporin Synthetase

The following partial sequences are obtained from cyclosporin synthetase obtained from Example 6.

aa1: amino acids 1916 to 1942 of Seq Id 2 with amino acid 1921 being S and 1942 being I
aa2: amino acids 2906 to 2925 of Seq Id 2
aa3: amino acids 12240 to 12261 of Seq Id 2 with amino acid 12254 being E.
aa4: amino acids 6535 to 6550 of Seq Id 2
aa5: amino acids 12654 to 12671 of Seq Id 2
aa6: amino acids 1099 to 1117 of Seq Id 2 with amino acids 1116 and 1117 being V and L
aa8: amino acids 1984 to 1996 of Seq Id 2 with amino acid 1991 undeterminable.
aa9: amino acids 13718 to 13738 of Seq Id 2 with amino acid 13731 undeterminable.
aa10: amino acids 9611 to 9622 of Seq Id 2
aa12: amino acids 11475 to 11484 of Seq Id 2
aa13: amino acids 13601 to 13620 of Seq Id 2
aa14: amino acids 9549 to 9568 of Seq Id 2 with amino acid 9565 undeterminable.
aa15: amino acids 9504 to 9521 of Seq Id 2
aa16: amino acids 13569 to 13586 of Seq Id 2 with amino acid 13568 being G
aa17: amino acids 1020 to 1034 of Seq Id 2
aa19: amino acids 9070 to 9084 of Seq Id 2 with amino acids 9082 and 9083 undeterminable
aa20: amino acids 6532 to 6546 of Seq Id 2 with amino acid 6545 undeterminable

EXAMPLE 10

Isolation of λ-Clones which Hybridise with an Oligonucleotide Specific to Cyclosporin Synthetase a) Construction of a genomic λ-gene library from *Tolypocladium niveum*.

DNA is isolated from the mycelium of a culture of *Tolypocladium niveum* grown in medium 1 [50 g/l of maltose, 10 g/l of casein peptone (digested with trypsin, Fluka), 5 g/l of $KH_2PO_4$ and 2.5 g/l of KCl; the pH is adjusted to 5.6 with phosphoric acid]. 4 ml of a spore suspension of *Tolypocladium niveum* strain ATCC 34921 with $4\times10^8$ spores per ml are added to 200 ml of medium 1 in a 1 l conical flask and are shaken for 72 hours at 25° C. and 250 rpm. The mycelium is filtered off with a Büchner funnel, washed with 10 mM of tris-Cl pH 8.0, 1 mM EDTA and ground to a fine powder under liquid nitrogen. Nuclei are isolated from 40 g of moist mycelial mass and are then lysed; the DNA is purified by CsCl-EtBr centrifugation. This method is described in Jofuku and Goldberg (1988). 4.3 mg of DNA are obtained, which, in a 0.5% agarose gel, produces a band exhibiting lower mobility than λ-DNA.

40 µg of the DNA are incubated with 1.4 units of the restriction enzyme Sau3A in 10 mM of tris-Cl pH 7.5, 10 mM $MgCl_2$, 1 mM of DTE, 50 mM of NaCl for 60 minutes at 37° C. and then 10 minutes at 65° C. The extent of cleavage is verified on an agarose gel: part of the DNA is between 10 and 20 kb in size. The DNA is then applied to two NaCl gradients, which are produced by freezing and slowly thawing at 4° C. two Beckman SW28.1 ultracentrifuge microtubes with 20% NaCl in TE (10 mM tris-Cl, pH 8.0, 1 mM EDTA). The microtubes are centrifuged for 16 hours at 14,000 rpm in Beckman L8M ultracentrifuge in rotor SW28.1. The contents of the microtubes are fractionated. Fractions with DNA larger than 10 kb are combined and dialysed against TE. After concentration of the DNA to 500 µg/ml, the DNA is combined with λEMBL3-DNA (Promega Inc.), previously cleaved with EcoRI and BamHI. 1.5 µg of the DNA and 1 µg of λEMBL3-DNA (cleaved with EcoRI and BamHI) are ligated for 16 hours at 16° C. in 5 µl of 30 mM tris-Cl pH 7.5, 10 mM of $MgCl_2$, 10 mM of DTE, and 2.5 mM ATP after the addition of 0.5 U of T4-DNA ligase (DNA concentration 500 µg/ml). The ligation mixture is packaged in vitro with the assistance of protein extracts ("packaging mixes", Amersham). The λ-lysates produced are titrated with *E. coli* KW251 (Promega Inc.). Approximately $4.5\times10^5$ pfu are obtained.

b) Isolation of λ-clones 40,000 recombinant phages from the *Tolypocladium niveum* gene library are cast with *E. coli* strain KW251 onto 90 mm TB plates (TB contains 10 g/l of bacto tryptone and 5 g/l of NaCl and 0.7% of agarose, the pH is adjusted to 7.5 with NaOH). Two blots onto nitrocellulose (Stratagene) are made from each plate (Maniatis et al., 1982). From the amino acid sequence of the cyclosporin synthetase fragment aa9 (Example 9), an oligonucleotide mixture (96 different oligonucleotides, each 20 nucleotides in length) with the sequences

Figure 1:
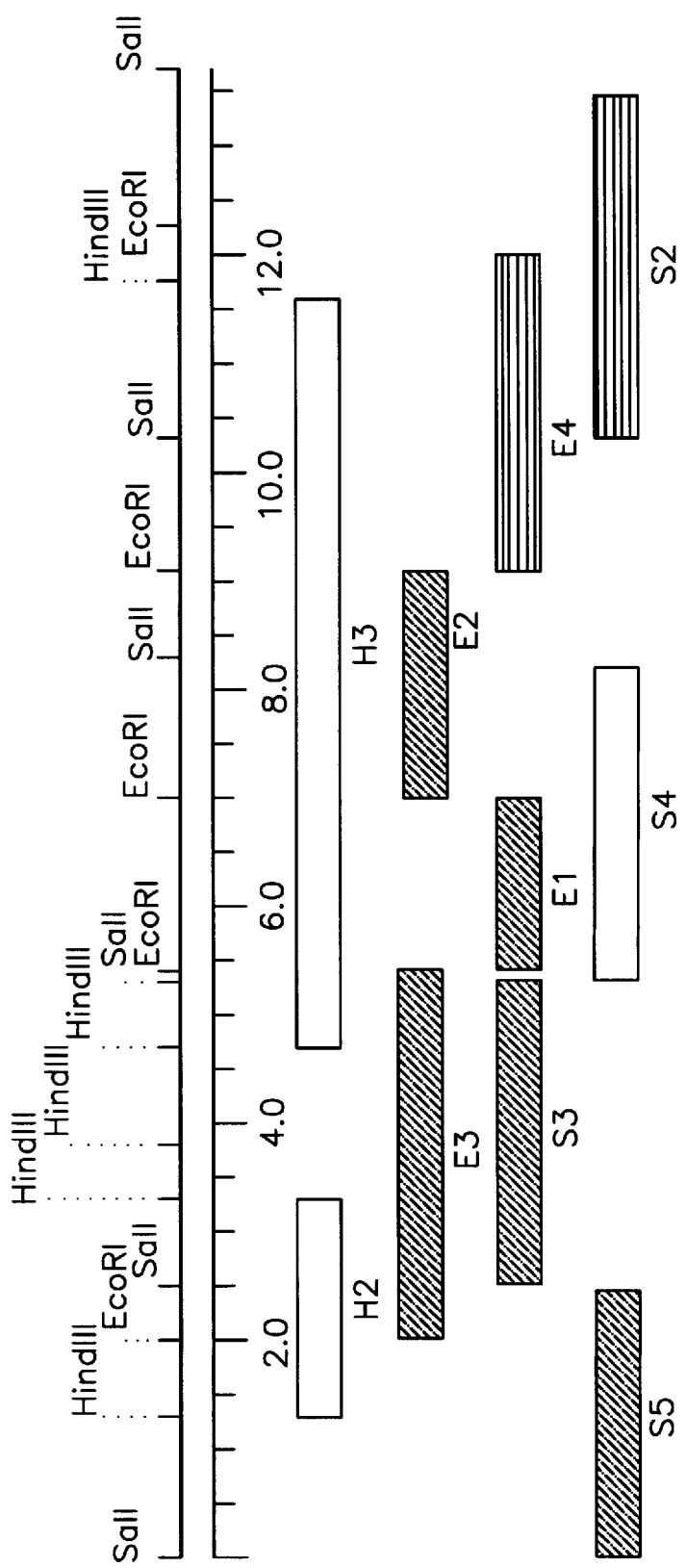
FIG. 1: Restriction map of cyclosporin synthetase gene from *Tolypocladium niveum* cloned in λSYN3. The position of some restriction cleavage points is shown in relation to a scale (2.0, 4.0, 6.0, etc. kb). Among these, several partial fragments subcloned in plasmids are represented as rectangles (S5, E3, S3, etc.). If the corresponding rectangle is filled in, this means that the corresponding DNA fragment reacts with a high molecular weight RNA in Northern hybridisation (S5, E3, S3, E1, E2). Rectangles with lengthwise lines indicate that no bands were obtained in Northern hybridisation (E4, S2). Empty rectangles indicate that the DNA was not used as a probe (S4). The following two tables give the positions of the fragments (S5, H2, etc) and enzyme restriction sites shown in FIG. 1 (in bp)

```
5' GCA TCA ATA TTA AAT TGA TC 3' (SEQ ID NO: 8)
   G   G   G   G   C   G
               T
``` may be produced on the basis of the genetic code. 1.5 µg of this oligonucleotide mixture are incubated in 25 µl of 50 mM tris-Cl pH 9.5, 10 mM $MgCl_2$, 5 mM DTE, 5% glycerol with 150 µCi γ-ATP ($^{32}$P) and 20 U of polynucleotide kinase (Boehringer) for 30 minutes at 37° C. Over 80% of the radioactivity is incorporated. Hybridisation is performed at 37° C. in 400 ml 6×SSPE (Maniatis et al., 1982), 5×Denhardt's solution (Maniatis et al., 1982), 0.1% SDS, 100 µg/ml denatured herring sperm DNA (Maniatis et al., 1982), 0.1 mM ATP, $1.4\times10^6$ cpm/ml $^{32}$P-labelled oligonucleotide mixture for 16 hours. The filters are washed three times for 5 minutes and twice for 30 minutes in 6×SSC (Maniatis et al., 1982) at 4° C. The filters are then washed for 10 minutes at 37° C. in a TMAC (tetramethylammonium chloride) washing solution which is prepared according to Wood et al., 1985. Finally, the filters are washed for 30 minutes at 57° C. in the TMAC washing solution, dried and exposed for 10 days with a Kodak Xomatik AR X-ray film. Regions of the agarose layer corresponding to positive signals on the X-ray film are punched out and resuspended in SM buffer (5.8 g/l NaCl, 2 g/l MgSO$_4$×7 H$_2$O and 50 mM tris-Cl pH 7.5). A suitable dilution is again cast with KW251 onto a TB plate. The plaques are again transferred onto nitrocellulose. The DNA is isolated from plaques producing a positive hybridisation signal in the second hybridisation. The purified DNA from these phages is used for Southern hybridisations and restriction analyses. FIG. 1 shows the restriction map of the *Tolypocladium niveum* proportion of such a λ-clone (=λSYN3). Subcloning is performed in various plasmid vectors (for example pUC18, Pharmacia).

To isolate λ-clones containing the neighbouring DNA fragments ("chromosome walking"), the plaque hybridisation method described above is repeated a number of times; the marginal restriction fragments being used in each case as $^{32}$P-labelled probes. In order to clone the DNA adjoining the region shown schematically in FIG. 1 (λSYN3), fragment S5 is used (FIG. 1). Hybridisation is then performed at 42° C. in 6×SSPE, 50% formamide, 5×Denhardt's solution, 0.1% SDS, 100 μg/ml denatured herring sperm DNA, and 100 μM ATP. Before hybridisation, the $^{32}$P-labelled DNA is heated to 100° C. for 5 minutes and cooled in ice. After 16 to 20 hours, the filters are washed: three times for 10 minutes in 2×SSC, 0.1% SDS and twice for 30 minutes in 0.2×SSC, 0.1% SDS at 65° C. The dried filters are autoradiographed. Those areas of the agarose corresponding to positive signals are further processed as described above.

EXAMPLE 11

Isolation of Cosmid Clones containing Parts of the Cyclosporin Synthetase Gene a) Construction of a genomic cosmid gene library from *Tolypocladium niveum*

Protoplasts are produced as described in Example 17. Approximately 10$^9$ protoplasts are carefully lysed in 2 ml of TE (10 mM tris-HCl, 1 mM EDTA, pH 8.0). 0.1 mg/ml of RNase A are added and incubation is continued for 20 minutes at 37° C. After the addition of 0.5% SDS and 0.1 mg/ml of proteinase K, incubation is continued for a further 40 minutes at 55° C. The batch is very carefully extracted twice with each of TE-saturated phenol, phenol/chloroform (1:1) and chloroform/isoamyl alcohol (24:1) (Maniatis et al., 1982). The aqueous, slightly viscous supernatant is combined with one tenth its volume of 3M sodium acetate (pH 5.2) and covered with a layer of 2.5 times its volume of absolute ethanol at −20° C. and the DNA, found as fine threads at the phase interface, wound up using glass rods. The DNA is dissolved in 3 ml of TE for at least 20 hours. Depending on the quality of the protoplasts, approximately 500 μg/ml of DNA are obtained. Analysis with field inversion gel electrophoresis (FIGE) (0.8% agarose, 0.5×TBE (Maniatis et al., 1982), 6 V/cm, forwards pulse 0.2 to 3 sec, pulse ratio 3.0, running time 5 hours) gives a size greater than 150 kb. Two batches of 135 μg of DNA are cleaved with 7.5 and 15 units; respectively of restriction enzyme NdeII (from Boehringer Mannheim) for 1 hour at 37° C. in 1 ml of buffer (tris-acetate 33 mM, magnesium acetate 10 mM, potassium acetate 66 mM, DTT 0.5 mM, pH 7.9). Aliquots of the cleaved DNA are tested with FIGE and give a maximum size for the fragments obtained of approximately 45 and 30 kb respectively.

Using a gradient mixer, linear NaCl density gradients from 30% to 5% in 3 mM EDTA pH 8.0 are produced in ultracentrifuge microtubes and the DNA fragments applied. After centrifugation for 5 hours at 37,000 rpm and 25° C. (Beckman L7–65 ultracentrifuge, rotor SW 41), the gradient is harvested in 500 μl fractions. Fractions with DNA greater than 30 kb and less than 50 kb are dialysed three times for two hours against TE (tris-HCl 10 mM, EDTA 1 mM, pH 8.0), precipitated with ethanol and each dissolved in 50 μl TE.

sCos1 (from Stratagene) is used as the cloning vector. The vector arms cleaved with BamHI and Xbal are produced and modified as stated by Evans et al., (1989). 1 μg of the cleaved vector are ligated with approximately 500 ng of the DNA fragments in 20 μl of ligation mix (tris-HCl 66 mM, MgCl$_2$ 5 mM, DTE 1 mM, ATP 1 mM, pH 7.5) with 16 units of T4-DNA ligase (from Boehringer) for 16 hours at 12° C. 4 μl portions of the batch are packaged into lambda phage heads with packaging extracts (Gigapak, from Stratagene). *E. coli* SRB (from Stratagene) is used as the host strain for the infection and the bacteriophage lambda-competent cells are produced following the method of Sambrook et al., (1989). After infection, the batches are plated in aliquots onto LB medium (Maniatis et al., 1982) with 75 μg/ml of ampicillin. Recombinant clones are discernible as colonies after 20 hours at 37° C. In total, approximately 50,000 colonies are obtained, which are then suspended in 0.9% NaCl/20% glycerol and stored at −70° C. Analysis of 40 randomly selected clones by isolation and restriction of the cosmids obtained shows that all the clones contain recombinant cosmids; the average insert size is 36 kb.

b) Isolation of cosmid clones

The cosmid gene library is plated at a density of approximately 2500 colonies per 85 mm plate on LB medium with 75 μg/ml of ampicillin (Maniatis et al., 1982). Transfer of each onto two nylon membranes (Duralon UV, Stratagene) is performed as described in Sambrook et al., (1989). The 1.6 kb HindIII fragment from λsyn3 (see FIG. 1) is labelled with alpha-$^{32}$P-dATP using "Random Primin g" (from Stratagene) and is used as a hybridisation probe. Prehybridisation is performed for 6 hours, hybridisation for 18 hours at 42° C. in 5×SSC, 40% formamide, 5×Denhardt's (Maniatis et al., 1982), 0.1% SDS, 25 mM NaH$_2$PO$_4$, pH 6.5, and 250 μg/ml of herring sperm DNA. The filters are washed twice for 10 minutes in 2×SSC/0.1% SDS at room temperature and twice for 40 minutes in 1×SSC/0.1% SDS at 60° C. The membranes are exposed for 14 hours on X-ray film (Kodak Xomatic AR). Colonies having positive signals are purified, the corresponding cosmid-DNA isolated from the colonies and characterised by various restriction analyses and hybridisations with the labelled λsyn3 probes, and the vector-DNA sCos1. FIG. 5 shows the restriction map of the cloned regions of such a cosmid, syncos13; the *Tolypocladium niveum* DNA contained in it amounts to approximately 35 kb and also includes the region of λsyn3.

EXAMPLE 12

Isolation of a P1 Clone with the Complete Gene for Cyclosporin Synthetase

Protoplasts are produced from *Tolypocladium niveum* as described in Example 17 and suspended at a density of 10$^9$/ml in TPS. 1 ml portions of this suspension are mixed with 1 ml of 1.6% melted agarose (Incert from FMC) held at 40° C. and cast into small 1.5 mm thick blocks using a casting stand (BioRad). After solidifying, the blocks are transferred into lysis buffer (0.45M EDTA pH 8.0, 1% N-lauroylsarcosine, 1 mg/ml proteinase K) and incubated for 16 hours at 55° C. The blocks are washed for thrice for 2 hours in 0.5M EDTA pH 8.0 while being slowly rocked and are then stored at 4° C. Before being cleaved, the blocks are cut into small strips, transferred into Eppendorf microtubes and washed for four times for 2 hours and once for 16 hours in TE. The blocks are preincubated in four parallel batches at 4° C., each in 300 μl BamHI buffer (from NEB), supplemented with 100 μg/ml of bovine serum albumin (from NEB) and 80 μM S-adenosylmethionine, for 3 hours on ice. Then, 2 units of BamHI (from NEB) and 16, 20, 24 or 28 units of BamHI methylase (from NEB) are added to each batch and incubation is continued for a further 90 minutes on ice and then for 1 hour at 37° C. The reactions are arrested by the addition of 20 mM of EDTA and 0.5 mg/ml of proteinase K and incubated at 37° C. for 30 minutes.

The blocks are applied to a 1% agarose gel (Seaplaque GTG from FMC) and the DNA fragments separated by pulsed field gel electrophoresis ((Chef DR II from BioRad), 0.5×TBE (Maniatis et al., 1982), switch interval of 8–16 sec, 150 V, 16 h, 12° C.).

The region of DNA fragments between 70 and 100 kb is cut out of the gel and the agarose hydrolysed with β-agarase (from NEB). The DNA solution obtained in this manner is very carefully extracted once with tris-saturated phenol and once with chloroform/isoamyl alcohol (24+1) and then concentrated to a final volume of approximately 100 μl by extraction with 1-butanol. pNS528tet14-Ad10-SacIIB (from DuPont-NEN) is used as the cloning vector. The vector arms are prepared as stated in Pierce et al., (1992). Approximately 250 ng of the cleaved vector are ligated with approximately 500 ng of the DNA fraction for 16 hours at 16° C. (performed as in Example 11, total volume 15 μl). After heating the ligation to 70° C. for 10 minutes, 4 μl aliquots are cleaved with pacase (from DuPont-NEN) and packaged into bacteriophage P1 envelopes by addition of the "head/tail" extract, as described in Pierce and Stemberg (1991). After infection of *E. coli* NS3529, the preparation is plated onto LB medium (Maniatis et al., 1982) with 25 μg/ml kanamycin and 5% saccharose. Recombinant clones become visible after incubation of the plates at 37° C. for 20 h.

In total, approximately 2000 colonies are obtained, which are stored as a pool in 0.9% NaCl/20% glycerol at −70° C. as "P1 library".

The gene library (10×500 colonies) is screened as described in Example 11 (cosmid clones). Inter alia, a positive clone is obtained which contains all the fragments of the cosmid clone syncos13, together with additionally a further approximately 30 kb of the cyclosporin synthetase gene in the 5' direction. Hybridisation with oligonucleotide mixtures derived from suitable amino acid sequences (see Example 9 and Example 10) shows that all the tested sequences are present on this P1 clone (synp4). In this way, it is ensured that the complete gene for cyclosporin synthetase is contained on this clone synp4.

EXAMPLE 13

DNA Partial Sequence of the Cyclosporin Synthetase Gene from *Tolypocladium Niveum* ATCC34921 a) The DNA cloned as described in Examples 11 and 12 is sequenced and is illustrated as SEQ ID NO:1.

b) A polypeptide with the amino acid sequence illustrated as SEQ ID NO:2 is be derived from this DNA.

EXAMPLE 14

Comparison of the Amino Acid Sequences Derived from the DNA with the Cyclosporin Synthetase Amino Acid Partial Sequences The DNA of SEQ ID NO:1 is translated on the basis of the genetic code into an amino acid sequence (i.e. position 1 of the protein sequence corresponds to position 885 of the DNA sequence) and is compared with the amino acid sequences given in Example 9:

AA-Partial sequence 3: in SEQ ID NO:2, position 12254 is T. Otherwise all amino acids correspond.
AA-Partial sequence 4: all amino acids correspond.
AA-Partial sequence 5: all amino acids correspond.
AA-Partial sequence 9: in SEQ ID NO:2, position 13730 is W. Otherwise all amino acids correspond. (Position 13 of the AA partial sequence aa9 could not be determined.)
AA-Partial sequence 10: all amino acids correspond.
AA-Partial sequence 12: all amino acids correspond.
AA-Partial sequence 13: all amino acids correspond.
AA-Partial sequence 14: in SEQ ID NO:2, position 9565 is C. Otherwise all amino acids correspond.
AA-Partial sequence 15: all amino acids correspond.
AA-Partial sequence 16: Position 1 of the AA partial sequence aa16 does not correspond to the AA sequence of SEQ ID NO:2. Otherwise all amino acids correspond.
AA-Partial sequence 19: in SEQ ID NO:2, positions 9082 and 9083 are R and Y. Otherwise all amino acids correspond.
AA-Partial sequence 20: in SEQ ID NO:2, position 6545 is W. Otherwise all amino acids correspond.

Further, internal comparison of the amino acids 13804–14063 of SEQ ID NO:2 with amino acids 12304–12563 of SEQ ID NO:2 shows that 178 out of 259 amino acids are identical (68.7%). A further 28 amino acid residues (10.8%) are functionally similar. In total, 11 partial regions similar to each other may be identified in this manner.

EXAMPLE 15

Isolation of RNA from Mycelium of *Tolypocladium Niveum* and Northern Hybridisation A 1 l conical flask with 100 ml of medium 4 (Dreyfuss et al., 1976) is inoculated with a spore suspension of *Tolypocladium niveum* ATCC34921 ($1 \times 10^7$ spores/ml) and shaken for 96 hours at 250 rpm and 25° C. 1 l conical flasks with 100 ml of medium 5 (Dreyfuss et al., 1976) are inoculated with 10 ml of this preculture and shaken for 7 days at 25° C. and 250 rpm. The cyclosporin A concentration is determined (Dreyfuss et al., 1976) to be 100 μg/ml. 8 g of moist mycelial mass is filtered, washed with TE (10 mM tris-Cl pH 7.5, 1 mM EDTA) and ground to a fine powder in a mortar under liquid nitrogen. RNA is then isolated according to the method described by Cathala et al., (1983). 4 mg of RNA are obtained, which are stored at −70° C. 10 μg of the RNA are separated on a denaturing 1.2% agarose gel containing 0.6M formaldehyde. The electrophoresis buffer is 0.2M MOPS, 50 mM sodium acetate, 10 mM EDTA, pH 7.0. The RNA is dissolved in a buffer mixed together from 0.72 ml formamide, 0.16 ml of 10×concentrated electrophoresis buffer, 0,26 ml formaldehyde, 0.18 ml water and 0.10 ml glycerol. The samples are heated to 100° C. for 2 minutes and separated at 115 V, 100 mA over 2 hours. The gel is shaken three times for 20 minutes in 10×SSC, blotted onto Hybond N-Filter and fixed by UV treatment. Hybridisation is performed at 42° C. in 6×SSPE, 50% formamide, 5×Denhardt's solution, 0.1% SDS, 100 µg/ml denatured herring sperm DNA, and 100 µM ATP. The $^{32}$P-labelled DNA (fragments of the cloned DNAs described in Examples 9 to 12) are heated to 100° C. for 5 minutes and cooled in ice before hybridisation. After 16 to 20 hours, the filters are washed: three times for 10 minutes in 2×SSC, 0.1% SDS and twice for 30 minutes in 0.2×SSC, 0.1% SDS at 65° C. The dried filters are autoradiographed. If the fragment used as the probe is a fragment of the cyclosporin synthetase gene, a band may be detected on the X-ray film after 24 to 72 hours of autoradiography at −70° C. The band exhibits distinctly less mobility than the largest of the comparison RNA used (9500 b; RNA-ladder, BRL). FIG. 1 summarises the results of such hybridisations: in relation to the restriction map of a λ-clone, the isolation of which is described in Example 10, the positions of individual restriction fragments are given which were used as probes in Northern hybridisations. The filled-in rectangles indicate that the bands described above may be detected (E2, E3, E1, S3, S5), while the rectangles with the transverse lines stand for those fragments which do not hybridise with such a band (E4, S2). (Fragment S4 was not used as a probe).

EXAMPLE 16

Identification of Homologous Synthetase Genes 100 ml of medium 1 (Dreyfuss et al., 1976) are inoculated with 1×10$^8$ fungal spores and shaken for 72 hours at 25° C. and 250 rpm. The mycelium is filtered out, washed with TE and lyophilised. 100 mg of lyophilised mycelium are added to 700 µl of lysis buffer (200 mM tris-Cl pH 8.5, 250 mM NaCl, 25 mM EDTA, 0.5% SDS) and 100 mg of aluminium oxide powder (Sigma A2039) in an Eppendorf homogeniser and are homogenised. 500 µl of phenol-chloroform are then added and vigorously mixed in. After 15 minutes centrifugation, the extraction is repeated. A volume of 3M sodium acetate pH 5.2 corresponding to 0.1 time the volume of the supernatant are added to the supernatant and then a volume of i-propanol corresponding to 0.6 time the volume of the supernatant is thoroughly mixed in. After 5 minutes of centrifugation, the pellet is washed with 70% ethanol, briefly dried and dissolved in 100 µl of TE with 100 µg/ml of RNase and incubated for 15 minutes at 37° C. The phenol-chloroform extraction and ethanol precipitation are then repeated. The precipitated DNA is collected.

5 µl portions of the DNA are cleaved with XhoI, separated on an agarose gel and blotted onto a nylon filter. This filters are hybridised with $^{32}$P-labelled λSYN3 DNA as a probe. Hybridisation is performed under standard conditions, as described in Example 10 ("chromosome walking"). The hybridisations may, however, also be performed under less stringent conditions.

The following hybridising bands are obtained with DNA from *Tolypocladium niveum* (all data are estimates due to mobility in the gel): 3.6 kb, 3.4 kb, 3.2 kb, 3.0 kb, 2.3 kb, 1.9 kb and 0.7 kb. DNA from *Fusarium solani* ATCC 46829 also displays bands at 3.6 kb, 3.4 kb, 1.9 kb and 0.7 kb together with a further band at approximately 2.1 kb. DNA from *Neocosmospora vasinfecta* ATCC 24402 also displays the bands at 3.6 kb, 3.4 kb, 1.9 kb and 0.7 kb, together with two further bands at 2.9 kb and 1.8 kb. DNA from *Tolypocladium geodes*, Acremonium sp. S42160/F, Paecilomyces sp. S84-21622/F, Verticillium sp. 85-22022/F (Dreyfuss, 1986) each display several hybridising bands in the range 0.7 kb to 7 kb.

On the basis of the DNA sequence SEQ ID NO:1, the following oligonucleotide probes may be synthesised:

Nucleotides 35073–35092 of SEQ ID NO:1

Nucleotides 37848–37829 of SEQ ID NO:1 (complementary strand)

or also

Nucleotides 40309–40328 of SEQ ID NO:1

Nucleotides 42018–41999 of SEQ ID NO:1 (complementary strand)

If 50 ng of the *Tolypocladium geodes* CBS723.70 DNA is amplified with the first of the two oligonucleotide pairs described above (Sambrook et al., 1989): 30 cycles: 1 min 30 sec 94° C.; 2 min 30 sec 50° C.; 6 minutes 72° C., a 350 bp DNA is produced. If a part of this DNA is sequenced, the sequence given as SEQ ID NO:3 is obtained. This DNA sequence is 75.1% homologous to the corresponding DNA sequence of Seq Id 1.

Also, if 50 ng of the *Neocosmospora vasinfecta* ATCC 24402 DNA is amplified with the second of the two oligonucleotide pairs described above (Sambrook et al., 1989): 30 cycles: 1 minutes 30 sec 94° C.; 2 min 30 sec 50° C.; 6 minutes 72° C., a 1713 bp DNA is produced. If this DNA is sequenced, the sequence given as SEQ ID NO:4 is obtained. This DNA sequence is 96.3% homologous to the corresponding DNA sequence of SEQ ID NO:1.

EXAMPLE 17

Protoplastisation and Transformation of *Tolypocladium Niveum* a) Method 1:

200 ml of medium 1 (maltose (monohydrate) 50 g/l, casein peptone, digested with trypsin (Fluka 70169) 10 g/l, KH$_2$PO$_4$ 5 g/l, KCl 2.5 g/l pH 5.6) in a conical flask are inoculated with 10$^9$ spores of *Tolypocladium niveum* and are incubated at 27° C., 250 rpm for approximately 70 hours. 200 µl of (0.1%) β-mercaptoethanol are added and incubation is continued for a further 16 hours. The mycelium is harvested by centrifugation (Beckman J2–21 centrifuge, rotor JA14, 8000 rpm, 20° C., 5 minutes), washed in 40 ml of TPS (NaCl 0.6M, KH$_2$PO$_4$/NaH$_2$PO$_4$ 66 mM pH 6.2) and the pellet volume measured by centrifugation in calibrated microtubes at 2000 g (in Beckman GPR centrifuge, GH3.7 rotor, 3000 rpm, 5 minutes). The mycelium is suspended in TPS (3 ml of TPS are used for each 1 ml of pellet volume) and the same volume of protoplastisation solution is added (Novozym 234 10 mg/ml from Novo Industri, batch PPM-2415), cytohelicase 5 mg/ml (from IBF), Zymolyase 20T 1 mg/ml (from Seikagaku Kogyo, batch no. 120491). The suspension is incubated at 27° C. at 80 rpm for approximately 60 minutes. The protoplasts are filtered through a milk filter, centrifuged out (700 g, 10 minutes) and taken up in a total of 4 ml of TPS. Each 1 ml of this suspension is layered on to 4 ml of 35% saccharose solution and is centrifuged at 600 g, 20° C. for 20 minutes. The protoplast bands at the phase interface are drawn off, each diluted to 10 ml with TPS, centrifuged out, carefully resuspended in 200 µl portions of TPS and the suspensions are combined. For each 1 ml of pellet volume of starting mycelium (see above), approximately 2×10$^8$ protoplasts are obtained.

The protoplast suspension is centrifuged out (700 g, 10 minutes) and suspended in 1M sorbitol, 50 mM CaCl$_2$ at a density of 1×10$^8$. 90 µl portions of this suspension are combined with 10 µl of the vector DNA to be transformed, which contains the amdS gene from *Aspergillus nidulans*, for example plasmid p3SR2 (Hynes et al., 1983), (1–10 µg dissolved in tris-HCl 10 mM, EDTA 1 mM, pH 8.0) and 25

μl of PEG 6000-Lsg are added (25% PEG 6000, 50 mM CaCl$_2$, 10 mM tris-HCl, pH 7.5, freshly prepared from the stock solutions: 60% PEG 6000 (from BDH), 250 mM tris-HCl pH 7.5, 250 mM CaCl$_2$). The transformation batch is placed on ice for 20 minutes and then a further 500 μl of the mixed, PEG 6000 solution are added and carefully mixed in. After 5 minutes at room temperature, 1 ml of 0.9M NaCl, 50 mM CaCl$_2$ is added, the entire batch added to 7 ml of melted soft agar TMMAAC+N, held at 45° C., and cast onto preheated TMMAAC+N plates. Medium TMMAAC+N contains 6 g/l glucose, 3 g/l KH$_2$PO$_4$, 0.5 g/l KCl, 0.4 g/l MgSO$_4$×7 H$_2$O, 0.2 g/l CaCl$_2$×2 H$_2$O, 8 mM acrylamide, 2.1 g/l CsCl, 1 ml/l trace element solution, and 0.6M NaCl. 15 g/l of Agar-Agar (Merck) are used for plates and 7 g/l for soft agar. The trace element solution contains 1 mg/ml of FeSO$_4$×7 H$_2$O, 9 mg/ml of ZnSO$_4$×7 H$_2$O, 0.4 mg/ml of CuSO$_4$×5 H$_2$O, 0.1 mg/ml of MnSO$_4$×H2O, 0.1 mg/ml of H$_3$BO$_3$ and 0.1 mg/ml of Na$_2$MoO$_4$×H$_2$O. Transformants are capable of using acrylamide as a source of nitrogen in the medium and may therefore be identified after approximately 3 weeks at 25° C. as colonies against weak background growth.

b) Method 2:

Two portions each of 4.0 ml of the *Tolypocladium niveum* spores (ATCC 34921; 5×10$^8$/ml) are introduced into a 1 l conical flask with 200 ml of medium 1 (50 g/l maltose (monohydrate), 10 g/l casein peptone, digested with trypsin, FLUKA 70169, 5 g/l KH$_2$PO$_4$, 2.5 g/l KCl, pH 5.6) and are shaken at 25° C. at 250 rpm for 65 hours. The mycelium is filtered out over a sterile sintered porcelain filter with GMX nylon gauze and washed with TE (10 mM tris-Cl pH 7.5, 1 mM EDTA) and resuspended in 40 ml of YG (5 g/l yeast extract, 20 g/l dextrose). Centrifugation is carried out at 900 g and 20° C. for 5 minutes. The pellet is resuspended in YG (approximately 1 ml pellet in 5 ml) and 5 ml of protoplastisation solution are added to 5 ml of suspension. The protoplastisation solution is produced from a solution containing 1.1M KCl and 0.1M citric acid. The pH is adjusted to 5.8 with KOH. Driselase (Sigma D9515) is added (15 mg/ml; storage at −20° C.); the suspension remains in the ice for 15 minutes and the starch carrier is removed by centrifugation for 5 minutes at 2000 rpm. Novozym (4 mg/ml) and bovine serum albumin (Sigma A7096, 20 mg/ml) are added. The solution is filtered through Millipore SLGV025LS and remains in the ice until used. The preparation is shaken at 37° C. for 2.5 hours at 250 rpm. The preparation is filtered through a milk filter. The protoplasts are centrifuged out (700 g; 20° C.; 5 minutes) and carefully resuspended in STC (1.2M sorbitol, 50 mM CaCl$_2$, 10 mM tris-HCl pH 7.5). 5 ml of 35% saccharose solution are carefully covered with a layer of the suspension and centrifuged (600 g; 20° C.; 20 minutes). The bands are drawn off and diluted to approximately 5 ml with STC. 2×10$^8$ protoplasts are obtained from 200 ml of culture.

50 μl of the protoplast suspension (1×10$^8$/ml) are introduced into a sterile Eppendorf tube and 5 μg of plasmid DNA in TE and 12.5 μl of PEG solution (20% PEG 4000, 50 mM CaCl$_2$, 10 mM tris-HCl pH 7.5) are added. This solution is mixed from separately autoclaved stock solutions: 1M CaCl$_2$, 1M tris-HCl pH 7.5, 60% PEG 4000 (Riedel de Haën). Once the mixture has stood for 20 minutes in ice, 0.5 ml of PEG solution are added and carefully mixed in. After 5 minutes at room temperature, 1 ml of 0.9M NaCl, 50 mM CaCl$_2$ are carefully mixed in. The suspension is added to 10 ml of TM88 sorbitol soft agar (20 g/l malt extract, 4 g/l yeast extract, 10 g/l bacto agar, 218 g/l sorbitol, pH 5.7) (45° C.) and cast onto TM88 sorbitol plates (10 ml TM88 sorbitol agar: 20 g/l malt extract, 4 g/l yeast extract, 30 g/l bacto agar, 218 g/l sorbitol, pH 5.7). After 15 to 20 hours at 25° C., 10 ml of TM88 sorbitol agar with 600 μg/ml of hygromycin (45° C.) are poured over. Hygromycin resistant transformants may be detected after 7 days at 25° C.

EXAMPLE 18

Construction of Vectors pSIM10, pSIM11 and pSIM12 and Transformation with these Plasmids a) Isolation of cyclophilin gene from *Tolypocladium niveum*

As described in Example 10, the *Tolypocladium niveum* gene library is screened with a radioactively labelled DNA probe. Hybridisation is performed at 42° C. in 6×SSPE, 30% formamide, 5×Denhardt's solution, 0.1% SDS, 100 μg/ml denatured herring sperm DNA, and 100 μM ATP. $^{32}$P-labelled DNA (fragments of the DNA of the cyclophilin gene from *Neurospora crassa*, Tropschug et al., 1988) are heated to 100° C. for 5 minutes and cooled in ice before hybridisation. After 16 to 20 hours, the filters are washed three times for 10 minutes in 2×SSC, 0.1% SDS and twice for 30 minutes in 1×SSC, 0.1% SDS at 45° C. The dried filters are autoradiographed. The purified DNA from λ-phages is subcloned in plasmids and characterised by restriction mapping, Southern hybridisation and DNA sequencing. The cDNA sequence of SEQ ID NO:5 is obtained. The sequence is homologous to the cyclophilin gene of *N. crassa*. The start codon ATG is at positions 12–14 and the stop codon TAA is at positions 552–554.

b) Construction of vector pSIM10 and transformation with this plasmid

On the basis of the SEQ ID NO:5, a first oligonucleotide is synthesised which is largely complementary to SEQ ID NO:5 (positions 2 to 29); however, the ATG region (12 to 14) is altered in such a way that a ClaI cleavage point (ATCGAT) is produced. A second oligonucleotide contains a sequence of the plasmid pUC18 and a recognition sequence for BamHI and is given as Seq Id 6.

A plasmid containing a 2.7 kb EcoRI-HindIII fragment from Example 18a cloned into pUC18 is linearised with HindIII. 1 ng of the plasmid DNA is amplified with the oligonucleotides described above (Sambrook et al., 1989): 30 cycles: 1 minutes 30 sec 94° C.; 2 min 30 sec 50° C.; 6 min 72° C. A 2.1 kb DNA is produced. After chloroform extraction, this DNA is purified by ultrafiltration (Ultrafree MC 100 000; Millipore) and cleaved in the appropriate buffer with the enzymes ClaI and BamHI. 50 ng of this DNA are ligated with 50 ng of BamHI and ClaI cleaved DNA of the plasmid pGEM7Zf (Promega). The newly produced plasmid is cleaved with ClaI and XbaI and ligated with a ClaI-XbaI restriction fragment 1.76 kb in size from the plasmid pCSN44 (Staben et al., 1989). A restriction map of this plasmid (pSIM10) is reproduced in FIG. 3.

The 2157 bp BamHI-ClaI restriction fragment of the plasmid (4714–6865 in FIG. 3), which contains the cyclophilin gene promoter, has the DNA sequence of SEQ ID NO:7.

The plasmid pSIM10 may be used for the transformation of *Tolypocladium niveum*, as described in Example 17. DNA from the transformants is cleaved with Bars and, after electrophoresis, blotted on a nylon membrane. The 1.8 kb BglII fragment from pSIM10 (FIG. 3) is used as a radioactive probe. In this way, those of the transformants in which the plasmid pSIM10 has been incorporated once or a plurality of times into the genome may be identified.

The XhoI cleavage point in plasmid pSIM10 (4924) allows the construction of plasmids which contain defined parts of the cyclosporin synthetase gene with which a deliberate inactivation of the cyclosporin synthetase gene is possible:

pSIM11 contains a 3.6 kb XhoI restriction fragment (42285–45909 of Seq Id 1). If the plasmid linearised with EcoRV is used for the transformation, approximately 30% of transformants obtained no longer form cyclosporin. It is shown with Southern hybridisations with DNA from such transformants that an 8.4 kb XbaI fragment is no longer detectable, but instead two new restriction fragments with 10.6 kb and 8.2 kb are detected.

pSIM12 contains a 0.8 kb XhoI restriction fragment (39663–40461 of Seq Id 1). If the plasmid linearised with SalI is used for the transformation, approximately 30% of transformants obtained no longer form cyclosporin. It is shown with Southern hybridisations with DNA from such transformants than an 8.4 kb XbaI fragment is no longer detectable, but instead two new restriction fragments with 10.4 kb and 5.6 kb are detected.

EXAMPLE 19

Cotransformation with Synp4 pSIM10 (Example 18) is used as transformation vector. Together with this vector, equimolar quantities of synp4 (Example 12) are also used in the same transformation batch. These cotransformations are performed according to the method described in Example 17 and *Tolypocladium niveum* ATCC 34921 is used as the starting strain.

Genomic DNA from hygromycin resistant transformants is isolated according to a rapid method. To this end, mycelium is taken from an area of approximately 1 cm$^2$ of the corresponding colony and transferred into Eppendorf homogenisers. 1 ml lysis buffer (50 mM EDTA, 0.2% SDS) and 100 mg aluminum oxide (grade A5, from Sigma) are added and thoroughly homogenised for approximately 5 minutes. After centrifugation (5 minutes, 11,000 rpm) the supernatant is extracted once with each of tris-saturated phenol, phenol/chloroform (1:1) and chloroform/isoamyl alcohol (24:1) and the DNA precipitated with isopropanol using the standard procedure (Sambrook et al., 1989).

The DNA is completely restricted with the restriction enzyme SalI, separated with gel electrophoresis and investigated in Southern hybridisations. The 0.8% agarose gel is transferred by vacuum blotting (Vacublot, from Pharmacia) onto a nylon membrane (Duralon-UV from Stratagene) and fixed with UV.

As probe for the hybridisations, the small SpeI restriction fragment from the bacteriophage P1 vector pNS528tet14-Ad10-SacIIB (from DuPont-NEN) is prepared by gel electrophoresis and Geneclean II Kit (from BIO101) and radioactively labelled with alpha $^{32}$P dATP by "random primer" synthesis (from Stratagene).

Prehybridisation is performed for approximately 8 to 16 hours at 42° C. in 6×SSC, 50% formamide, 5×Denhardt's (Maniatis et al., 1982), 0.1% SDS, 0.25 mg/ml denatured herring sperm DNA, and 25 mM NaH$_2$PO$_4$ pH 6.5 in a volume of 10 ml per 100 cm$^2$ of membrane. After addition of the labelled probe, incubation is continued for a further 16 to 20 hours at 42° C. The blot is washed twice for 10 minutes with 2×SSC/0.1% SDS at 25° C. and twice for 30 minutes with 0.5×SSC/0.1% SDS at 60° C. After autoradiography for approximately 48 to 96 hours at −70° C. with Kodak intensifying film onto X-ray film (Xomatic AR, from Kodak), bands become visible on the X-ray film.

Some of the investigated DNAs display hybridisation signals which are attributable to the integration of synp4. The number of signals, which should correlate with the number of integrated synp4 molecules, varies between 1 and 3.

A transformant strain verified in this manner is investigated for cyclosporin A formation by test fermentation in a shaking flask as described by Dreyfuss et al. (1976). Whilst approximately 100 μg/ml of cyclosporin A is formed in parallel tests of the untransformed starting strain *Tolypocladium niveum* ATCC 34921, approximately 150 μg/ml of cyclosporin A is detected in tests with the strain in which additional copies of the cyclosporin synthetase gene are present due to the integration of synp4.

| Abbreviations used: | |
|---|---|
| ACV | aminoadipyl-cysteinyl-valine |
| amdS | acetamidase gene |
| ATCC | American Type Culture Collection |
| ATP | adenosine triphosphate |
| bp | base pairs |
| CBS | Centraalbureau voor Schimmelcultures |
| DTE | dithioerythritol |
| DTT | dithiothreitol |
| EDTA | ethylenediaminetetraacetic acid |
| HEPES | N-2-hydroxyethyl-puperazine-N-2-propanesulphonic acid |
| MOPS | 3-morpholinepropanesulphonic acid |
| PEG | polyethylene glycol |
| pfu | plaque forming units |
| SDS | sodium dodecyl sulphate |
| SDS-PAGE | SDS-polyacrylamide gel electrophoresis |
| SSC | 150 mM NaCl, 15 mM sodium citrate, pH 7.0 |
| SSPE | 180 mM NaCl, 10 mM sodium phosphate, 1 mM EDTA, pH 7.7 |
| TE | 10 mM tris-Cl pH 7.5, 1 mM EDTA |
| TFA | trifluoroacetic acid |
| tris | tris(hydroxymethyl)aminomethane |
| YAC | yeast artificial chromosome |

Moreover, the customary abbreviations for the restriction endonucleases are used (Sau3A, HindIII, EcoRI, HindIII, ClaI etc.; Maniatis et al., 1982). The nucleotide abbreviations A, T, C, G are used for DNA sequences and the amino acid abbreviations (Arg, Asn, Asp, Cys etc.; or R, N, D, C etc.) for polypeptides (Sambroock et al., 1989).

Literature List

A. Billich and R. Zocher (1987) Enzymatic Synthesis of Cyclosporin A *J. Biol. Chem.* 262, 36, 17258–17259

J. F. Borel, C. Feurer and H. U. Gubler (1976) Biological effects of cyclosporin A: a new antilymphotic agent *Agents Actions* 6: 468

M. Dreyfuss, E. Härri, H. Hofmann, H. Kobel, W. Pache and H. Tscherter (1976) Cyclosporin A and C *European J. Appl. Microbiology* 3 (1976), S. 125–133.

M. M. Dreyfuss (1986) Neue Erkentnisse aus einem pharmakologischen Pilz-Screening, Sydowia 39 (1986), S. 22–36.

K. D. Jofuku and R. B. Goldberg, *Analysis of plant gene structure*, in: *Plant molecular biology: a practical approach* (C. H. Shaw, Hrsg.), 1. Aufl., IRL press, Oxford 1988, S. 37–66.

H. Kleinkauf and H. v. Döhren (1990) Nonribosomal biosynthesis of peptide antibiotics *Eur. J. Biochem.* 192, 1–15

J. Kraetzschmar, M. Krause and M. A. Marahiel (1989) Gramicidin S Biosynthesis Operon Containing the Structural Genes grsA and grsB has an Open Reading Frame Encoding a Protein Homologous to Fatty Acid Thioesterases *J. Bacteriol.* 171, 5422–5429

U. K. Laemmli (1970) Cleavage of structural proteins during the assembly of the head of bacteriophage T4 *Nature* 227, 680–685

A. Lawen, R. Traber, D. Geyl, R. Zocher and H. Kleinkauf (1989) Cell-Free Biosynthesis of New Cyclosporins *J. Antibiotics* 42, 8, 1283–1289

A. Lawen, J. Dittmann, B. Schmidt, D. Riesner and H. Kleinkauf (1992) Enzymatic biosynthesis of cyclosporin A and analogues *Biochimie* 74, 511–516

A. Lawen and R. Zocher (1990) Cyclosporin Synthetase. The Most Complex Peptide Synthesizing Multienzyme Polypeptide So Far Described *J. Biol. Chem.* 265, 19, 11355–11360

A. P. McCabe, H. v. Liempt, H. Palissa, M. B. R. Riach, E. Pfeifer, H. v. Döhren and J. R. Kinghorn (1991) δ-(L-α-aminoadipyl)-L-cysteinyl-D-valine synthetase from *Aspergillus nidulans*. Molecular characterization of the acvA gene encoding the first enzyme of the penicillin biosynthetic pathway *J. Biol. Chem.* 266, 12646

T. Maniatis, E. F. Fritsch and J. Sambroock, *Molecular cloning: a laboratory manual*, Cold Spring Harbor Laboratory, Cold Spring Harbor 1982/1.

H. Nakajima, T. Hamasaki, k. Tanaka, Y. Kimura, S. Udagawa and Y. Horie (1989) Production of Cyclosporin by fungi belonging to the genus Neocosmospora, *Agric. Biol. Chem.* 53 (1989) Nr. 8, S. 2291–2292.

J. C. Pierce and N. Sternberg (1991), Using the bacteriophage P1 system to clone high molecular weight (HMW) genomic DNA, *Methods Enzymol.* in press J. C. Pierce, B. Sauer and N. Sternberg (1992), A positive selection vector for cloning high molecular weight DNA by the bacteriophage P1 system: Improved cloning efficacy. *Proc. Natl. Acad. Sci. USA* 89 2056–2060.

J. Sambroock, E. F. Fritsch and T. Maniatis, *Molecular Cloning: a laboratory manual* Cold Spring Harbor Laboratory Press, Cold Spring Harbor 1989/2

D. J. Smith, A. J. Earl and G. Turner (1990) The multifunctional peptide synthetase performing the first step of penicillin biosynthesis in Penicillium chrysogenum is a 421.073 dalton protein similar to *Bacillus brevis* peptide antibiotic synthetases *EMBO J.* 9, 2743–2750

C. Staben, B. Jensen, M. Singer, J. Pollock, M. Schechtman, J. Kinsey and E. Selker (1989) Use of a bacterial Hygromycin B resistance gene as a dominant selectable marker in Neurospora crassa transformation, *Fungal Genetics Newsletter* 36 (1989), S. 79.

S. Tada, K. Gomi, K. Kitamoto, K. Takahashi, G. Tamura und S. Hara (1991) Construction of a Fusion Gene Comprising the Taka-Amylase- A Promoter and the Escherichia-Coli beta-Glucuronidase Gene and Analysis of Its Expression in Aspergillus-Oryzae, *Mol Gen Genet* 229 (1991) Nr. 2, S. 301–306.

M. Tropschug, D. W. Nicholson, F. Hartl, H. Köhler, N. Pfanner, E. Wachter and W. Neupert (1988) Cyclosporin A-binding Protein (Cyclophilin) of Neurospora crassa. One gene codes for both the cytosolic and mitochondrial forms. *Journal of Biological Chemistry* 263 (1988) Nr. 28, S. 14433–14440.

K. Turgay, M. Krause, and M. A. Marahiel (1992) 4 Homologous Domains in the Primary Structure of GrsB Are Related to Domains in a Superfamily of Adenylate-Forming Enzymes *Molecular Microbiol.* 6, 4, 529–546

R. Weckermann, R. Fuerbass and M. A. Marahiel (1988) Complete nucleotide sequence of the tycA gene encoding the tyrocidine synthetase 1 from *Bacillus brevis Nucleic Acids Res.* 16, 11841

P. H. Yu (1983) Specific Photoactivated Covalent Binding of S-Adenosyl-Methionine to Phenylethanolamine-N-Methyl Transferase *Biochim. Biophys. Acta* 742, 517

R. Zocher, T. Nihira, E. Paul, N. Madry, H. Peeters, H. Kleinkauf and U. Keller (1986). Biosynthesis of Cyclosporin A: Partial Purification and Properties of a Multifunctional Enzyme from Tolypocladium inflatum. *Biochemistry* 25, 550–553

---

What is claimed is:

1. An isolated DNA sequence encoding an enzyme which catalyzes the biosynthesis of cyclosporin A.

2. An isolated DNA sequence according to claim 1 encoding the enzyme of SEQ ID NO:2.

3. An isolated DNA sequence according to claim 2 comprising the DNA sequence of SEQ ID NO:1.

4. A recombinant vector comprising a DNA sequence encoding an enzyme which catalyzes the biosynthesis of cyclosporin A.

5. A recombinant vector according to claim 4 comprising a DNA sequence encoding the enzyme of SEQ ID NO:2.

6. A recombinant vector according to claim 5 comprising the DNA sequence of SEQ ID NO:1.

7. A host cell transfected with a recombinant vector according to claim 4.

8. A host cell transfected with a recombinant vector according to claim 6.

9. A process for producing cyclosporin A comprising culturing a host cell according to claim 7, expressing therefrom cyclosporin A and isolating cyclosporin A from the culture.

* * * * *